United States Patent
Herrmann et al.

(10) Patent No.: US 11,871,996 B2
(45) Date of Patent: Jan. 16, 2024

(54) SPINE MEASUREMENT SYSTEM AND METHOD THEREFOR

(71) Applicants: Erik Herrmann, Mesa, AZ (US); Scott Clegg, Scottsdale, AZ (US)

(72) Inventors: Erik Herrmann, Mesa, AZ (US); Scott Clegg, Scottsdale, AZ (US)

(73) Assignee: Orthosensor, Inc., Dania Beach, FL (US)

(*) Notice: Subject to any disclaimer, the term of this patent is extended or adjusted under 35 U.S.C. 154(b) by 42 days.

(21) Appl. No.: 16/710,230

(22) Filed: Dec. 11, 2019

(65) Prior Publication Data

US 2020/0107883 A1    Apr. 9, 2020

Related U.S. Application Data

(63) Continuation of application No. 15/335,348, filed on Oct. 26, 2016, now Pat. No. 10,595,941.

(51) Int. Cl.
*G06K 9/00*     (2022.01)
*A61B 34/10*    (2016.01)
(Continued)

(52) U.S. Cl.
CPC .............. *A61B 34/10* (2016.02); *A61B 5/407* (2013.01); *A61B 5/1079* (2013.01);
(Continued)

(58) Field of Classification Search
CPC ....... A61B 34/10; A61B 1/317; A61B 5/4528; A61B 5/4533; A61B 5/4538;
(Continued)

(56) References Cited

U.S. PATENT DOCUMENTS 6,402,762 B2    6/2002    Hunter et al.
6,477,400 B1    11/2002   Barrick
(Continued)

OTHER PUBLICATIONS

Kraus MD, Dehner C, Riepl C, Schöll H, Gebhard F. A novel method of image-based navigation in fracture surgery. Arch Orthop Trauma Surg. Jun. 2012;132(6):741-50. doi: 10.1007/s00402-012-1471-1. Epub Feb. 17, 2012. PMID: 22350052. (Year: 2012).*

(Continued)

*Primary Examiner* — Andrew M Moyer
(74) *Attorney, Agent, or Firm* — Bookoff McAndrews, PLLC

(57) ABSTRACT

A spine measurement system comprises an optical measurement probe, one or more targets, a fluoroscope, and a remote station. A-P and lateral images of the spine are taken using the fluoroscope and provided to the remote station. The remote station includes computer vision that can identify endplates and pedicle screws in the spine. The computer vision in the remote station is further used to identify vertebra and bone landmarks of the spine. The remote station can generate quantitative measurement data such as Cobb angles and axial rotation of the spine from the fluoroscope images that correspond to the spine deformity. The optical measurement probe can send images of the spine with pedicle screw extenders extending from the pedicle screws to the remote station. The remotes station using computer vision can provide spine metrics in real-time by tracking position of the pedicle screw extenders.

17 Claims, 39 Drawing Sheets

(51) Int. Cl.
*A61B 5/00* (2006.01)
*A61B 5/107* (2006.01)

(52) U.S. Cl.
CPC ... *A61B 2034/102* (2016.02); *A61B 2034/105* (2016.02); *A61B 2034/107* (2016.02)

(58) Field of Classification Search
CPC ....... A61B 5/4523; A61B 5/00; A61B 5/0037; A61B 5/004; A61B 5/0042; A61B 5/047; A61B 5/1079; A61B 2034/102; A61B 2034/105; A61B 2034/107
USPC ...... 382/128–132; 378/4, 21; 702/8, 41, 172
See application file for complete search history.

(56) References Cited

U.S. PATENT DOCUMENTS

| | | | |
|---|---|---|---|
| 6,535,756 | B1 | 3/2003 | Simon et al. |
| 6,669,635 | B2 | 12/2003 | Kessman et al. |
| 6,711,432 | B1 | 3/2004 | Krause et al. |
| 6,856,828 | B2 | 2/2005 | Cossette et al. |
| 6,990,368 | B2 | 1/2006 | Simon et al. |
| 7,539,332 | B1 * | 5/2009 | Al-Dayeh ............ G06T 7/0012 382/128 |
| 7,606,613 | B2 | 10/2009 | Simon et al. |
| 7,630,753 | B2 | 12/2009 | Simon et al. |
| 7,715,605 | B2 | 5/2010 | Verre et al. |
| 7,768,498 | B2 | 8/2010 | Wey |
| 7,857,821 | B2 | 12/2010 | Couture et al. |
| 7,929,745 | B2 | 4/2011 | Walker et al. |
| 8,038,683 | B2 | 10/2011 | Couture et al. |
| 8,403,934 | B2 | 3/2013 | Anglibaud et al. |
| 8,457,930 | B2 | 6/2013 | Schroeder |
| 8,512,346 | B2 | 8/2013 | Couture |
| 8,532,807 | B2 | 9/2013 | Metzger |
| 8,696,675 | B2 | 4/2014 | Boutin et al. |
| 8,775,133 | B2 | 7/2014 | Schroeder |
| 8,784,425 | B2 | 7/2014 | Ritchey et al. |
| 8,838,205 | B2 | 9/2014 | Shoham et al. |
| 8,965,483 | B2 | 2/2015 | Couture et al. |
| 9,011,448 | B2 | 4/2015 | Roche et al. |
| 2003/0053673 | A1 | 3/2003 | Dewaele |
| 2004/0068187 | A1 | 4/2004 | Krause et al. |
| 2004/0086082 | A1 | 5/2004 | Foos et al. |
| 2005/0027187 | A1 * | 2/2005 | Barth ................ A61B 6/5247 600/407 |
| 2005/0267354 | A1 | 12/2005 | Marquardt et al. |
| 2006/0161052 | A1 | 7/2006 | Colombet et al. |
| 2007/0036416 | A1 * | 2/2007 | Tsai ...................... G06T 7/0012 382/128 |
| 2007/0249967 | A1 | 10/2007 | Buly et al. |
| 2007/0242869 | A1 | 11/2007 | Luo et al. |
| 2007/0274584 | A1 * | 11/2007 | Leow .................... G03B 42/02 382/132 |
| 2009/0306717 | A1 | 12/2009 | Kercher et al. |
| 2011/0096964 | A1 * | 4/2011 | Zheng .................... G06T 7/143 382/128 |
| 2011/0160572 | A1 | 6/2011 | McIntosh et al. |
| 2011/0313418 | A1 | 12/2011 | Nikonovas |
| 2012/0029389 | A1 | 2/2012 | Amiot et al. |
| 2012/0143623 | A1 | 6/2012 | Opfer et al. |
| 2013/0114866 | A1 | 5/2013 | Kasodekar et al. |
| 2013/0231672 | A1 | 9/2013 | Paradis et al. |
| 2014/0031829 | A1 | 1/2014 | Paradis et al. |
| 2014/0323845 | A1 | 10/2014 | Forsberg |
| 2016/0022176 | A1 * | 1/2016 | Le Huec ................ A61B 6/461 600/594 |
| 2016/0089195 | A1 * | 3/2016 | Cordaro ............ A61B 17/8863 606/279 |
| 2016/0210374 | A1 * | 7/2016 | Mosnier ................ G06F 30/00 |
| 2016/0270825 | A1 * | 9/2016 | Wentz ................ A61B 17/7016 |
| 2017/0000530 | A1 * | 1/2017 | McNally ............ A61B 17/7079 |
| 2017/0119281 | A1 | 5/2017 | Herrmann |
| 2017/0224418 | A1 | 8/2017 | Boettner et al. |
| 2018/0310993 | A1 * | 11/2018 | Hobeika ............ A61B 17/7016 |

OTHER PUBLICATIONS

Bielecka, Marzena, Rafal Obuchowicz, and Mariusz Korkosz. "The Shape Language in Application to the Diagnosis of Cervical Vertebrae Pathology." PloS one 13, No. 10 (2018): e0204546-e0204546. (Year: 2018).*

Behairy, Yaser M., et al. "Partial correction of Cobb angle prior to posterior spinal instrumentation." Annals of Saudi Medicine 20.5-6 (2000): 398-401. (Year: 2000).*

Lee, DH., Lee, SW., Kang, S.J. et al. Optimal entry points and trajectories for cervical pedicle screw placement into subaxial cervical vertebrae. Eur Spine J 20, 905-911 (2011) (Year: 2011).*

Zheng, Guoyan, and Lutz P. Nolte. "Computer-assisted orthopedic surgery: current state and future perspective." Frontiers in surgery 2 (2015): 66. (Year: 2015).*

* cited by examiner

Fig. 17B

264
- MANIPULATING THE SPINE
- DISPLAYING REAL-TIME METRICS ON THE DISPLAY OF THE REMOTE STATION
- DISPLAYING A SPINE IMAGE IN REAL-TIME TO THE DISPLAY OF THE REMOTE STATION
- STORING REAL-TIME METRICS IN REAL-TIME IMAGE ON THE REMOTE STATION CORRESPONDING TO A SPINE OUTCOME

266
- REVIEWING A PRE-OPERATIVE DEFINED ROD SHAPE
- DETERMINING IF THE PRE-OPERATIVE DEFINED SHAPE RESULTS IN A CORRECT SPINE OUTCOME
- MODIFYING A ROD SHAPE TO MEET THE SPINE OUTCOME BASED ON THE REAL-TIME METRICS

322
- VIEWING A SPINE WITH A CAMERA WHERE THE IMAGE DATA IS PROVIDED TO REMOTE STATION
- IDENTIFYING A TARGETED VERTEBRA FOR PEDICLE SCREW INSTALLATION
- FINDING A LOCATION FOR PEDICLE SCREW PLACEMENT ON THE TARGETED VERTEBRA WHERE THE REMOTE STATION USING COMPUTER VISION IDENTIFIES LANDMARKS ON THE VERTEBRA TO LOCATE A POINT OF ENTRY

324
- RETRIEVING INFORMATION FROM THE REMOTE STATION DETAILING THE LOCATION FOR PEDICLE SCREW PLACEMENT IN RELATION TO THE LANDMARKS ON THE TARGETED VERTEBRA

326
- GUIDING A TOOL TO A POINT OF ENTRY OF THE TARGETED VERTEBRA
- GUIDING A TRAJECTORY OF THE TOOL
- FORMING AN OPENING IN THE TARGETED VERTEBRA CORRESPONDING TO WHERE THE PEDICLE SCREW IS PLACED

328
- MONITORING THE TOOL IN REAL-TIME WITHIN THE FIELD OF VIEW OF THE CAMERA
- INDICATING CORRECT TOOL PLACEMENT TO FORM THE OPENING

330
- RETRIEVING INFORMATION FROM THE REMOTE STATION RELATED TO A CORRECT TRAJECTORY AT THE POINT OF ENTRY ON THE TARGET VERTEBRA
- INDICATING A TRAJECTORY OF THE TOOL IN REAL-TIME WHEREIN THE REMOTE STATION USING COMPUTER VISION RECOGNIZES THE TOOL AND THE TRAJECTORY OF THE TOOL

332
- PROVIDING FEEDBACK TO SUPPORT ALIGNING THE TOOL AT THE POINT OF ENTRY OF THE TARGETED VERTEBRA AND PLACING THE TOOL AT THE CORRECT TRAJECTORY

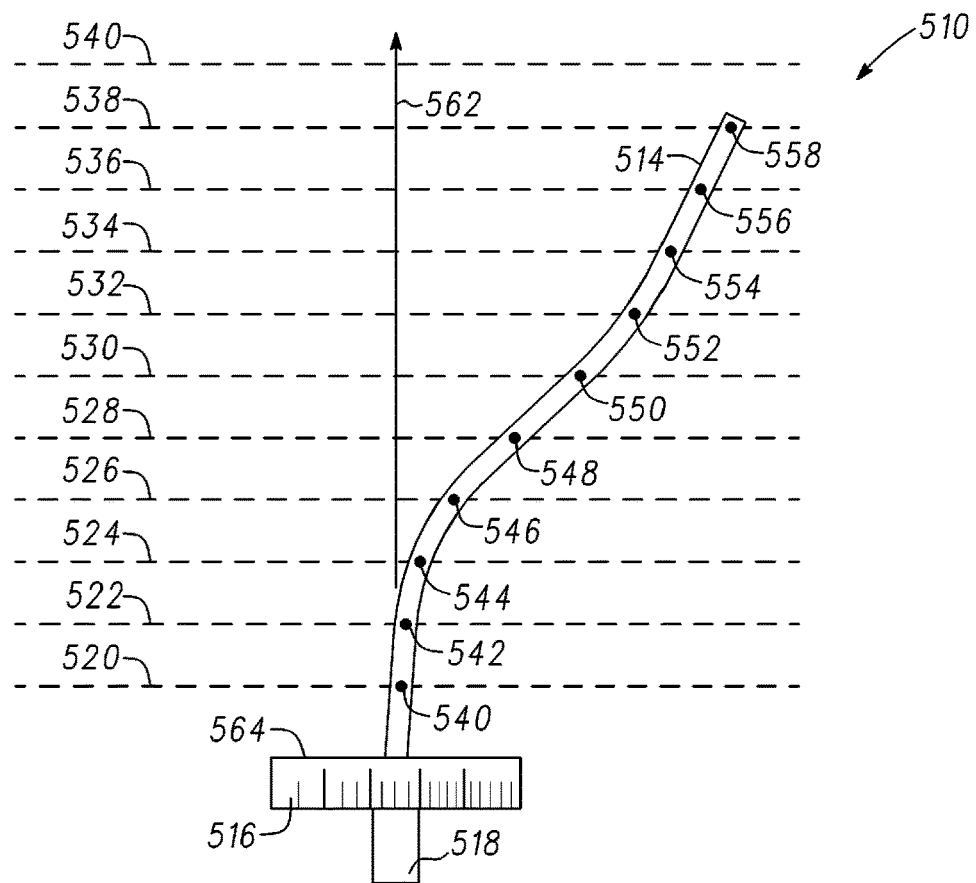
Fig. 28
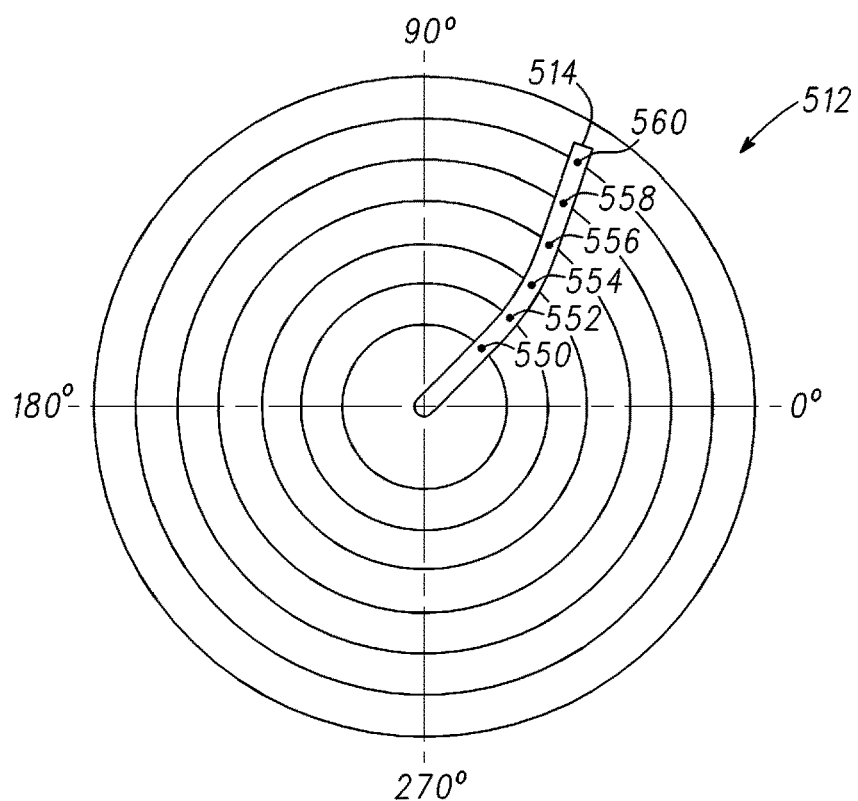

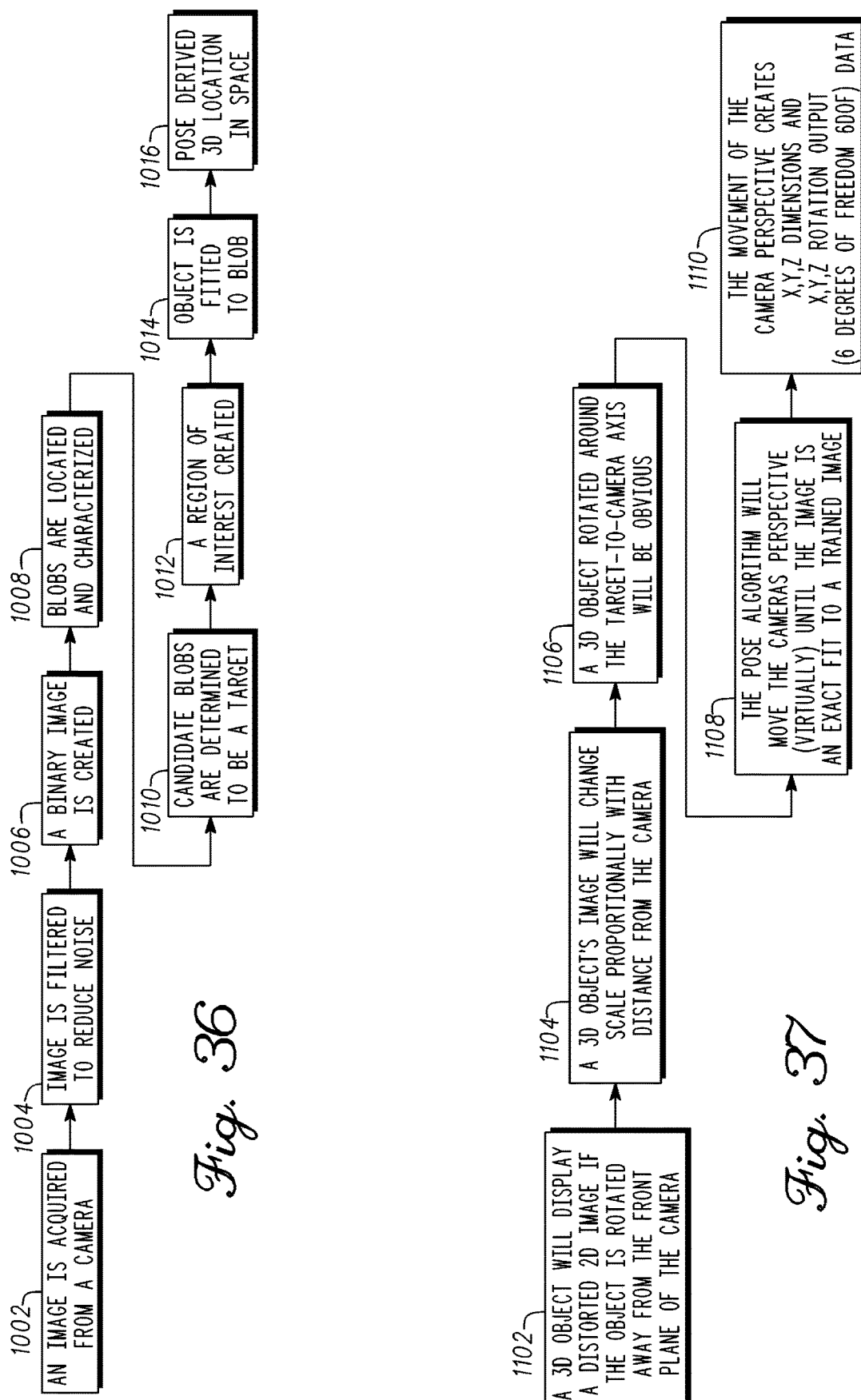

SPINE MEASUREMENT SYSTEM AND METHOD THEREFOR

FIELD

The present invention pertains generally to measurement of physical parameters, and particularly to, but not exclusively, medical electronic devices for high precision measurement of the spine.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the musculoskeletal system. Ligaments can position, hold, and stabilize one or more bones of a joint. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for correction of the musculoskeletal system has been standardized to meet the general needs of a wide distribution of the population. Although the tools, procedure, and artificial replacement systems meet a general need, each replacement procedure is subject to significant variation from patient to patient. The correction of these individual variations relies on the skill of the surgeon to adapt and fit the replacement joint using the available tools to the specific circumstance. It would be of great benefit if a system could be developed that improves surgical outcomes and reduces the cost and time of a surgery.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 17B is a continuation of the block diagram 17A;

FIG. 19 is a block diagram of a method to support pedicle screw placement in accordance with an example embodiment;

FIG. 28 is a side view image and a top view image of a rod and an encoded collar in accordance with an example embodiment;

FIG. 36 is a block diagram illustrating a tracking of targets such as pedicle screw extenders in accordance with an example embodiment;

FIG. 37 is a block diagram illustrating a pose derived 3D location in space from a 2D image in accordance with an example embodiment;

DETAILED DESCRIPTION

Figure 1:
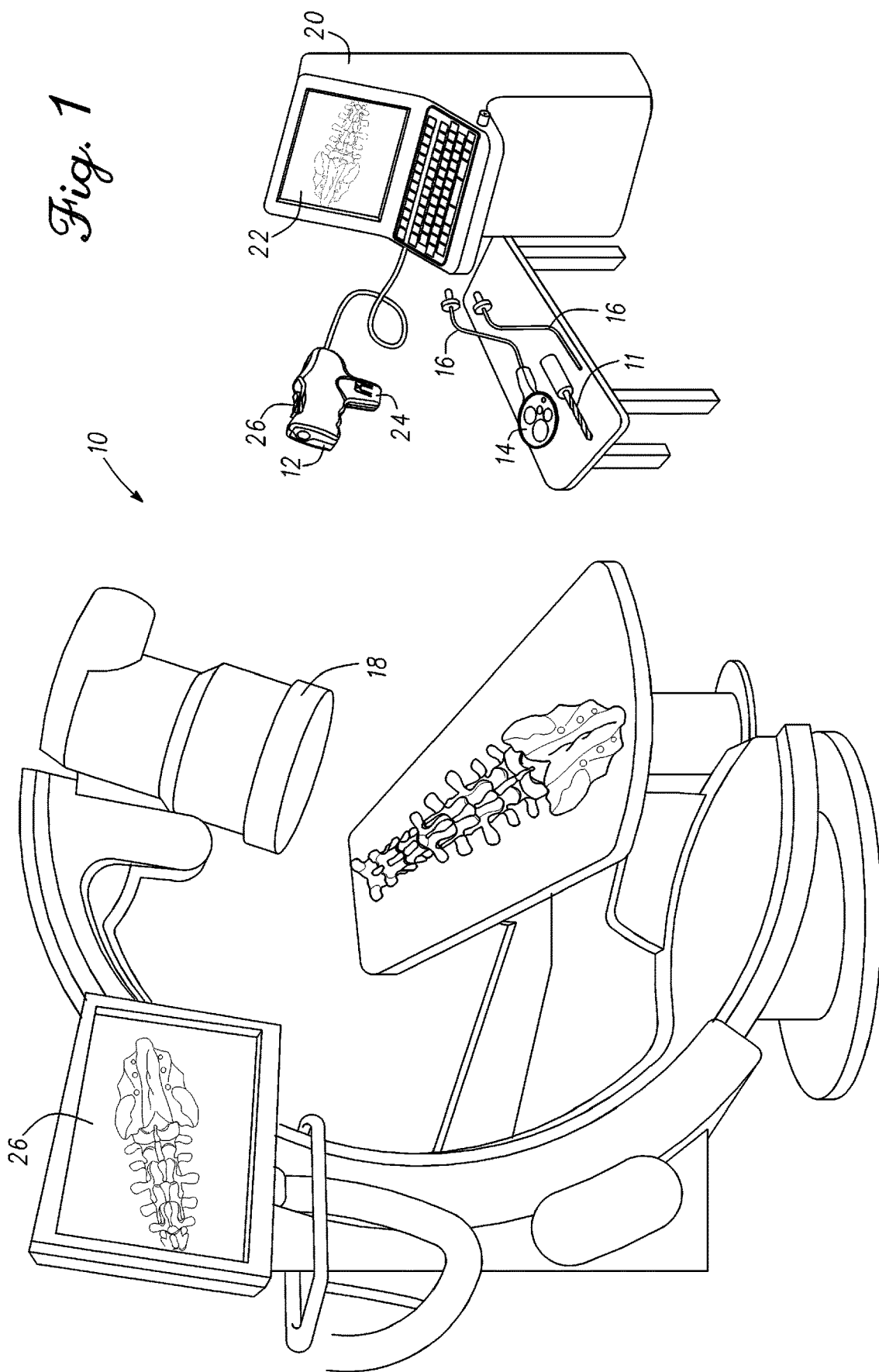
FIG. 1 illustrates a spine measurement system in accordance with an example embodiment.

Embodiments of the invention are broadly directed to measurement of physical parameters, and more particularly, to a system that supports accurate measurement, improves surgical outcomes, reduces cost, reduces time in surgery.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

In all of the examples illustrated and discussed herein, any specific materials, such as temperatures, times, energies, and material properties for process steps or specific structure implementations should be interpreted to be illustrative only and non-limiting. Processes, techniques, apparatus, and materials as known by one of ordinary skill in the art may not be discussed in detail but are intended to be part of an enabling description where appropriate. It should also be noted that the word "coupled" used herein implies that elements may be directly coupled together or may be coupled through one or more intervening elements.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

In general, a prosthesis is an artificial body part. An orthopedic implant is a device used to repair the musculoskeletal system. Common examples of an orthopedic implant are pins, rods, screws, cages, plates and other devices that typically couple to bone of the musculoskeletal system. A prosthetic joint can be part of a system that supports movement of the musculoskeletal system. A prosthetic joint typically comprises several prosthetic components that combine to mimic a natural joint. For example, a prosthetic hip joint comprises an acetabular shell, an acetabular bearing, a femoral prosthetic component. The acetabular shell couples to the pelvis and is a pivot point of the joint. The acetabular bearing fits in the acetabular shell and provides a bearing surface that supports hip movement. The femoral prosthetic component comprises a femoral head and a femoral hip stem. The head couples to the hip stem and fits into the acetabular bearing to distribute loading to the bearing surface. The femoral hip step couples to the proximal end of the femur. Thus, a prosthetic hip joint is a ball and socket joint that couples the femur to the pelvis to support movement of the leg. Similarly, prosthetic joints are available to repair the knee, ankle, shoulder, hand, fingers, wrist, toes, and spine.

The prosthetic joint or a prosthetic component of the joint can also have a number of sensors for generating measurement data related to the installation. For example, joint position or prosthetic component loading can be monitored in surgery or long-term. A result of the monitoring could be that an exercise regimen could be prescribed to improve the range of motion. Similarly, balance, loading, alignment, or joint position could be monitored or data stored to study kinematics of the joint or provide a kinetic assessment of the joint. Also, the joint could be monitored for wear or pending failure. In all cases, the measurement data can be used to enhance performance, reliability, and identify potential failure in a time frame when it can be repaired with a minimally invasive procedure.

FIG. 1 is an illustration of a spine measurement system 10 in accordance with an example embodiment. Spine measurement system 10 comprises an optical measurement probe 12, one or more targets 14, mounts 16, a fluoroscope 18, a drill 11 and a remote station 20. Spine measurement system 10 is configured to provide quantitative measurement data related to the spine. In one embodiment, spine measurement system 10 is configured for use in a surgical environment such as an OR (Operating Room) within a hospital to provide quantitative measurement data on the position of vertebrae, vertebra identification, measurement of angles related to vertebra, vertebral modeling, range of motion, extract kinematics (TKA, THA), and spine simulation. Corrections made to the spine can be monitored in real-time to determine a total change to a spine region of interest and if further modifications are need to achieve a desired outcome.

In general, hospital, clinics, and medical offices have reduced budgets for capital expenditures. At the same time, medical outcomes both short-term and long-term need to be improved to lower cost. Spine surgery is especially problematic in that much of the outcome is determined by the skill of the surgeon. Many surgeons do not spend sufficient time in the operating room on spine surgeries to feel comfortable with many of the required skills such as placing pedicle screws in the vertebra. The surgeon often compensates by using techniques that require iterative steps to ensure correct location of the pedicle screw. Similarly, surgeons new to spine surgery require substantial time under the guidance of a skilled surgeon to train and develop the techniques that yield successful outcomes. Spine measurement system 10 improves outcomes by supporting spine surgeries with quantitative measurement data related to spine shape, pedicle screw placement, prosthetic component placement, load measurement, and rod shape. For example, spine measurement system 10 can support pedicle screw installation by identifying the location where the pedicle screw is placed on the vertebra and in real-time time provide data to support drill 11 placement at a correct point of entry on a targeted vertebra and a correct trajectory of a drill path into the targeted vertebra. Spine measurement system 10 generates quantitative measurement data related to spine shape and measure an outcome based on real-time spine measurements. Furthermore, spine measurement system 10 can display the spine in real-time, generate angles of relevance to the spine, analyze the spine based on the measurements, provide corrections, and one or more workflows to achieve the desired outcome. The use of quantitative measurement data and workflows backed by clinical evidence can improve the surgical outcome and reduce the surgical time.

As mentioned previously, capital cost of equipment can be a barrier to providing devices that can significantly improve spine surgery outcomes. Spine measurement system 10 is designed to be low cost where some of the components are disposed of after a single use. Fluoroscope 18 is part of spine measurement system 10. Fluoroscope 18 is a common device that is present in the operating room for spine surgery. Thus, fluoroscope 18 is not required for purchase thereby substantially reducing the system cost. As used today, the fluoroscope is not used to generate any quantitative measurements but is used to provide images of the spine during surgery for review and verification. Alternatively, a catscan (CT) or magnetic resonance imaging can be used in place of a fluoroscope image. The CT or MRI would be provided to remote station 20. Optical measurement probe 12, mount 16, and target 14 are disposable components that can be built at low cost while providing the performance, accuracy, and reliability required to provide measurement data to support a spine surgery. The cost of optical measurement probe 12, mount 16, and target 14 can be incorporated into the cost of surgery and invoiced at the time of surgery which eliminates an equipment capital cost or maintaining an inventory of components. Remote station 20 processes information received from optical measurement probe 12 to generate quantitative measurement data to support the spine surgery. In one embodiment, optical measurement probe 12 comprises a camera and provides image data to remote station 20. In one embodiment, measurement system 10 can comprise more than one camera. Remote station 20 can be purchased, leased, or given to the entity using spine measurement system 10. No capital expenditure is required by leasing or providing remote station 20 at no cost. Providing remote station 20 at no cost can be accommodated if surgical volumes are sufficient. Leasing of remote station 20 may be practical for an entity having low volume of spine surgeries while achieving better spine outcomes. In general, providing the low cost solution requiring little or no capital expenditure and no paid inventory is a solution to get equipment in the operating room where it can benefit the surgeon, the patient, and the hospital by reducing surgical time, increasing the accuracy of the surgery, generate quantitative measurement data, reduce rehabilitation time, and improve patient outcomes long-term.

In general, a surgeon first meets with the patient and generates a diagnosis. Each diagnosis is unique to the individual and situation. The diagnosis may require surgery to resolve the problem. Typically, the surgeon generates a pre-operative plan that defines the spine region of interest and the objectives to be achieved. The pre-operative plan is designed to be imported to spine measurement system 10. In one embodiment, spine measurement system 10 can include a workflow corresponding to the type of surgery being performed where questions are answered by the surgeon that relate to the surgery. For example, system 10 can be used to support the installation and positioning of orthopedic implants such as pins, rods, screws, cages, plates and other devices that typically couple to bone of the musculoskeletal system. Spine measurement system 10 in the operating room can couple to the cloud and download the pre-operative plan. In one embodiment, all data coming to spine measurement system 10 is encrypted. Similarly, any outflow of data or information from spine measurement system 10 is encrypted to prevent others from viewing the data. Information displayed on the spine measurement system 10 may include patient information, the diagnosis, the vertebrae being operated on, metrics, the hardware being used in the surgery, goals and expected results of the surgery, a workflow of the surgery, measurement data, analysis, and other miscellaneous information. In the example, spine measurement system 10 can display an image of the spine as the surgeon envisions an end result when the surgery is completed. The pre-operative image can be compared in real-time to the spine in surgery to determine differences between the pre-operative plan and the actual surgery. Spine measurement system 10 supports changes or modifications during surgery that yield the desired surgical outcome or modifications due to unforeseen issues that were not seen or disclosed in the pre-operative planning.

Fixed references are used to generate a coordinate system with measurement probe 12. In one embodiment, spine measurement system 10 is referenced to static objects that are in the operating room. For example, vents, light fixtures, switches, and other objects that do not change position can be used as references. Typically, three static points are used as reference points. Spine measurement system 10 can take into account position changes in the spine by also identifying reference points of the patient, spine or other patient points of reference that correspond to the coordinate system generated by spine measurement system 10 using the static objects. In one embodiment, optical measurement probe 12 is used to reference the three static points. Images of the references are sent to remote station 20. Remote station 20 can view the images and determine if a position has changed and compensate future measurements for the new orientation. Alternatively, system 10 can measure the relative position of objects in the field of view of optical measurement probe 12 whereby the measurements are independent of the camera coordinate system.

The surgeon resects tissue, ligaments, and muscle in a spine region to expose a portion of the spine. Fluoroscope 18 can be rotated to take images of the spine from different angles. Typically, anterior-posterior image and a lateral image are taken of the spine region of interest. Spine surgery to repair a lumbar region of the spine is used as an example of spine measurement system 10 generating quantitative measurement data in support of the operation. System 10 can be used on all regions of the spine such as cervical, thoracic, lumbar, and sacral spine regions. The repair of the lumbar region in the example will comprise fastening a rod to pedicle screws inserted in L2-L4 vertebrae. The rod is bent by the surgeon to modify the curvature of the lumbar region of the spine when coupled to the pedicle screws. The L2-L4 vertebrae are fused together to hold the new shape. The rod will maintain the desired shape of the spine while the fusing takes hold and strengthens to a point where the rod can be removed. It should be noted system 10 can be used for spine surgeries of two or more vertebrae including modifying the entire spine and is not limited by the example.

Fluoroscope 18 generates anterior-posterior and lateral images of each vertebra to support placement of pedicle screws. Placement of pedicle screws can be a time consuming procedure for surgeons. The pedicle screw placement process is iterative whereby a hole is drilled partially into the bone and fluoroscope images are taken. A wire can also be used to probe into the vertebra instead of drilling. The depth of the hole can be increased after verification of a correct drill path by fluoroscope images. Typically, the drill path is approximately centered within the pedicle to maximize the bone area around the screw. The drill path is different for each vertebra. After drilling the pilot path, the opening can be widened and tapped to accept a pedicle screw. In one embodiment, optical measurement probe 12 can be used to take images of a display 25 of fluoroscope 18 during the pedicle placement process and after the pedicle screw is placed. Optical measurement probe 12 includes a handle 24 that fits in the hand allowing it to be aimed at display 26 of fluoroscope 18. Optical measurement probe 12 is coupled to and sends the images to remote station 20. In one embodiment, the surgeon can identify the vertebra or vertebrae corresponding to the fluoroscope images. Remote station 20 uses computer vision to identify the vertebra or vertebrae from the fluoroscope images and generates a representation of the spine in the fluoroscope images on display 22 of remote station 20. The surgeon responds to verify that that the identification is correct. For example, the spine image can be displayed on display 22 of remote station 20 with a box around a vertebra with a label indicating the vertebra (e.g. L1, L2, L3 . . . ). The surgeon can use switch 26 on optical measurement probe 12 to interact with the user interface on remote station 20 to verify that the label is correct. Alternatively, if the vertebra label is incorrect the surgeon can use switch 26 to change the label to the appropriate vertebra. Verification sets the vertebral sequence on display 22 since the sequence of vertebra is known. Alternatively, voice recognition can be used for the surgeon in a verification process with remote station 20.

Remote station 20 processes the images from fluoroscope 18 to generate quantitative measurement data relevant to the spine surgery. The fluoroscope images will show detail of the spine including bone detail, landmarks, pedicle screws within a vertebra and endplates of each vertebra. Instead of taking an image of a display 25 with optical measurement probe 12, fluoroscope 18 can directly send image data to remote station 20. Fluoroscopes in a hospital, clinic, or office are can vary significantly and may not port easily to remote station 20. In other words, fluoroscope 18 would have to be set up to interface with spine measurement system 10. Images can be coupled from fluoroscope 18 or optical measurement probe 12 by wired or wireless connection.

Quantitative measurement data is generated by remote station 20 using the images provided by fluoroscope 18. In one embodiment, the fluoroscope images are digital images. Remote station 20 comprises microprocessors, digital signal processors, microcontrollers, interface circuitry, control logic, memory, digital circuitry, sensors, analog circuitry, transceiver circuitry, converters, display 22, and other circuitry. Remote station 20 can run software and can interface with devices that interact with the external environment. In one embodiment, remote station 20 is a computer, tablet, or a portable device. Remote station 20 can also provide feedback such as visual, audible, and haptic feedback to a surgical team. Remote station 20 also couples to the internet, one or more databases, and the cloud. A software program implementing computer vision is used by remote station 20 to generate quantitative measurement data such as Cobb angle or the compression or distraction of the distance between vertebral endplates used by surgeons to assess the spine. For example, system 10 can get a baseline of the junctional endplates to define predictive kyphosis or support other similar measurements. Computer vision attempts to recreate the ability of human vision to perceive and understand what an image is. Computer vision does not just process the image data but uses visual cues that are common to other similar objects ascertain what is being viewed. One advanced area using computer vision software is in facial recognition. For example, a computer can be programmed to recognize a fork. Not all forks look the same but have many features in common with each other. Machine vision can recognize a fork having substantial equal dimension's to what is stored in memory. The machine vision may not recognize the fork if it is altered. Conversely, a human can view a fork that he or she has never seen before, process the image, and determine that it is a fork even with the differences. A computer with computer vision tries to mimic this human process. The computer vision software will have identifiers or visual cues to look for that in combination can allow the program to conclude that what is being shown is a fork. Moreover, the entire fork may not be visible but with sufficient identifiers located on the image the computer vision could conclude that it is a fork even with only a partial view.

Remote station 20 is configured to use computer vision software to recognize the musculoskeletal system. In one embodiment, the computer vision software is configured to recognize the spine, vertebrae, and bone landmarks of each vertebra. Furthermore, the computer vision software is configured to recognize equipment, tools, and components used in the surgery. For example, equipment such as pedicle screws and screw extenders placed in the spine can be recognized by the computer vision software. The recognition of the spine and equipment is used to generate quantitative measurement data that is used by the surgeon in real-time. In one embodiment, Cobb angles can be measured using recognition of vertebral end plates and pedicle screws. A Cobb angle is a measurement to characterize spine curvature in a region of the spine. The Cobb angle can be measured in the coronal plane using anteroposterior fluoroscope images to indicate deformity from the ideal. Similarly, the Cobb angle can be measured using lateral fluoroscope images to characterize deformities or curvature in the sagittal plane. Rotational aspects of vertebra to a reference can also be measured by remote station 20. In general, measurements are not limited to the sagittal plane. Sagittal images can be combined with lateral and anterior-posterior images to utilize coronal and axial planes using anatomical and instrument landmarks.

Figure 2:
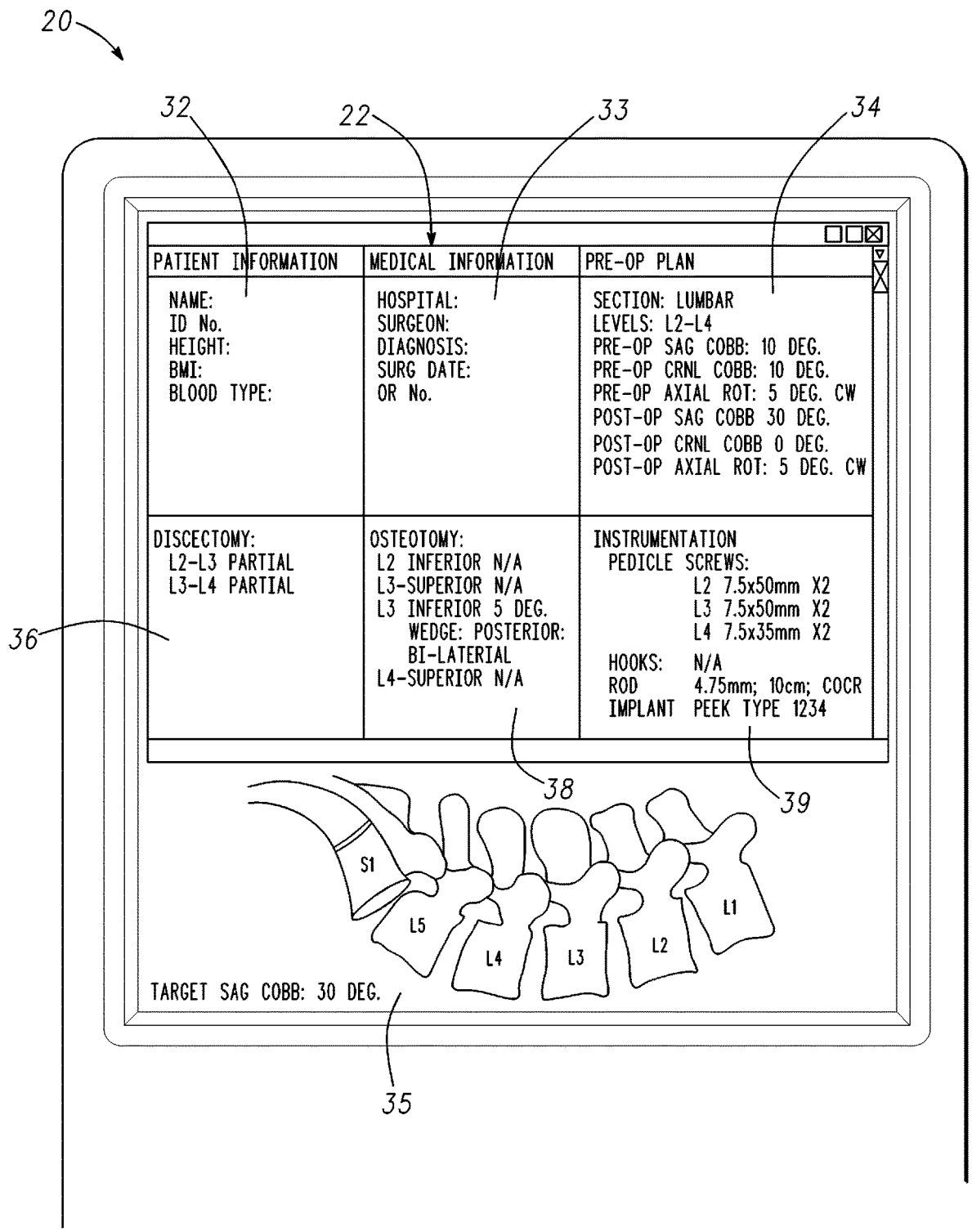
FIG. 2 is an illustration of the display of the remote station with a pre-operative plan in accordance with an example embodiment.

FIG. 2 is an illustration of display 22 of remote station 20 with a pre-operative plan in accordance with an example embodiment. Display 22 of remote station 20 displays a pre-operative plan for the spine surgery. As mentioned previously, remote station 20 can be coupled through the internet or cloud to retrieve the information that the surgeon has prepared. Remote station 20 will decrypt the information received. The surgeon will use this information during the course of the surgery and can refer back to it if required. In one embodiment, an electronic form can be filled out by the surgeon related to the surgery whereby basic information is recorded, stored, received by remote station 20, and displayed on display 22. Moreover, specific information or notes needed by the surgeon can be added or highlighted. Display 22 can also include figures, pictures, spine scans that relate to the pre-operative plan. For example, a figure of a post-operative outcome of the spine region of interest based on the pre-operative plan can be displayed in section 35 of display 22 of remote station 20. In one embodiment, the projected post-operative outcome could be compared to the spine in surgery in real-time.

Display 22 can be divided into sections with pre-operative information related to the surgery. A section 32 comprises patient information. Patient information displayed on display 22 of remote station 20 in section 32 can comprise patient name, patient identification number, height, body mass index, and blood type. The patient information shown illustrates what can be put in section 32 but is not limited to this data. Other information can be added or removed depending on what is relevant for the specific surgery.

A section 33 comprises medical information. Medical information displayed on display 22 of remote station 20 can comprise a hospital, surgeon name, medical diagnosis, a surgical date, and an operating room number. The medical information shown illustrates what can be put in section 33 but is not limited to this data. Other information can be added or removed depending on what is relevant for the specific surgery.

A section 34 comprises a pre-operative plan for the surgery. Pre-operative plan information displayed on display 22 of remote station 20 can comprise pre-operative measurement information, spine modification information, and expected post-operative outcome information. The pre-operative plan information comprises a section of the spine to be operated on, vertebrae of interest, Cobb angles, and axial rotation. In the example, pre-operative sagittal Cobb angle, pre-operative coronal Cobb angle, and pre-operative axial rotation are provided on display 22. The type and amount of pre-operative information will vary with the type of surgery being performed. In the example, a post-operative sagittal Cobb angle, post-operative coronal Cobb angle, and a post-operative axial rotation are provided. Pre-operative and post-operative axial rotation includes the direction of rotation. The type and amount of post-operative information will vary with the type of surgery being performed. Other information can be added or removed depending on what is relevant for the specific surgery.

A section 36 comprises discectomy information on display 22 of remote station 20. In the example, the surgery is being performed in the lower lumbar region. More specifically, surgery is being performed on vertebrae L2-L4 where a spine deformity is being corrected requiring correction in the sagittal and coronal planes. Discectomy information relates to the disc material being removed from the spine. In the example, L2-L3 and L3-L4 are identified as regions for discectomy. Further information can also be provided such as the discectomy of vertebrae L2-L3 and L3-L4 are partial discectomies. Other information can be added or removed depending on what is relevant for the specific surgery.

A section 38 comprises osteotomy information on display 22 of remote station 20. As mentioned, the surgery is being formed in the lower lumbar region in the example. Each vertebra of the spine surgery is listed. Osteotomy information discloses bone cuts or bone modifications to reduce medical problems related to the spine and to support change to the spine shape. In the example, the L3 vertebra inferior requires modification as disclosed in section 38. Other information can be added or removed depending on what is relevant for the specific surgery.

A section 39 comprises instrumentation used during the surgery. As shown, components that couple to the spine to modify spine shape are listed. In the example, pedicle screws, a rod, and an implant are listed on display 22 of remote station 20. Each pedicle screw may have a different length or profile. Pedicle screws are listed corresponding to each vertebra with information related to size and length of the screw. The rod length and diameter of the rod to modify spine shape is disclosed. Implants used in the operation are also listed on display 22. Other information can be added or removed depending on what is relevant for the specific information. For example, pedicle screw extenders that can be recognized by optical measurement probe 12 of FIG. 1 could be added to section 39 as will be discussed hereinbelow.

Figure 3:
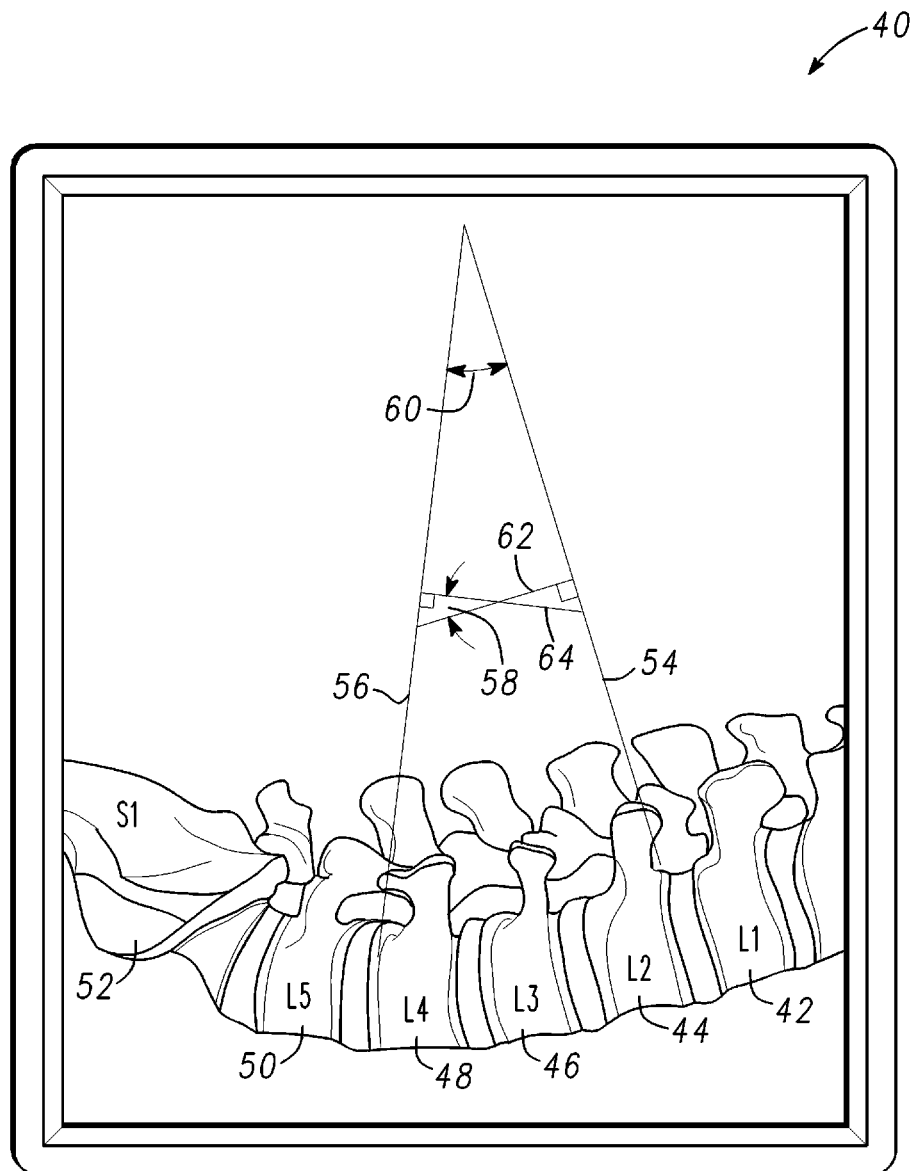
FIG. 3 is an illustration of a lateral fluoroscope image of a lumbar region of the spine in accordance an example embodiment.

FIG. 3 is an illustration of a lateral fluoroscope image 40 of a lumbar region of the spine in accordance of an example embodiment. Lateral fluoroscope image 40 has been received by remote station 20 of FIG. 1. The lumbar region comprises L1 vertebra 42, L2 vertebra 44, L3 vertebra 46, L4 vertebra 48, L5 vertebra 50, and S1 sacrum 52. The vertebrae of the lumbar region have been labeled in remote station 20 and verified by the surgeon. Computer vision within remote station 20 of FIG. 1 is configured to identify the endplates of each vertebra. In the example, vertebrae L2-L4 are being corrected for a curvature and rotational deformity. The Cobb angle of the vertebrae L2-L4 is calculated from fluoroscope image 40 and the quantitative measurement is displayed on display 22 of remote station 20 of FIG. 1. The Cobb angle is used by the surgeon as a measure of the deformity of the spine in the region of interest and can be compared against the pre-operative plan to determine if changes are required.

Remote station 20 of FIG. 1 can calculate Cobb angle using at least two methods. A first method extends the planes of the endplate surfaces of interest to intersection and measures the angle between the planes. In the example, a plane of the proximal endplate of vertebra L2 corresponding to the proximal endplate surface is extended from the spine. The proximal endplate plane of vertebra L2 is indicated as line 54. Similarly, a plane of the distal endplate of vertebra L4 corresponding to the distal endplate surface is extended from the spine. The distal endplate plane of vertebra L4 is indicated as line 56. In the first method, lines 55 and 56 are extended until intersection. Remote station 20 of FIG. 1 calculates an angle between lines 55 and 56 which is the Cobb angle 60 for the example embodiment.

Alternatively, a line 62 can be extended at a right angle from line 54. A line 64 can be extended at a right angle from line 56. In the example, both lines 62 and 64 extend interior to Cobb angle 60 from the example hereinabove. Lines 62 and 64 are extended to intersection. Remote station 20 of FIG. 1 calculates an angle between lines 62 and 64. The angle is indicated by Cobb angle 58. Cobb angle 58 is equal to Cobb angle 60.

Figure 4:
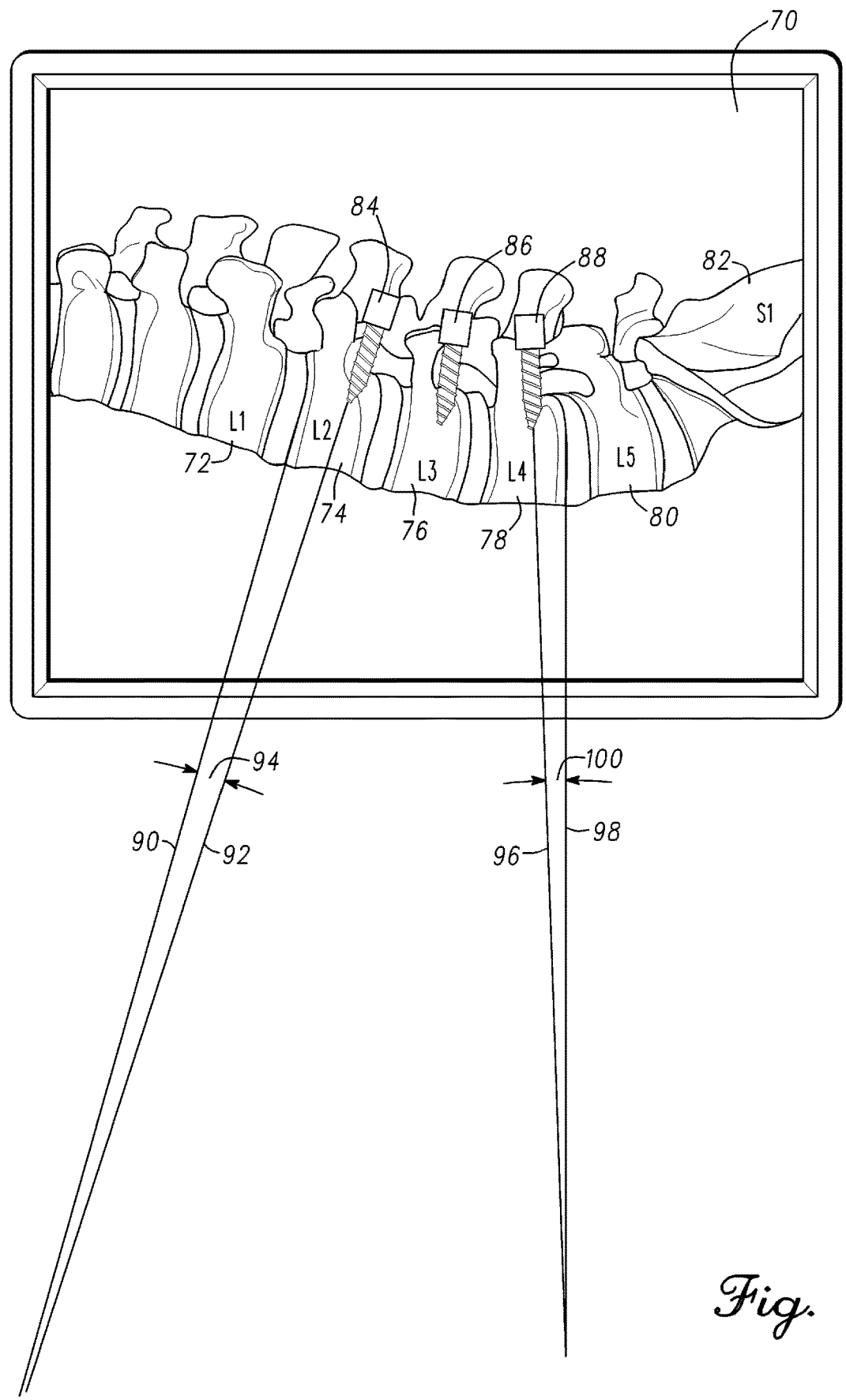
FIG. 4 is an illustration of a lateral fluoroscope image of the lumbar region of the spine in accordance with an example embodiment.

FIG. 4 is an illustration of a lateral fluoroscope image 70 of the lumbar region of the spine in accordance with an example embodiment. Referring briefly to FIG. 3, the fluoroscope image 40 did not show the pedicle screws to simplify the drawing and illustrate measurement of the Cobb angle by remote station 20 of FIG. 1. Referring back to FIG. 4, lateral fluoroscope image 70 shows pedicle screws inserted during surgery. Fluoroscope image 70 is sent directly to remote station 20 of FIG. 1 or optical measurement probe 12 can take an image of display 25 of fluoroscope 18 of FIG. 1. As mentioned previously, computer vision within remote station 20 of FIG. 1 can recognize anatomy of the musculoskeletal system, components, devices, and equipment. For example, remote station 20 of FIG. 1 can recognize pedicle screws that have been inserted in the spine. In general, remote station 20 of FIG. 1, will measure more than just the Cobb angle from the fluoroscope images although only the Cobb angle may be displayed of the quantitative measurement data. A table of the different measurements is generated and stored within memory of remote station 20 of FIG. 1 that can be recalled and used when required. For example, endplate to endplate, pedicle screw to pedicle screw, and pedicle screw to endplate measurements can be measured and stored in a table corresponding to the vertebrae of interest from the fluoroscope images.

In the example measurement, endplate to pedicle screw quantitative measurements are generated. Lateral fluoroscope image 70 of the spine has been imported to remote station 20 of FIG. 1. Fluoroscope image 70 includes the lower lumbar region of the spine. The lumbar region comprises L1 vertebra 72, L2 vertebra 74, L3 vertebra 76, L4 vertebra 78, L5 vertebra 80, and S1 sacrum 82. The vertebrae of the lumbar region is displayed and labeled on display 22 of remote station 20 of FIG. 1. The surgeon has verified that the spine image displayed on display 22 of remote station 20 of FIG. 1 is correct.

Fluoroscope image 70 further includes a pedicle screw 84, a pedicle screw 86, and a pedicle screw 88 respectively coupled to L2 vertebra 74, L3 vertebra 76, and L4 vertebra 78. The remote station application using computer vision is configured to identify the endplates of each vertebra and the pedicle screws. In the example, vertebrae L2-L4 are being corrected for a curvature and rotational deformity. Screw to endplate angle measurements can be used to determine an amount of correction required for the spine. As mentioned, the Cobb angle is an indication of the amount of deformity in the spine. Pedicle screw to endplate angles, endplate to endplate angles, and pedicle screw to pedicle screw angles quantitative measurements can be used to determine changes to individual vertebra or groups of vertebra in relation to the Cobb angle. Similarly, the same measurements can be made using an anteroposterior fluoroscope image of the spine for correction in the coronal plane. Also, rotational measurements and correction of the spine can be identified from the lateral and anteroposterior fluoroscope images.

An angle 94 relates to a proximal endplate of L2 vertebra 72 and pedicle screw 84. Remote station 20 of FIG. 1 locates the proximal endplate of L2 vertebra 72 and extends the plane of the proximal endplate of L2 vertebra 72. The plane corresponds to a surface of the proximal endplate and is indicated by line 90. Pedicle screw 84 is coupled to L2 vertebra 72. Remote station 20 of FIG. 1 locates a center of pedicle screw 84 and extends a trajectory of pedicle screw 84 to intersection with the plane of the proximal endplate of L2 vertebra 72 indicated by line 90. The trajectory of pedicle screw 84 is indicated by line 92. Remote station 20 of FIG. 1 measures an angle 94 that is formed between lines 90 and 92.

An angle 100 relates to a distal endplate of L4 vertebra 78 and pedicle screw 88. Remote station 20 of FIG. 1 locates the distal endplate of L4 vertebra 78 and extends the plane of the distal endplate from L4 vertebra 78. The plane corresponds to a surface of the distal endplate and is indicated by line 98. Pedicle screw 88 is coupled to L4 vertebra 78. Remote station 20 of FIG. 1 locates a center of pedicle screw 88 and extends a trajectory of pedicle screw 88 to intersection with the plane of the distal endplate of L4 vertebra 78 indicated by line 98. The trajectory of pedicle screw 88 is indicated by line 96. Remote station 20 of FIG. 1 measures an angle 100 that is formed between lines 96 and 98. In general, remote station 20 using computer vision generates quantitative measurement data comprising Cobb angles, vertebra endplate to endplate, pedicle screw to vertebra endplate, pedicle screw to pedicle screw, and other information from fluoroscope images generated during a pedicle screw procedure. The quantitative measurement data of the spine can be compared to the pre-operative plan and be used in the spine modification. In general, the fluoroscope images are used to generate quantitative measurement data that is used to characterize the spine an initial state. The initial state corresponds to the spine with the deformity being corrected. In one embodiment, the quantitative measurement data from the fluoroscope images is used to create a spine image with deformity that is displayed on display 22 of remote station 20 of FIG. 1. As will be disclosed hereinbelow, the spine is monitored during surgery with quantitative measurement data such as Cobb angle being provide in real-time as the spine shape is modified. The real-time spine monitoring includes quantitative measurement of spine shape that is interpolated with the initial spine shape to provide an image of the spine shape as it is manipulated on display 22 of remote station 20 of FIG. 1 in real-time.

Figure 5:
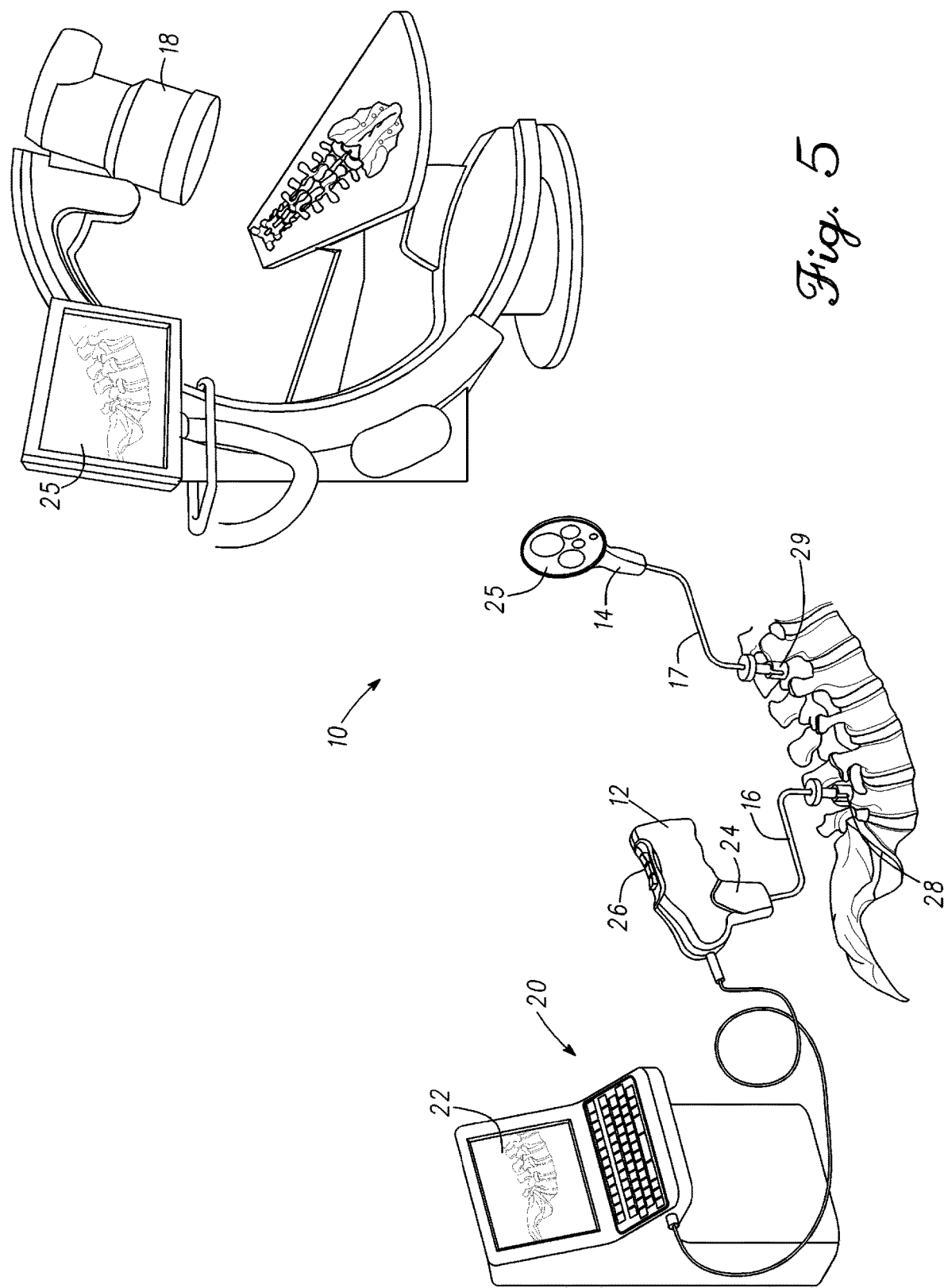
FIG. 5 is an illustration of the spine measurement system having the optical measurement probe and a target coupled to the spine in accordance to the example embodiment.

FIG. 5 is an illustration of spine measurement system 10 having optical measurement probe 12 and a target 14 coupled to the spine in accordance to the example embodiment. Optical measurement probe 12 and one or more targets are used to measure and monitor spine position in real-time during a surgery. Optical measurement probe 12 includes a camera configured to monitor one or more targets. In one embodiment, the camera is monocular. Alternatively, the camera can be binocular. A monocular camera is lower cost than a binocular camera which supports a disposable quantitative spine measurement device for the operating room. Optical measurement probe 12 can couple to the spine or to a reference position. Optical measurement probe 12 can also be mounted to a stable non-moving structure such as an operating table having a view of the spine during surgery. In general, spine measurement system 10 is configured to take absolute 6 degrees of freedom measurements throughout the procedure. In one embodiment, spine measurement system 10 is configured to use the camera center as its coordinate system origin. In another embodiment, system 10 is configured to measure the relative position of an object with respect to another object in the Field Of View. One or more algorithms can be used to identify and count the target devices or objects in the field of view.

As previously mentioned, optical measurement probe 12 can generate a reference image from the reference position. In one embodiment, three static objects within the within the field of view of the camera are used as references from the reference position. The optical measurement probe 12 can be moved from the reference position and then returned at a later time. It is possible that the angle of the camera with respect to the references can change slightly when the camera is repositioned. The change in angle will have subsequent affect on quantitative measurements made by spine measurement system 10. The camera upon being returned to the reference position will identify the references. Remote station 20 will not produce any change to image data received if the references are found to be in the same positions. Remote station 20 will calculate a three-dimensional compensation if the references are found to be positioned differently due to the camera being in a new position. Image data received by remote station 20 from optical measurement probe 12 will have this offset to ensure all data is measured identically and corresponds to the camera being in the original reference position.

As shown in the illustration, optical measurement probe 12 is coupled to a pedicle screw 28. A mount 16 couples between optical measurement probe 12 and pedicle screw 28. Mount 16 can have a predetermined shape that positions optical measurement probe 12 from being directly over the spine. In one embodiment, mount 16 couples to handle 24 of optical measurement probe 12. Handle 24 includes a quick release that allows optical measurement probe 12 to be removed from mount 16. This feature can be used is to take an image of the spine or an image of display 26 of fluoroscope 18 where optical measurement probe 12 can be held in hand and directed at an object. Optical measurement probe 12 can be reattached to mount 16 after the images have been taken thereby placing the device in the position it was previously in. Mount 16 is configured to couple to a pedicle screw. In one embodiment, mount 16 screws into a head region of pedicle screw 28. Tightening the distal end coupling of mount 16 to pedicle screw 28 fixes a position of optical measurement probe 12 in relation to the spine.

A camera within optical measurement probe 12 is focused on target 14. Similar to optical measurement probe 12, target 14 is coupled to a pedicle screw 29. A mount 17 couples between target 14 and pedicle screw 29. Mount 17 can have a predetermined shape that positions optical measurement probe 12 away from the spine. This affords the surgeon more room to perform spine manipulation and the surgery. Target 14 can be disengaged from mount 17 or can be permanently affixed to mount 17. In one embodiment, mount 17 screws into a head region of pedicle screw 29. Tightening the distal end coupling of mount 16 to pedicle screw 29 fixes a position of target 14 in relation to the spine. As previously mentioned, target 14 is in a field of view of the camera within optical measurement probe 12. More than one target can be coupled to the spine. Each target is in the field of view of the camera when coupled to the spine. Mounts can be adjusted to move targets such that at least a portion of the images on each target are in the field of view.

In one embodiment, target 14 has a surface 25 with multiple images that can be viewed by optical measurement probe 12. In one embodiment, images on target 14 are two-dimensional images. Alternatively, target 14 can have three-dimensional images formed on surface 25. As shown, target 14 comprises images of circles each having a different size. Optical measurement probe 12 tracks movement of the spine by comparing changes on the image of target 14 to the initial image of target 14 viewed by remote station 20. In the example, optical measurement probe 12 and target 14 is set up to track changes of one of the L2-L4 vertebrae. Other vertebra can be tracked by adding targets. Typically, the image of target 14 sent by optical measurement probe 12 to remote station 20 corresponds to the L2-L4 vertebrae being in the pre-operative state having the deformity that was measured on using the fluoroscope images. The spine can then be manipulated which changes the spine shape. Changes in the image viewed by the camera in optical measurement probe 20 can be converted to a three dimensional movement of the vertebra to which target 14 couples. The detected change in movement or rotation of the target is translated or rotated to a position change in 3D space of the vertebra to which the target couples. Software in remote station 20 can process the image data from optical measurement probe 20 and translate and rotate it to a change in spine shape and reflect this change to the image of the spine provided on display 22.

There is a direct correlation between the position in 3D space of optical measurement probe 12 to the vertebra to which it couples on the spine. Similarly, there is a direct correlation between the position of target 14 to the vertebra to which it couples on the spine. The dimensions of optical measurement probe 12, target 14, mount 16, mount 17, pedicle screw 28, and pedicle screw 29 are known and stored in remote station 20. Remote station 20 knows the location and trajectory of pedicle screw 28 in the vertebra to which it couples and the location and trajectory of pedicle screw 29 in the vertebra to which it couples. Moreover, remote station 20 has stored angle values such as Cobb angle, endplate to endplate, pedicle screw to endplate, pedicle screw to pedicle screw of the pre-operative spine. All of this is used to produce an accurate image on display 22 of remote station 20 of the spine region of interest in real-time.

Typically, spine surgery results in a change in spine shape. In the example, a rod will be coupled to the pedicle screws in L2-L4. The rod is bent to adjust the curve of the spine in the sagittal plane and the coronal plane. The rod shape can be bent to rotate vertebra. Movement of the spine in the region of interest will result in movement of optical measurement probe 12, target 14, or both. Optical measurement probe 12 has to refocus on target 14 and note differences in the image to the initial image corresponding to the initial spine shape with deformity. Remote station 20 utilizes computer vision, real-time image data from optical measurement probe 12, quantitative measurement data generated from the fluoroscope images, and device dimensions and information related to the system components to translate the movement to changes in spine position that can be viewed on display 22 of remote station 20 in real-time. For example, the surgeon can view changes in the spine shape on display 22 as the spine is manipulated. Not only can the spine shape be viewed, but quantitative measurement data is generated related to the spine shape on display 22 that comprises information such as Cobb angle or vertebral rotation. The quantitative measurement data in conjunction with the surgeon subjective feel related to the spine manipulation can result in changes to the pre-operative plan. A new plan or workflow can then be implemented by the surgeon or by remote station 20. In one embodiment, the new plan is implemented and quantitative measurements are taken to verify the results of the changes.

Figure 6:
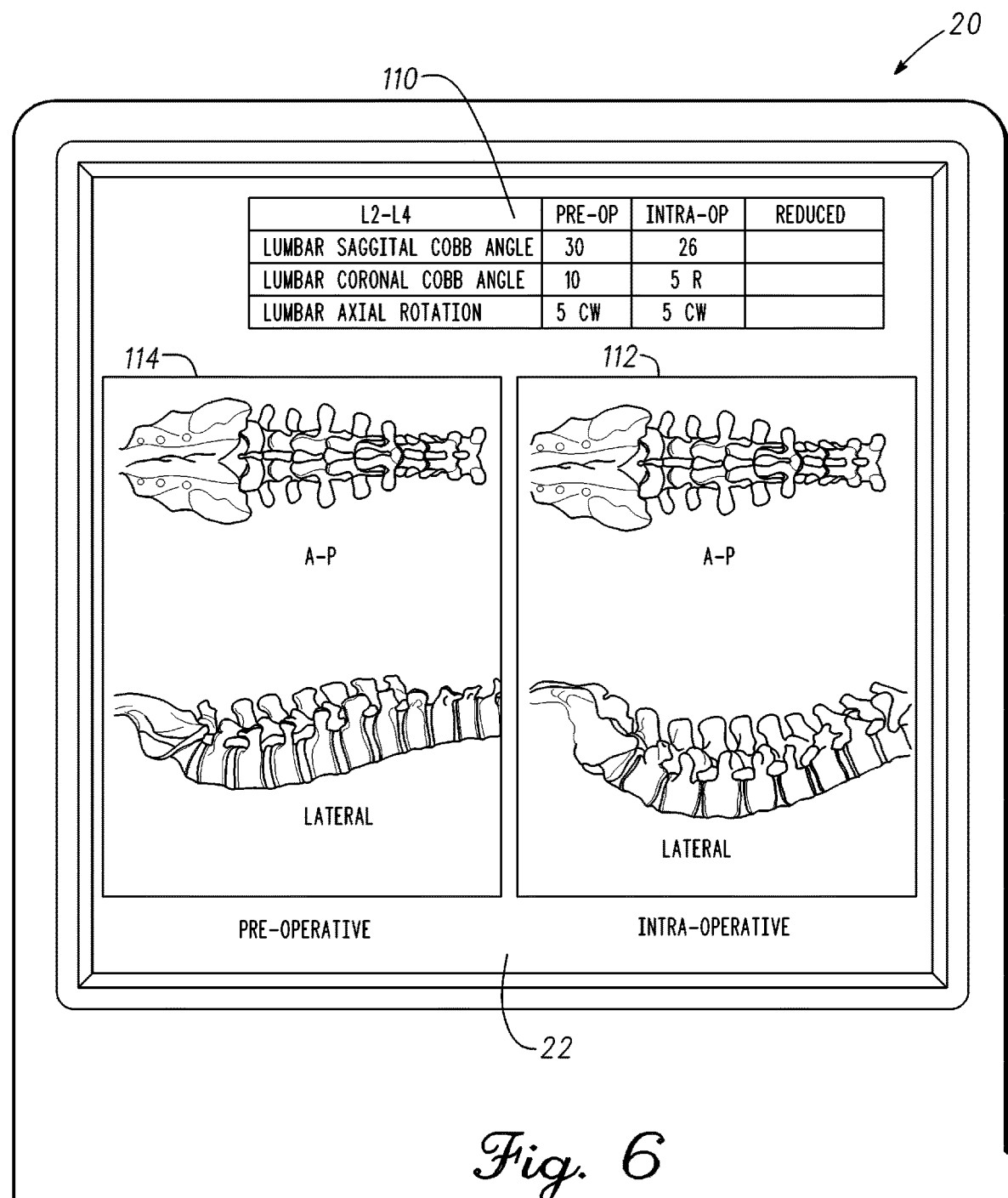
FIG. 6 is an illustration of the display of the remote station in accordance with an example embodiment.

FIG. 6 is an illustration of display 22 of remote station 20 in accordance with an example embodiment. Referring briefly to FIG. 5, the pedicle screws have been placed in the region of interest in the spine. Remote station 20, optical measurement probe 12, and target 14 are coupled to the pedicle screws to provide quantitative measurement data related to the position of vertebra relative to one another. The spine deformity is replicated by remote station 20 from the fluoroscope images and shown on display 22. The spine shape is generated in real-time from quantitative measurement data calculated by remote station 20 using computer vision. Remote station 20 receiving image data from optical measurement probe 12 is configured to calculate the position of each vertebra in relation to others from the targets coupled vertebrae. The spine shape shown in display 22 changes as the spine is manipulated from its initial position in real-time.

Referring back to FIG. 6, a table 110 is shown on display 22 of remote station 20. The table includes a column of pre-operative data and a column of quantitative measurement data. The spine is manipulated by the surgeon. The manipulation is a subjective analysis by the surgeon to determine if the pre-operative plan is practical and if there are any unforeseen issues. In one embodiment, the column of quantitative measurement data corresponds to an outcome for the spine. The spine is manipulated to a shape that the surgeon considers a good outcome for the patient. In the example, the lower lumbar region is of interest. More specifically, the shape of the L2-L4 region of the spine will be modified with a rod coupled to the pedicle screws placed in the L2-L4 vertebrae. As mentioned the spine shape is being measured in real-time. The surgeon can have remote station 20 store a spine shape that he has manipulated the spine into. The stored spine shape will include measurements of all the angles and rotation required to replicate the spine back into this position. In the example, the intra-operative column on table 110 are measurements related to manipulated spine shape that the surgeon believes yields a good outcome.

The pre-operative data of the spine can be compared to the quantitative measurement data generated in the operating room. Both the pre-operative data and the initial intra-operative quantitative measurement data relates to the spine deformity to be corrected. There can be differences between what the surgeon calculated using scan information of the spine and what is measured during surgery. The difference can be due to how the patient was measured or to unforeseen patient disease or severity of disease. For example, the intra-operative measurement data is generated with the patient lying prone on an operating table after ligament releases and facet osteotomies are made while the pre-operative data can be taken with the patient in an upright position. The quantitative measurement data can be used to make adjustments to the pre-operative plan to achieve the desired outcome. Moreover, the quantitative measurement data can provide information that was not included in the pre-operative plan.

Table 110 provides L2-L4 sagittal Cobb angle, coronal Cobb angle, and axial rotation data. More or less information can be provided on table 110 depending on the spine deformity and the type of surgery being performed. In the example, the intra-operative quantitative measurements differ from the pre-operative measurements. For example, the intra-operative sagittal Cobb angle measures 4 degrees less than the pre-operative measurement. Similarly, the coronal Cobb angle measures 5 degrees less than the pre-operative measurement. The axial rotation measured the same for the pre-operative and intra-operative measurements. The surgeon can use this information to make adjustments to the plan and also to redefine the outcome of the spine surgery.

Images 112 of the pre-operative spine can be provided with table 110. Similarly, images 114 of the intra-operative spine measured by spine measurement system 10 can be provided with table 110. An anteroposterior view and a lateral view of the pre-operative spine and intra-operative spine are shown. Images 112 and 114 can be overlayed on each other to highlight differences in the pre-operative spine model and the intra-operative spine model. Alternatively, the pre-operative spine rod and the reduced spine rod could be overlayed on each other to highlight differences. Other features to highlight the spine deformity can be used to allow the surgeon at a glance to understand the information in table 110 as it relates to images 112 and 114.

Figure 7:
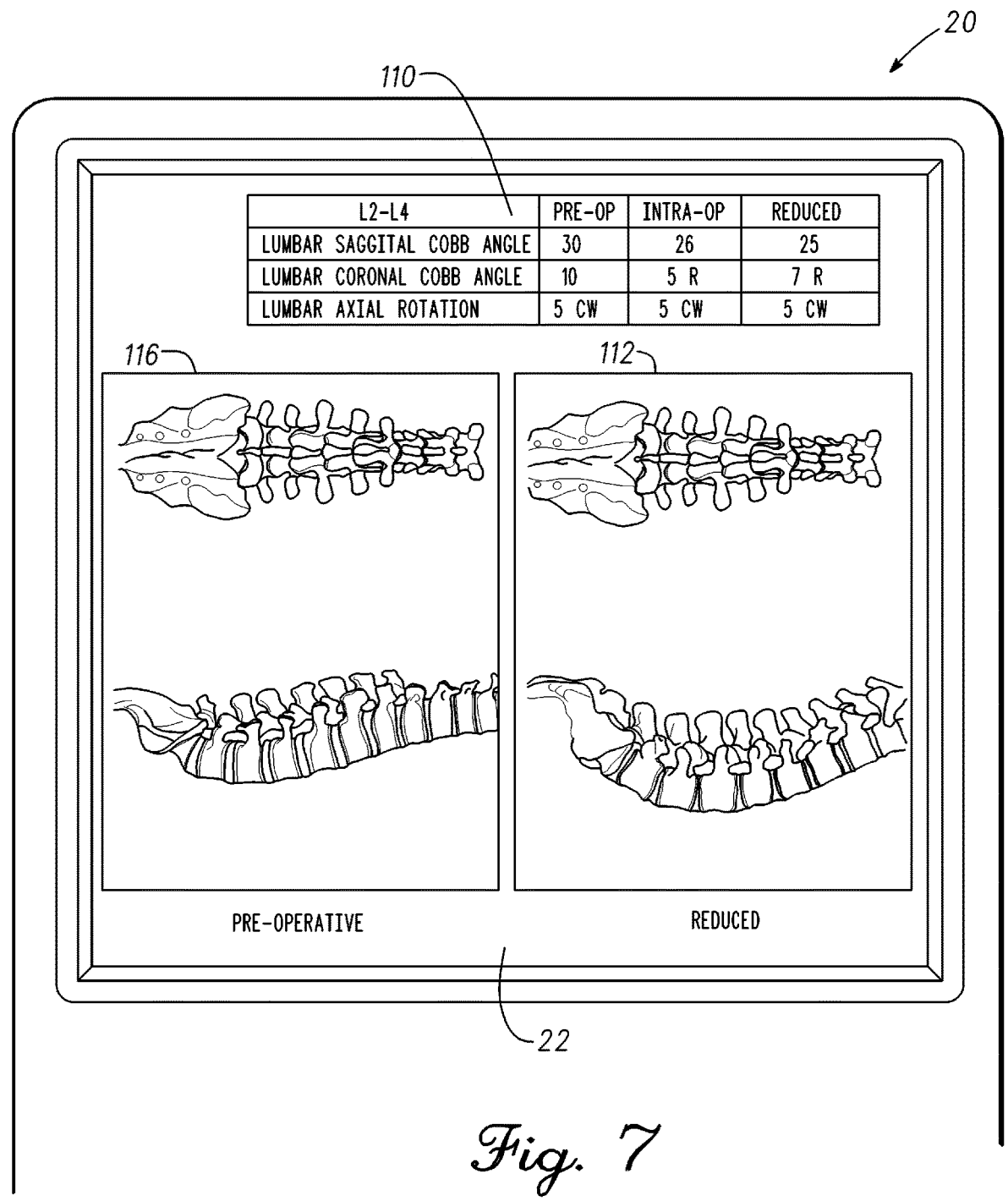
FIG. 7 is an illustration of the display of the remote station in accordance with an example embodiment.

FIG. 7 is an illustration of display 22 of remote station 20 in accordance with an example embodiment. As discussed previously, the surgeon can manipulate the spine to determine if there are issues with implementing the pre-operative plan or intra-operative plan. Computer vision software in remote station 20 identifies a position of each target and translates the target position to a position of a corresponding vertebra. The changes in position are calculated and displayed on display 22. The changes can be displayed in real-time as the spine is manipulated. Typically, the real-time changes will be supported with a quantitative measurement such as sagittal Cobb angle, coronal Cobb angle, and axial rotation. In one embodiment, the surgeon can provide a modified plan based on the intra-operative measurements during surgery. Remote station 20 can provide a surgical workflow and with changes from the pre-operative plan that achieve the desired outcome. For example, remote station 20 can calculate appropriate bends in a rod that couples to pedicle screws to affect a spine shape corresponding to the modified plan.

In the example, a rod has been coupled to the spine. The rod is clamped to the pedicle screws with the one or more targets in place. The rod will have one or more bends that affect vertebral placement in the sagittal and coronal planes. Thus, the spine shape takes a shape of the rod. Computer vision software in remote station 20 measures the spine shape with the rod and targets in place. An anteroposterior view and a lateral view of the reduced spine shape in the L2-L4 region of interest is displayed on the display 22 as images 116. Images 112 corresponding to the pre-operative spine outcome are also shown for comparison. A column is added to table 110 that shows the quantitative measurement of the spine having been "reduced" with the insertion and clamping of the rod to the pedicle screws. As shown, the measured values differ from the pre-operative data and the intra-operative measured data. In particular, the reduced spine shape has a sagittal Cobb angle of 25 degrees, a coronal Cobb angle of 7 (right) degrees, and an axial rotation of 5 degree (clockwise). The surgeon can review the outcome with the rod in place and determine if the changes meet the desired outcome or if changes need to be made.

Remote station 20 can also analyze the outcome and suggest changes to the rod with calculated results related to sagittal Cobb angle, coronal Cobb angle, and axial rotation. In one embodiment, the curvature of the pre-operative plan, intra-operative measurements, and the reduced measurements could be overlayed or displayed separately to show differences in each stage of the operation.

Figure 8A:
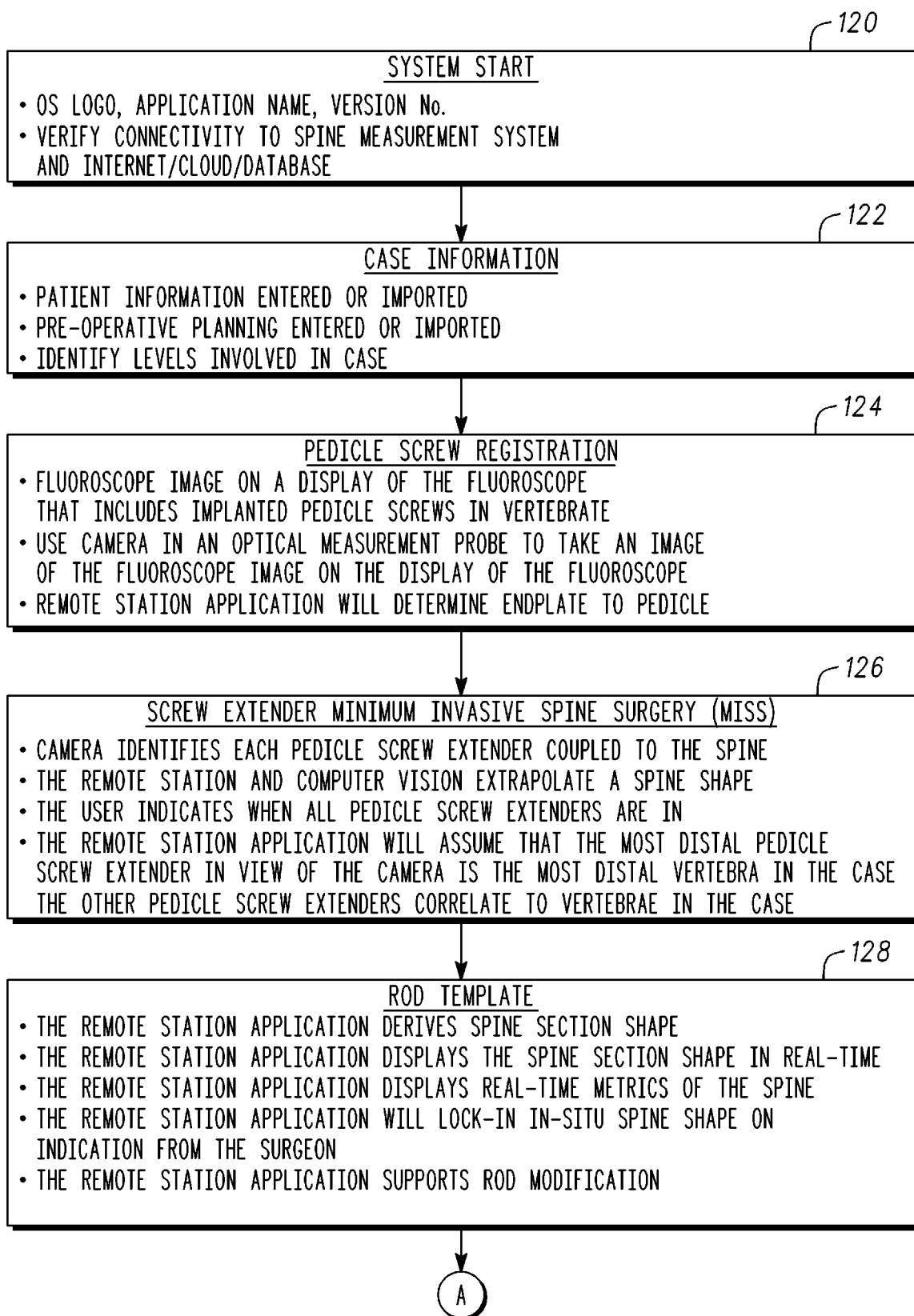
FIG. 8A is block diagram of a method of spine alignment in accordance with an example embodiment.
Figure 8B:
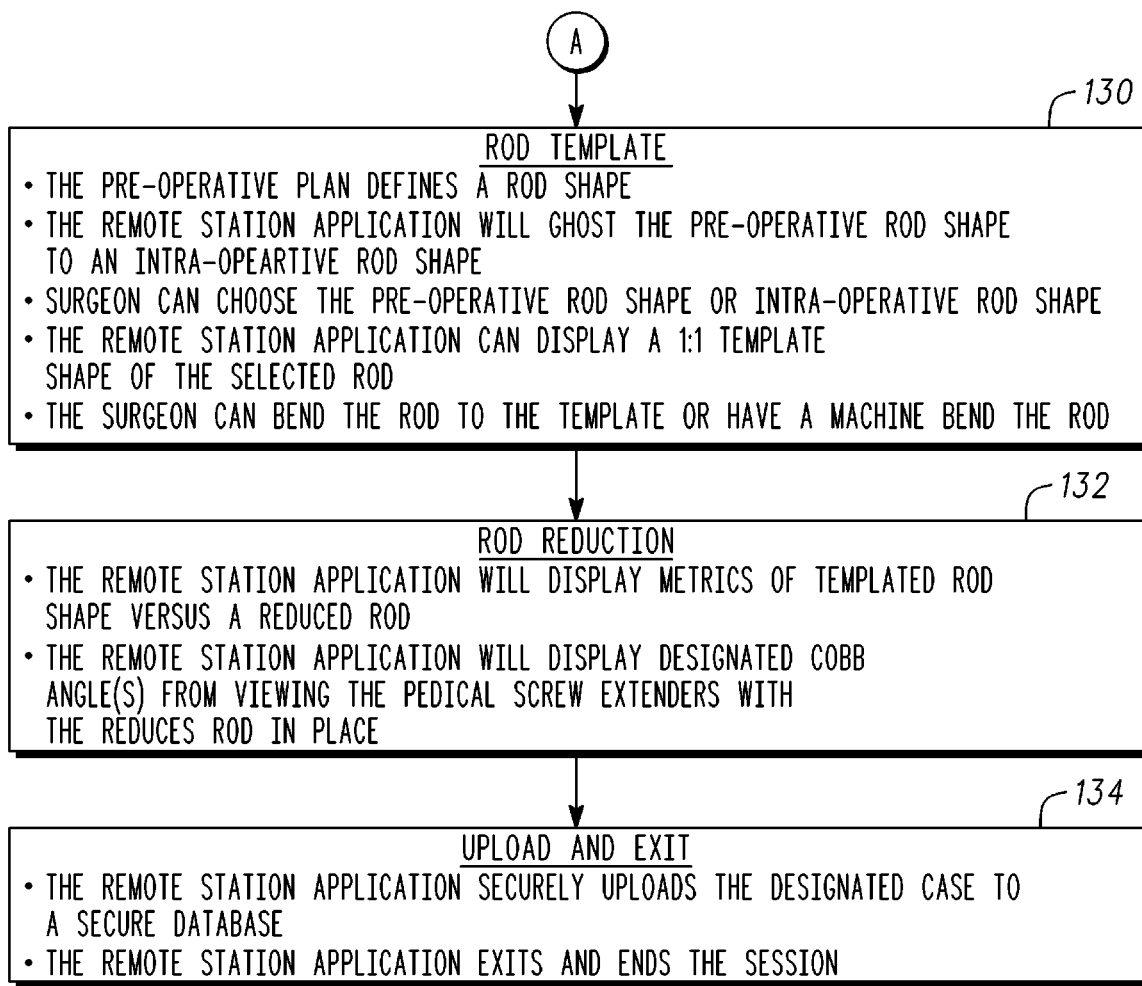
FIG. 8B is a continuation of the block diagram 8A.

FIG. 8 is block diagram 119 of a method of spine alignment in accordance with an example embodiment. A method of spine alignment using a spine measurement system is disclosed. The method can be practiced with more or less steps and is not limited to the order of steps shown. The method is not limited to the spine example but can be used for hip, knee, shoulder, ankle, elbow, spine, hand, wrist, foot, bone, and musculoskeletal system. The components listed in the method can be referred to and are disclosed in FIG. 5. In a step 120, the system is started. As part of the start up process a spine measurement system is turned on. The spine measurement system comprises a remote station, fluoroscope, optical measurement probe, and one or more targets. A logo, application name, and version of the software is displayed on a display of the remote station. In one embodiment, the remote station can be placed outside the sterile zone of an operating room but in a location where the display of the remote station is visible to a surgical team.

In general, the remote station is configured to receive image data from the optical measurement probe. The optical measurement probe includes a camera. The camera can be monocular or binocular. The optical measurement probe is configured to view a position of one or more targets within a field of view of the optical measurement probe. The remote station includes a remote station application that can process image data from the optical measurement probe that generates quantitative measurement data related to spine shape and metrics used for spine surgery. For example, the remote station application can measure a Cobb angle from fluoroscope images of the spine with the remote station application using computer vision.

In a step 122, case information is provided. Patient information can be entered directly into the remote station. Alternatively, patient information can be imported from local storage or through the internet at a remote location. A pre-operative plan for the surgical procedure is entered to the remote station. The pre-operative plan can be imported from local storage or through the internet at a remote location. Also, levels involved in the case are identified. The information can be displayed on the display of the remote station.

In a step 124, the optical measurement probe is used to take an image of a display of the fluoroscope showing a fluoroscope image of the spine. The fluoroscope image can show the pedicle screws placed in the vertebrae. The optical measurement probe can be held in hand to aim the camera at the display of the fluoroscope to take one or more images. The images of the fluoroscope display are sent from the optical measurement probe to the remote station.

The remote station application using computer vision can identify vertebra endplates and pedicle screws from the fluoroscope images. The remote station application can be configured to interpolate a plane trajectory of a vertebra endplate or interpolate a pedicle screw trajectory. An angle is measured between two interpolated trajectories that would extend to intersection. The angle can relate to a measure of spine deformity or spine curvature. In a first embodiment, the remote station application is configured to calculate an angle formed by interpolated plane trajectories of two different vertebra endplates that intersect from the fluoroscope images. In a second embodiment, the remote station application is configured to calculate an angle formed by a plane trajectory of a vertebra endplate and a trajectory of a pedicle screw that intersect from fluoroscope images. In a third embodiment, the remote station application is configured to calculate an angle between two pedicle screw trajectories that intersect from two pedicle screws in two different vertebra from fluoroscope images. In a fourth embodiment, a Cobb angle is displayed on the display of the remote station. The Cobb angle is a measure of an angle between the plane trajectory of a proximal endplate of a proximal vertebra of the spine region of interest and the plane trajectory of the distal endplate of a distal vertebra of the spine region of interest.

The remote station application using computer vision locates features on the fluoroscope images and generates metrics or quantitative measurement data that is related to spine shape. A spine image is created from the metrics and displayed on the display of the remote station. In one embodiment, human interaction is required for verification that the spine image on the display of the remote station is correct. The surgeon can confirm that labeled vertebra of the spine displayed on the display of the remote station correlates to what the surgeon views on the operating room table.

In a step 126, pedicle screw extender's used for minimally invasive spine surgery (MISS) is performed. The pedicle screws have been placed in the spine. The pedicle screw extenders are coupled to pedicle screws in the spine. The pedicle screw extenders extend from the spine and are visible to the surgeon. In one embodiment, the spine, pedicle screws, and pedicle screw extenders are in the field of view of the optical measurement probe.

The optical measurement probe can be coupled to a pedicle screw or a stable surface. One or more targets can be coupled to a pedicle screw using a mount having a predetermined shape. In one embodiment, the pedicle screw extenders are targets of the spine measurement system. A view of the pedicle screws or spine is often obstructed by the hands of the surgeon, tools, or devices coupled to the spine. The pedicle screw extenders allow the surgeon to see a spine shape while manipulating the spine.

The remote station is configured to receive image data from the optical measurement probe when coupled to the spine. The remote station is configured to measure the relative position of each target within the field of view of the optical measurement probe. In one embodiment, the camera in the optical measurement probe views the pedicle screw extenders extending from the spine. The remote station receives images of the pedicle screw extenders in real-time and uses computer vision to identify each individual pedicle screw extender. Moreover, the remote station application uses computer vision to extrapolate positions of each pedicle screw extender back to the vertebra to which it couples thereby relating pedicle screw extender position to vertebra position. The remote station application measures and calculates vertebra position as the spine is manipulated by converting changes in the 2-dimensional image of the pedicle screw extenders viewed by the optical measurement probe into 3-dimension movement of the vertebra coupled to the pedicle screw extenders in real-time. The quantitative measurements are used to change the spine shape in real-time on the display of the remote station from the initial spine shape measured from the fluoroscope images.

The pedicle screw extender surfaces can have one or more images that can be recognized by computer vision software. In one embodiment, the remote station application will assume that the most distal pedicle screw extender in the field of view is also the most distal vertebra in the spine region of interest. The remote station can then correlate each vertebra in the spine region of interest from the most distal vertebra and generate an image with each vertebra labeled on the display of the remote station. The user can also redefine the orientation where the most distal vertebra is the closest vertebra in the field of view. The remote station has fluoroscope data related to pedicle screw position, placement angles, and trajectory and can use this information to support the real-time spine measurement. Similarly, the remote station has dimensions of the pedicle screws and pedicle screw extenders that can be used to extrapolate back to a corresponding vertebra.

In a step 128, a rod template is provided to support shaping a rod. The shape of the spine is measured by the remote station application and displayed on the display of the remote station. The surgeon manipulates the spine to determine a spine shape that meets a desired outcome. The remote station application can calculate metrics and angles related to the spine shape based on the position of the pedicle screw extenders. Thus, the spine shape as it is being manipulated by the surgeon is displayed on the display of the remote station in real-time. In one embodiment, the surgeon can lock-in an in-situ spine shape. For example, the surgeon is manipulating the spine and viewing the spine shape on the display of the remote station with real-time measurements. Once locked-in, the remote station application can calculate metrics and angles related to the in-situ spine shape such as Cobb angle. The remote station can provide a rod template that achieves the in-situ spine shape generated by the surgeon.

In a step 130, a shape of the pre-operative plan rod shape is compared to an intra-operative rod shape determined by quantitative measurement. The quantitative measurement data generated by the remote station can be used by the surgeon to determine the intra-operative rod shape. In one embodiment, the remote station application can calculate rod angles and rod shape to achieve the locked-in spine shape. In another embodiment, the remote station application can display a 1:1 image of a rod that achieves the desired outcome. The surgeon can bend the rod to the rod template displayed on the display of the remote station. Alternatively, a machine can bend the rod using quantitative measurement data provided by the remote station. The pre-operative rod shape can be ghosted or overlayed with the intra-operative rod shape to view differences in each shape with metrics.

The surgeon has a choice of choosing between the different rod shapes. The pre-operative rod shape and intra-operative rod shape can also be applied to the measured intra-operative spine shape in the remote station. The remote station can simulate the spine shape and display the spine shape with either the pre-operative rod shape, the intra-operative rod shape, or both. One or more metrics such as Cobb angle or vertebra rotation can be calculated by the remote station using the pre-operative or intra-operative rod shape and displayed on the remote station. The remote station application can take into account material properties of the rod and the force applied to the rod by the musculoskeletal system to change rod shape to achieve the desired outcome.

In a step 132, the rod is reduced by the surgeon. The surgeon couples the rod to the pedicle screws. The remote station application can calculate Cobb angles from the positions of the pedicle screw extenders with the rod in place. The rod can be modified further if the measured Cobb angles do not achieve the desired outcome.

In a step 134, the information related to spine the surgery can be uploaded. The remote station uploads designated case data to a secure database. The user will exit the remote station and end the session.

Figure 9:
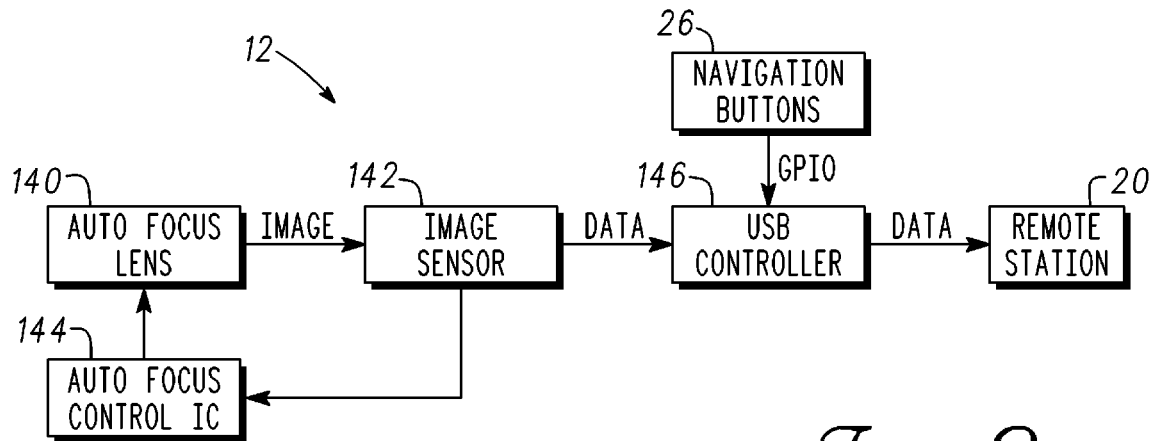
FIG. 9 is block diagram of the optical measurement probe in accordance with an example embodiment.

FIG. 9 is block diagram of optical measurement probe 12 in accordance with an example embodiment. Optical measurement probe 12 and remote station 20 are disclosed in FIG. 1 as components of spine measurement system 10. Optical measurement probe 12 is a high-resolution camera system configured to monitor the musculoskeletal system and more specifically the spine during surgery. The camera can be monocular. Optical measurement probe 12 is coupled to a remote station using computer vision to generate quantitative measurement data to support spine surgery. In one embodiment, optical measurement probe 12 is used a single time and disposed of after a surgery has been completed.

An auto-focus lens 140 couples to an image sensor 142. Image sensor 142 couples to auto focus control IC 144 to provide input that is used to control auto-focus lens 140. Auto-focus lens 140, image sensor 142, and auto focus control IC 144 form a feedback path that provides a focused image to image sensor 142 that is within a field of view of optical measurement probe 12. Image sensor 142 receives light through auto-focus lens 140 and converts the light to a digital representation of the light pattern received. Image sensor 142 couples the digital image data to USB controller 146. USB controller 146 is an interface for coupling image data to remote station 10. Remote station 10 can then analyze the image data using the remote station application and computer vision software to generate quantitative measurement data.

Switch 26 couples to USB controller 146. Switch 26 couples to a general purpose input/output (GPIO) of USB controller 146. In one embodiment, switch 26 is a three-position switch for navigating a user interface on remote station 20. USB controller 146 couples a signal from the switch to remote station 20. This allows the surgeon in the sterile field of the operating room to navigate and make selections on a display of remote station 20. In one embodiment, switch 26 on optical measurement probe 12 can perform up, down, and select functions. USB controller 146 can sense a switch closure from switch 26 and send a code to remote station 20. Remote station 20 can then interpret the code and move or select the active field in the display to complete the command.

Figure 10:
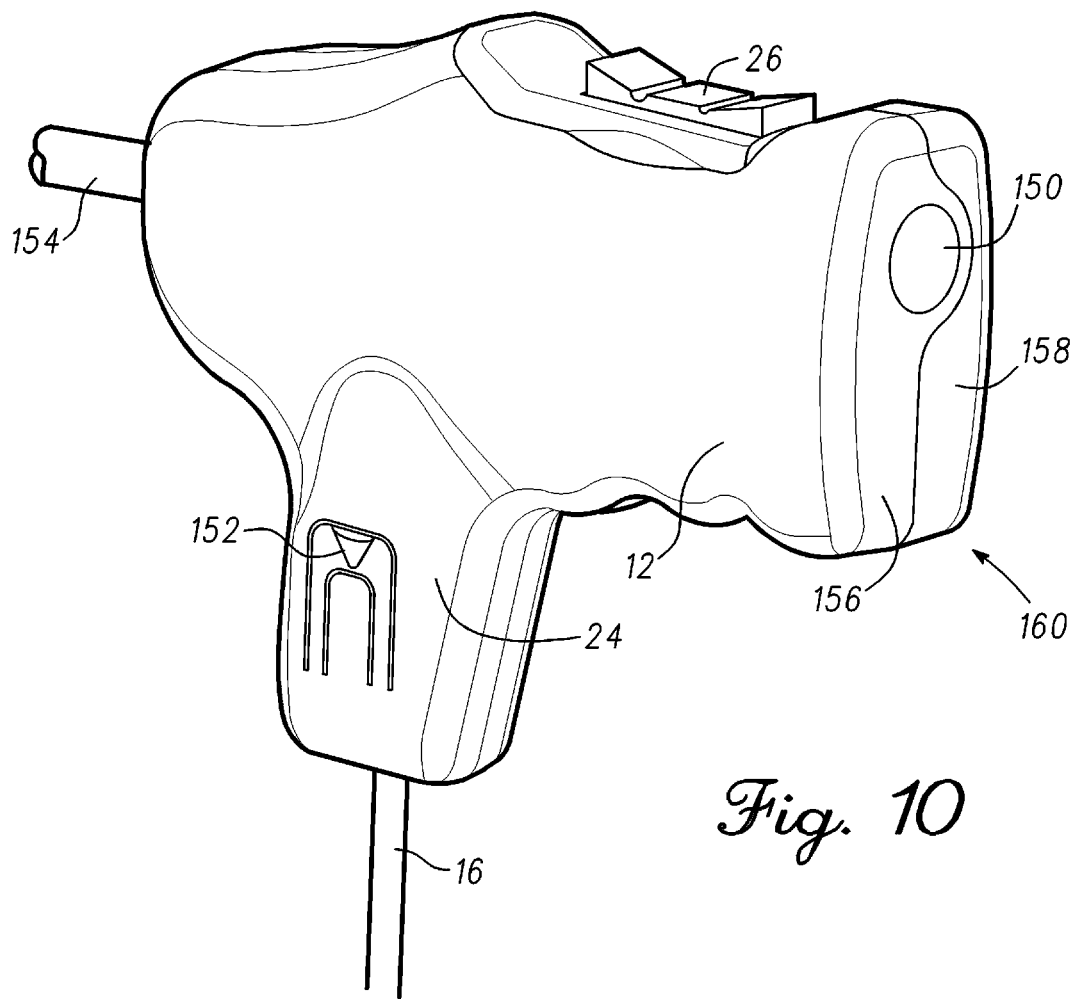
FIG. 10 is an illustration of the optical measurement probe in accordance with an example embodiment.

FIG. 10 is an illustration of optical measurement probe 12 in accordance with an example embodiment. Optical measurement probe 12 includes a camera for providing images of a spine to support generation of quantitative measurement data used during surgery. The camera further supports measurement of spine alignment and relative position of vertebra in real-time during surgery. In one embodiment, optical measurement probe 12 is used for a single surgery and disposed of in an appropriate manner after the surgery has been completed.

An enclosure 160 of optical measurement probe 12 comprises a molded structure 156 and a molded structure 158. Molded structures 156 and 158 comprise a polymer material that includes structural ribbing to increase strength of enclosure 160 when coupled together. In one embodiment, molded structures comprise polycarbonate that can reliably and repeatedly be formed to meet standards required in the medical device field. Molded structures 156 and 158 are coupled together to form a housing for the camera and electronic circuitry. The electronic circuitry is coupled to the camera within the housing. In one embodiment, the electronic circuitry supports focus control, imaging, data transfer, and system control. In one embodiment, enclosure 160 includes a first compartment that houses the electronic circuitry and camera and a second compartment that couples to mount 16. The first compartment is sealed to prevent solids, liquids, and gases from entering or leaving the first compartment. The second compartment does not have to be sealed. Optical measurement probe 12 is sterilized and placed in sterile packaging to prevent contamination before use.

A lens cover 150 couples to enclosure 160. Lens cover 150 is sealed to molded structures 156 and 158. In one embodiment, lens cover 150 is transmissive and distortion free to light and acts as a barrier to protect an auto-focus lens of the camera from an external environment. Lens cover 150 can have refractive qualities and work in conjunction with the auto-focus lens to provide better imaging.

Switch 26 couples to enclosure 160. Switch 26 is sealed to molded structures 156 and 158. In one embodiment, switch 26 is a rocker switch having three positions. Switch 26 is used to control a user interface on a remote station while the surgeon is in a surgical field. For example, switch 26 can allow the user to move up, move down, or select fields shown on a display of the remote station. For example, the user interface can be used to verify that the computer vision software on the remote station identified a vertebra or vertebrae of the spine correctly. In one embodiment, image data or control signals from optical measurement probe 12 are coupled to the remote station via a wired connection. Cable 154 couples to enclosure 160. Cable 154 is sealed to molded structures 156 and 158. For example, a grommet can be used to form a seal between cable 154 and enclosure 160. Silicone sealant could be used to further seal an interface between the cable, grommet, and enclosure. Alternatively, the electronic circuitry can include a transceiver. Optical measurement probe 12 could then transmit image data and control signals wirelessly to the remote station.

Optical measurement probe 12 includes handle 24. Handle 24 allows a user to hold optical measurement probe 12 in a hand and direct the device to take images. In one embodiment, optical measurement probe 12 is held by the surgeon to take an image of a display of a fluoroscope. The display of the fluoroscope has a fluoroscope image that is captured by optical measurement probe 12. The fluoroscope image is provided to the remote station to generate quantitative measurement data that is used during the surgery. In a second embodiment, optical measurement probe 12 can be coupled to the musculoskeletal system or to a stable surface of the operating room. For example, mount 16 can couple optical measurement probe 12 to a pedicle screw placed in a vertebra. Enclosure 160 includes a release 152 to decouple mount 16 from optical measurement probe 12. Depressing release 152 releases mount 16 from a retaining feature allowing optical measurement probe to be removed from mount 16.

Figure 11:
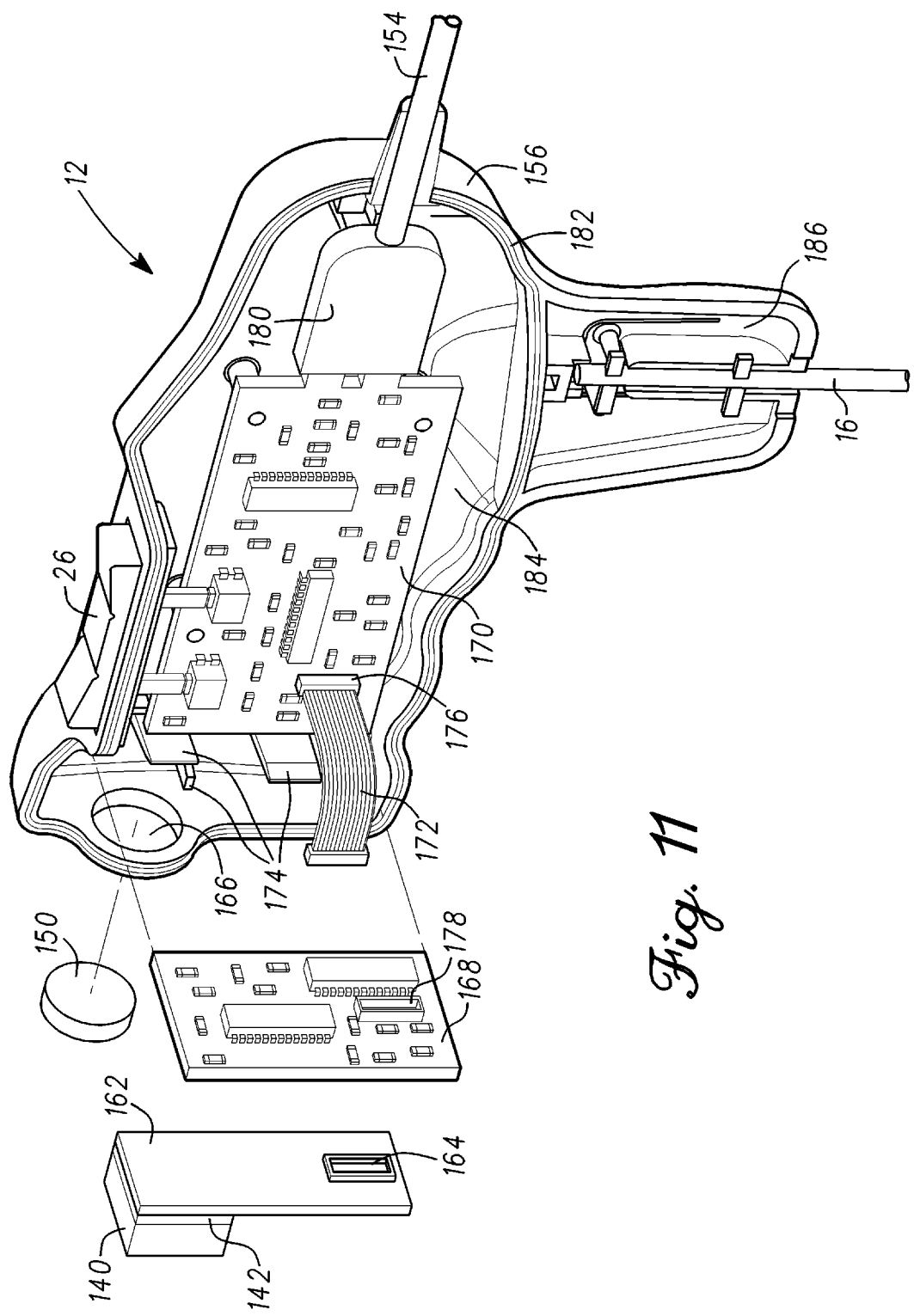
FIG. 11 illustrates component layout within the optical measurement probe in accordance with an example embodiment.

FIG. 11 illustrates component layout within optical measurement probe 12 in accordance with an example embodiment. Optical measurement probe 12 comprises lens cover 150, camera 162, a printed circuit board 168, a printed circuit board 170, switch 26, and cable 154. In general, electronic circuitry is coupled to camera 162 to control and transmit image data. Electronic components are mounted on printed circuit board 168 and printed circuit board 170. Printed circuit boards 168 and 170 include interconnect to couple the mounted electronic components to form circuits.

Camera 162 comprises auto-focus lens 140, image sensor 142, and a connector 164. The components of camera 162 can be mounted on a printed circuit board. Connector 164 of camera 162 couples to a corresponding connector on printed circuit board 168. Connector 164 places camera 162 in a predetermined position relative to opening 166. In one embodiment, printed circuit board 168 comprises auto-focus control integrated circuit of FIG. 9.

Molded structure 156 forms a compartment 184 and a compartment 186 when coupled to molded structure 158 of FIG. 10. Camera 162 and the electronic circuitry are housed in compartment 184 and sealed from the external environment. The electronic circuitry comprises printed circuit boards 168 and 170. Printed circuit boards 168 and 170 can include auto-focus control integrated circuit 144 and USB controller 146 of FIG. 9.

Figure 12:
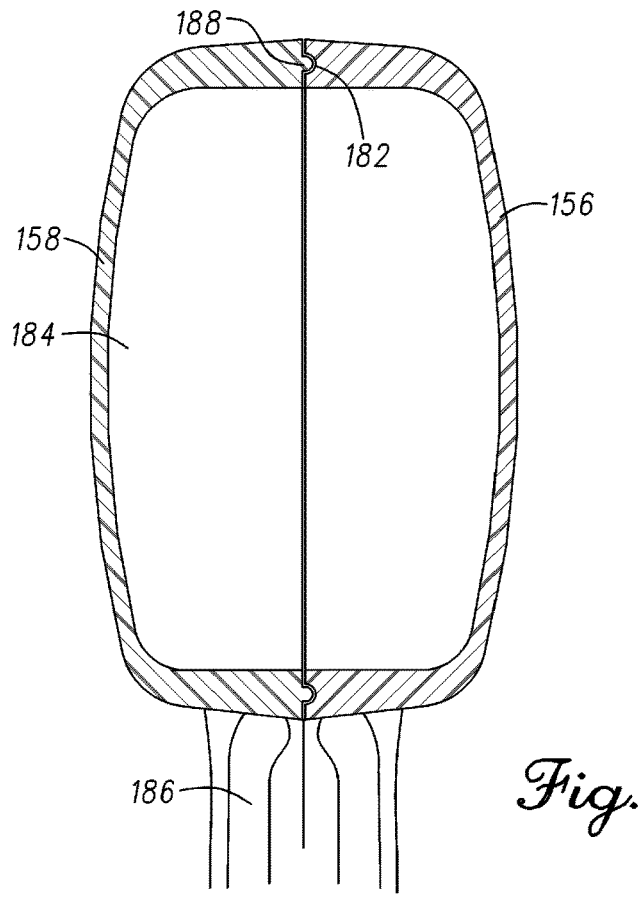
FIG. 12 is an illustration of a sealed compartment of the optical measurement probe in accordance with an example embodiment.

A glue channel 182 is formed on a surface of molded structure 156 that mates with a corresponding surface of molded structure 158 of FIG. 10. In one embodiment, glue channel 182 is a groove formed on the surface of molded structure 156. The groove can hold glue while coupling molded structure 156 to molded structure 158 of FIG. 10. Referring briefly to FIG. 12, a cross-sectional view of molded structures 156 and 158 are illustrated coupled together. A compartment 184 is sealed to isolate the electronic circuitry and camera 162 from an external environment. The corresponding surface of molded structure 158 can include a tongue 188 that fits in glue channel 182. Tongue 188 provides more surface area for the glue to adhere to and supports sealing molded structures 156 and 158 from the external environment.

Referring back to FIG. 11, compartment 186 is not sealed from an external environment. In one embodiment, compartment 186 is a handle that when held in hand can be used to direct optical measurement probe 12. Compartment 186 has an opening to receive mount 16. Mount 16 couples optical measurement probe 12 to the muscular-skeletal system or another surface. In one embodiment, mount 16 couples optical measurement probe 12 to a pedicle screw. Compartment 186 includes one or more features to retain and release mount 16.

Figure 13:
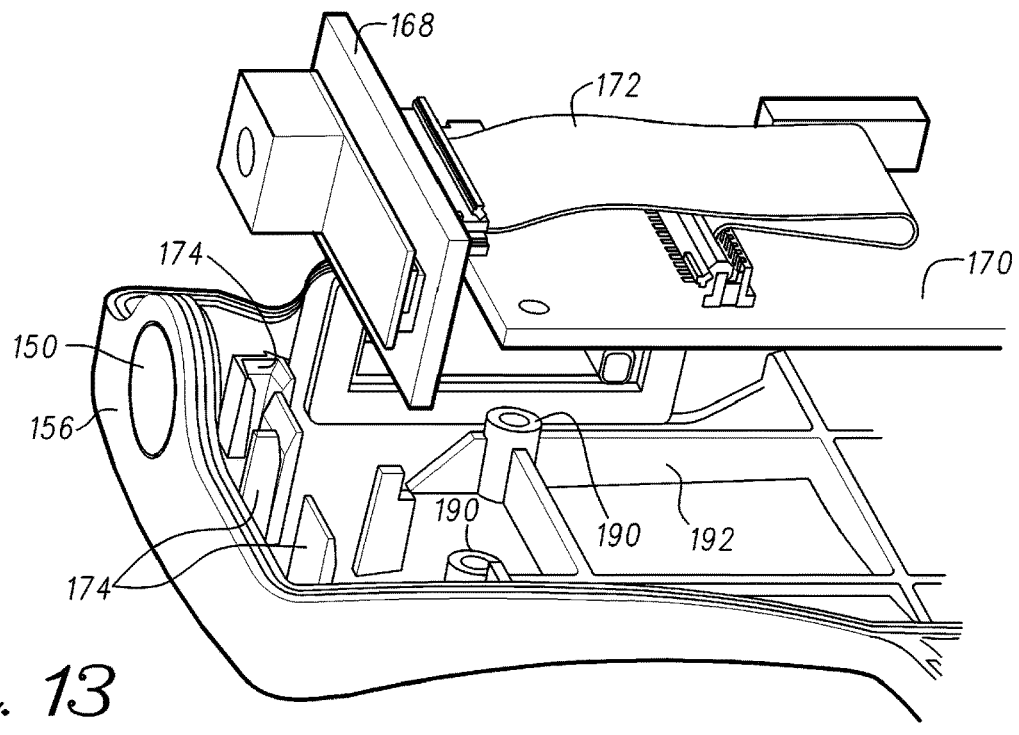
FIG. 13 illustrates the camera and electronic circuitry coupled together in accordance with an example embodiment.

In one embodiment, electronic circuitry and camera 162 are coupled to molded structure 156. Lens cover 150 is placed in opening 164 of molded structure 156. One or more retention structures can hold lens cover 150 in a predetermined position and seal lens cover 150 to molded structure 156. In one embodiment, a cynacrolate adhesive is applied to lens cover 150 and molded structure 156. The cynacrolate will seal and attach lens cover 150 to molded structure 156 within opening 164. Retaining features 174 support and retain printed circuit board 168 to molded structure 156. Referring briefly to FIG. 13, retaining features 174 retain printed circuit board 168 and camera 162 in a fixed position relative to lens cover 150. In one embodiment, retaining features 174 align auto-focus lens 140 and image sensor 142 to lens cover 150 by placing printed circuit board 168 in a predetermined position. Printed circuit board 168 is slotted between retaining features 174. In general, retaining features prevent movement in the vertical and horizontal directions. Retaining features 174 can flex allowing an interference fit to prevent movement. Retaining features 174 can include a locking mechanism that overlies an edge of printed circuit board 168 when a distal edge of printed circuit board 168 is adjacent to an interior surface of molded structure 156. Printed circuit board 168 can be released by bending retaining features 174 away the proximal edge and removing printed circuit board 168.

Referring back to FIG. 11, printed circuit board 170 is mounted to molded structure 156. Printed circuit board 170 is mounted at a 90-degree angle to printed circuit board 168. A flexible interconnect 172 couples the electronic circuitry of printed circuit board 168 to the electronic circuitry of printed circuit board 170. In particular, flexible interconnect couples to a connector 178 on printed circuit board 168 to a connector 176 on printed circuit board 170. Referring briefly to FIG. 13, molded structure 156 includes standoffs 190 that locate printed circuit board 170 in a predetermined position. Printed circuit board 170 can be coupled to standoffs 190 by screws or other fastening means. Structural ribbing 192 is formed in conjunction with standoffs 190. In one embodiment, structural ribbing 192 comprises standoffs 190 and walls formed perpendicular to an interior surface of molded structure 156. Structural ribbing 192 increases the structural integrity of optical measurement probe 12.

Referring back to FIG. 11, printed circuit board 168 couples to printed circuit board 170 through flexible interconnect 178 to support the transfer of image data from camera 162 to a remote station located a distance from optical measurement probe 12. In one embodiment, a USB controller 146 of FIG. 9 is included on printed circuit board 170 to support transfer of the image data from camera 162 and control signals from switch 26. In general, the predetermined position of printed circuit board 170 corresponds to a position of switch 26 and cable 154. Switch 26 aligns to and couples to printed circuit board 170. In one embodiment, switch 26 couples to actuators mounted on printed circuit board 170 for providing control signals. Cable 154 terminates in a connector 180 that couples to a connector mounted on printed circuit board 170. Cable 154 couples to and aligns with printed circuit board 170 to affix the connector of cable 154 to the connector on printed circuit board 170. One or more retaining features prevent the connectors from disengaging and allows cable 154 to directly exit optical measurement probe 12. Furthermore, the one or more retaining features can include a strain relief to hold cable 154 in place. The distal end of cable 154 also terminates in a connector. Cable 154 has sufficient length to couple optical measurement probe 12 to the remote station to provide control signals and image data. Alternatively, printed circuit board 170 can include a transceiver to wirelessly transmit control signals, transmit image data, or receive information.

Figure 14:
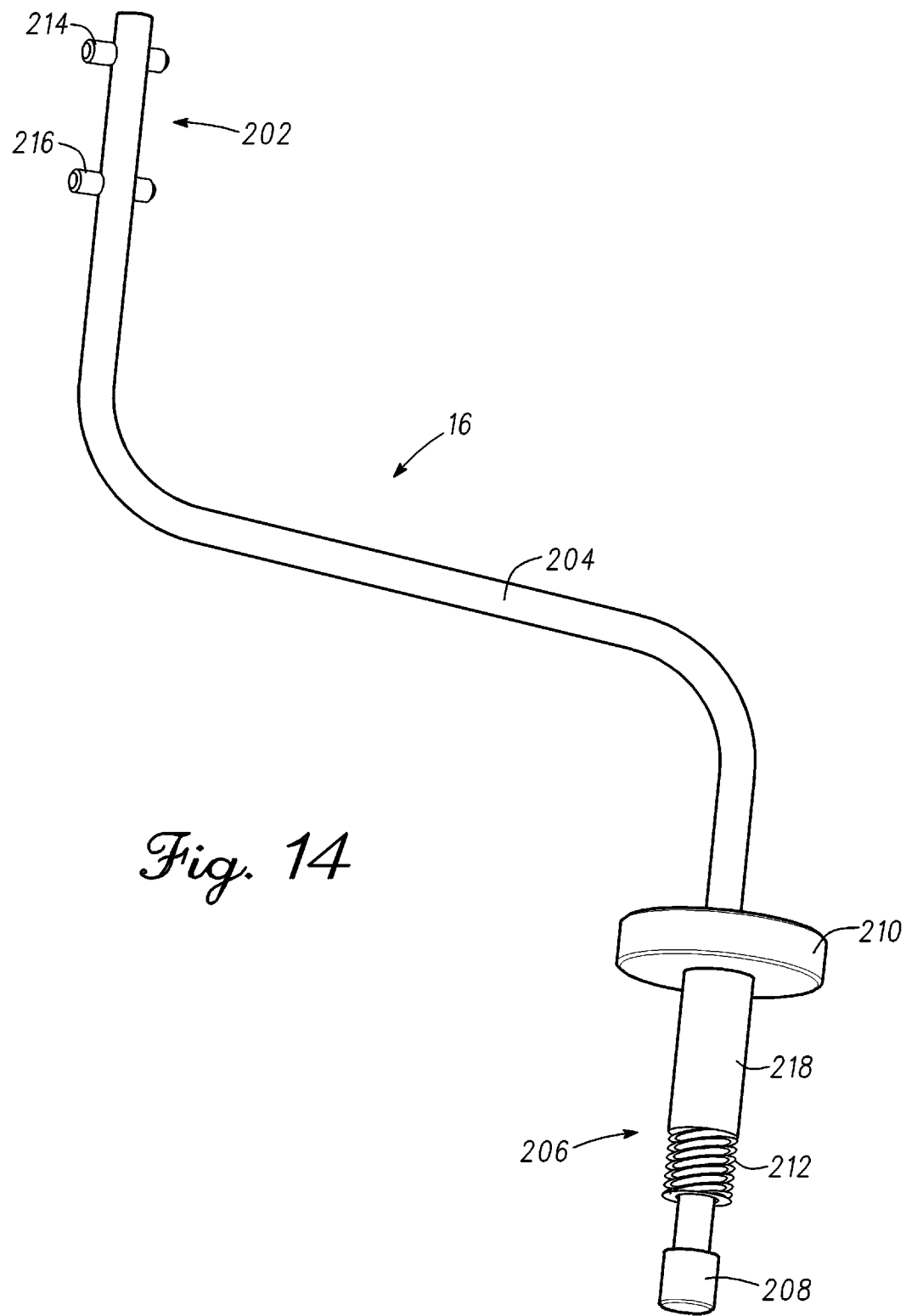
FIG. 14 is an illustration of the mount in accordance with an example embodiment.

FIG. 14 is an illustration of mount 16 in accordance with an example embodiment. Mount 16 comprises a proximal end coupling 202, a shaft 204, and a distal end coupling 206. In general, mount 16 mounts a device to patient anatomy or a stable surface within an operating room. Mount 16 maintains a known geometric or spatial relationship between the device and the object to which it couples. In one embodiment, the relationship between the device and object is fixed and does not change throughout the surgery. Moreover, the dimensions and shape of mount 16 is known and provided to remote station 20. In the example, mount 16 may be used interchangeably with mount 17 of FIG. 5 as both are used to couple a device such as an optical measurement probe or target to the spine or a surface and each operates similarly. Referring briefly to FIG. 5, pedicle screw 29 is coupled to a vertebra of the spine. Mount 17 is used to couple target 14 to pedicle screw 29. The positional relationship between target 14 and pedicle screw 29 is fixed by the predetermined shape and dimensions of mount 17. Similarly, the positional relationship between optical measurement probe 12 and pedicle screw 28 is also fixed by the predetermined shape and dimensions of mount 16. Also, information related to the pedicle screw dimensions and pedicle screw placement within the vertebra is known and stored in remote station 20. Thus, a movement of target 14 can be extrapolated to movement of the vertebra to which it is coupled using the remote station application and computer vision.

Referring back to FIG. 14, proximal end coupling comprises a crossbar 214 and a crossbar 216. Crossbars 214 and 216 couple to a device or target. In one embodiment, retaining features couple to shaft 204, crossbar 214, and crossbar 216 to rigidly hold the device to mount 16. The retaining features can be releasable whereby the mount 16 can be decoupled from the retaining features. Shaft 204 has a predetermined shape. In one embodiment, the shape of shaft 204 supports placement of the device away from where distal end coupling 206 attaches. Furthermore, shaft 204 can have one or more bends to support locating the device in a predetermined position. As mentioned distal end coupling 206 couples to patient anatomy or a fixed surface. In the example, distal end coupling 206 couples to a pedicle screw. Distal end coupling comprises a sleeve 218 that overlies shaft 204. A thumbwheel 210 couples to sleeve 218 to provide a finger grip to rotate sleeve 218. Sleeve 218 further includes a threaded portion 212. In one embodiment, threaded portion 212 is on an exterior of sleeve 218. A base 208 terminates a distal end of shaft 204. Base 208 of mount 16 fits into an internal feature of the pedicle screw and creates a locked, collinear construction. In one embodiment, base 208 is cylindrical in shape. Base 208 has a larger diameter than shaft 204. Base 208 and crossbar 216 retains sleeve 218 on shaft 204.

In the example, mount 16 couples to a pedicle screw. A pedicle screw is designed to retain and hold a rod to that forcibly changes a contour of a spine. The head of the pedicle screw is built up having a region to retain the rod to the pedicle screw. Typically, the head of the pedicle screw includes an interior threaded cavity. The rod is placed in the head and a set screw is coupled to the interior threaded cavity to clamp down on the rod. Distal end coupling 206 couples to the interior threaded cavity of a head of a pedicle screw. Distal end coupling 206 can be used to hold down a rod to the head of the pedicle screw or fasten to the pedicle screw without the rod in place. For example, threaded portion 212 engages with the interior threaded cavity of the pedicle screw. Thumb wheel 210 is rotated until base 208 couples to a surface of the pedicle screw. Further tightening of distal end coupling 206 applies a force from sleeve 218 to base 208 and the surface of the pedicle screw. Thus, sleeve 218 clamps base 208 to the surface of the pedicle screw. Distal end coupling 206 can be fastened to the pedicle screw whereby shaft 206 cannot move or rotate. Thus, the device coupled to proximal end coupling 202 is fixed in place to the pedicle screw. Movement of the vertebra and pedicle screw results in a corresponding movement of the device.

Figure 15:
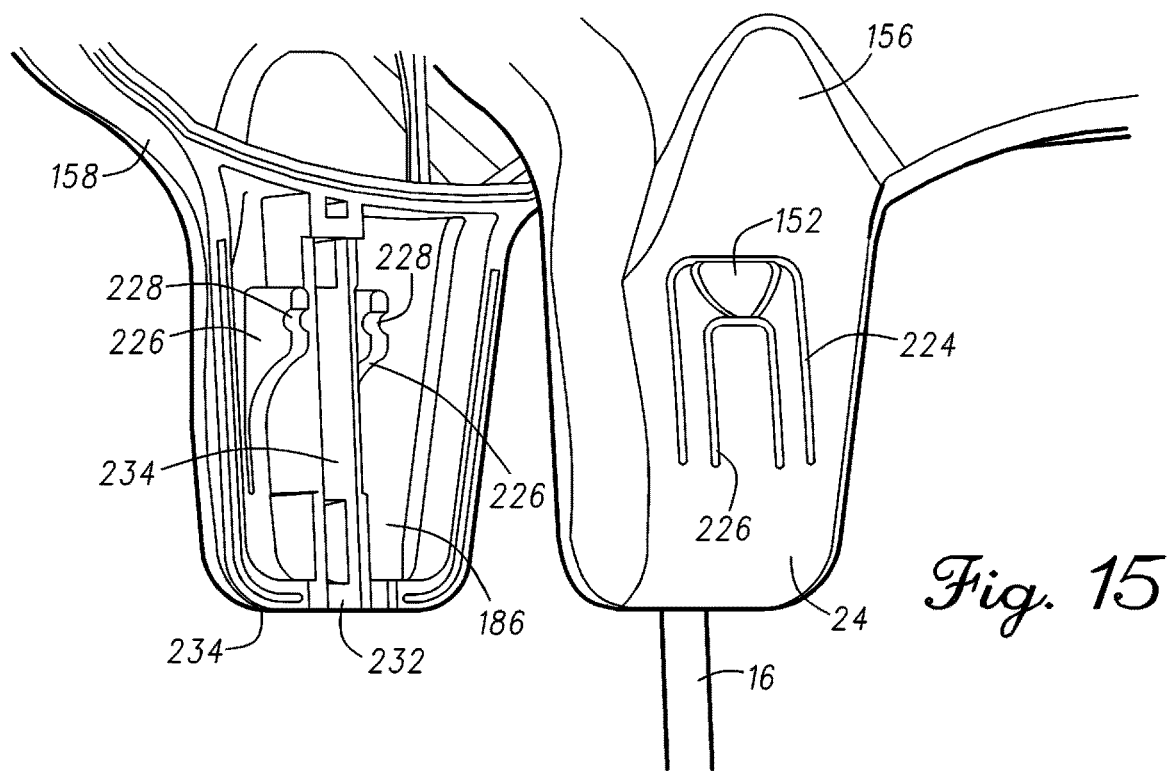
FIG. 15 is a partial view of the enclosure of the optical measurement probe illustrating release features in accordance with an example embodiment.

FIG. 15 is a partial view of molded structure 156 and molded structure 158 illustrating release features in accordance with an example embodiment. The partial view shows components that form handle 24 of FIG. 10. Handle 24 of FIG. 10 allows optical measurement probe 12 of FIG. 10 to be held in hand and directed to take one or more images. Mount 16 is retained in compartment 186 of handle 24. Compartment 186 includes a portion of opening 232 for receiving mount 16 into handle 24 and retaining features for holding and releasing mount 16.

The partial view shows an exterior view of handle 24 of molded structure 156 and an interior view of handle 24 of molded structure 158. The exterior view of handle 24 of molded structure 156 includes a slot 224 and a slot 226. Slot 224 and slot 226 are patterned openings formed through molded structure 156. Slot 224 and slot 226 are patterned in handle 24 to form a release mechanism 152 that when pressed supports movement of mount 16. Slot 224 and slot 226 form a flexing region in handle 24 that moves inward when pressed. Release mechanism 152 includes a raised region that can be easily pressed by a thumb or finger.

The interior view of handle 24 of molded structure 158 comprises retaining features 226, cradle 234, and a portion of opening 232. Opening 232 is formed when molded structures 156 and 158 are coupled together. Mount 16 is inserted through opening 232. Cradle 234 has a curved surface for receiving mount 16. Cradle 234 guides mount 16 into compartment 186 when inserted through opening 232. Retaining features 226 are formed on either side of cradle 234. Retaining features 226 provide a spring force to retain mount 16 when mount 16 is inserted into compartment 186. Curved surfaces 228 couple to mount 16 and are retained by a force applied by retaining features 226 applied to curved surfaces 228 on mount 16.

Figure 16:
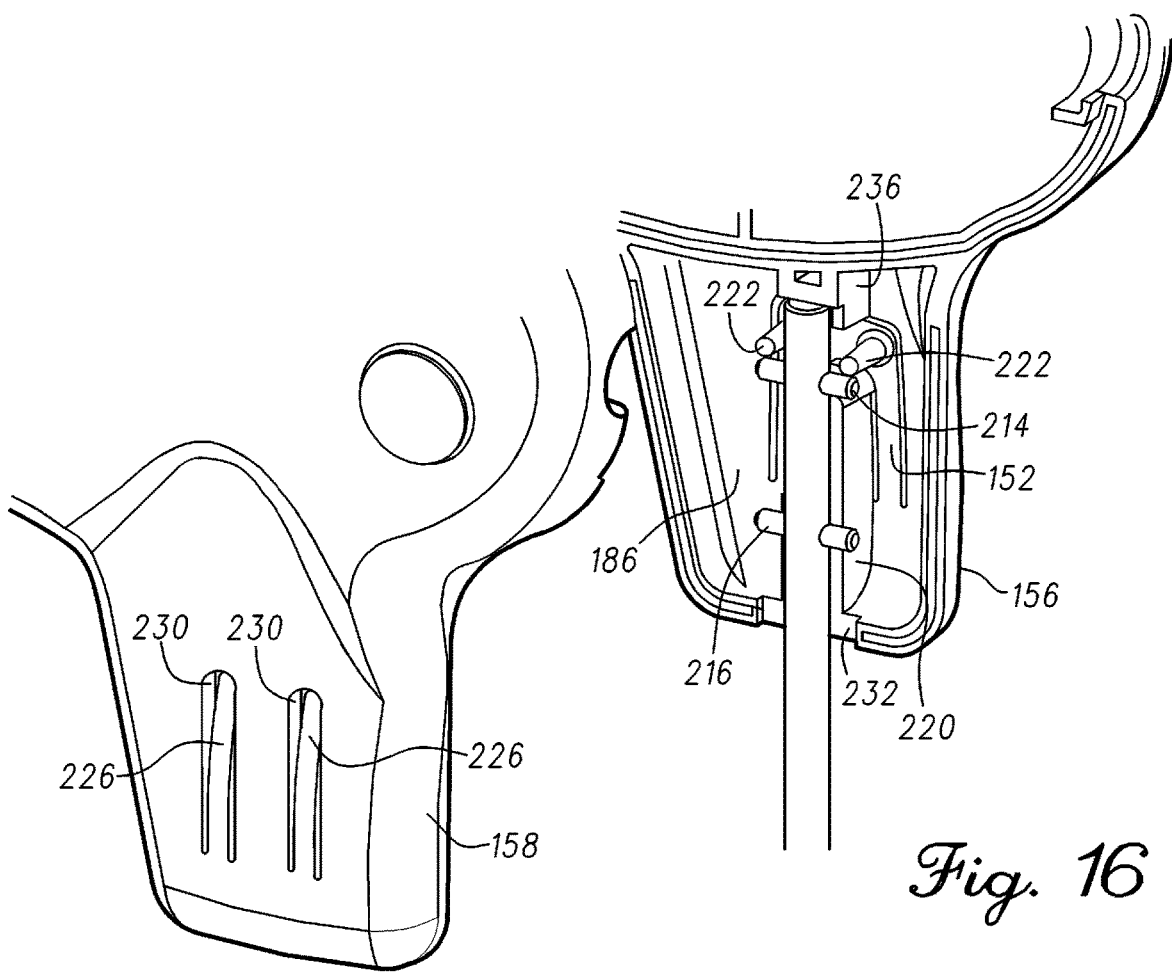
FIG. 16 is a partial view of the enclosure of the optical measurement probe illustrating release features in accordance with an example embodiment.

FIG. 16 is a partial view of molded structure 156 and molded structure 158 illustrating release features in accordance with an example embodiment. The partial view shows an exterior view of handle 24 of molded structure 158 and an interior view of molded structure 156. The exterior view of molded structure 158 includes patterned slots 230 formed through handle 24. Slots 230 are patterned to allow movement of retaining features 226. In one embodiment, retaining features 226 are molded having a curved lever arm that extends into compartment 186 to provide the spring force to retain mount 16.

The interior view of handle 24 of molded structure 156 includes cradle 220, posts 222, and a portion of opening 232. Mount 16 is inserted through opening 232. Cradle 220 has a curved surface for receiving mount 16. Cradle 220 guides mount 16 into compartment 186 when inserted through opening 232. Mount 16 is prevented from going further than a stop 236 in compartment 186. Mount 16 includes a crossbar 214 and a crossbar 216 to support retention of mount 16 in handle 24. Referring briefly to FIG. 15, inserting mount 16 will engage crossbar 214 to retaining features 226. In particular, curved surfaces 228 will engage with the curved surface of crossbar 214 to hold mount 16 in place. Retaining features can also engage crossbar 216. As disclosed, retaining features 226 have a spring force that forcibly engages curved surfaces 228 to the curved surfaces of crossbar 214 whereby mount 16 is held in place.

Referring back to FIG. 16, mount 16 can be released from handle 24. Posts 222 align with crossbar 214. Posts 214 couple to release mechanism 152. Pressing release mechanism 152 pushes posts 222 into crossbar 214 moving mount 16 away from cradle 220. As mount 16 moves away from cradle 220 retaining features 226 are moved towards cradle 234. Alternatively, posts 222 can push into surfaces on features 226 above cradle 220. In this embodiment, cradle 220 expands retaining crossbar 214 and releasing mount 16. As noted, retaining features 226 are flexible having slots 230 to support movement. Mount 16 can be removed when curved surfaces 228 disengage from curved surfaces of crossbar 214. Retaining features 226 continue to move towards cradle 234 until curved surfaces 228 fall below cradle 234 wherein crossbar 214 is no longer engaged by retaining features 226. Mount 16 can then be pulled out through opening 232 to release optical measurement probe 12. Target 14 of FIG. 5 can also include retaining and release features to couple to mount 17 as disclosed herein.

Figure 17A:
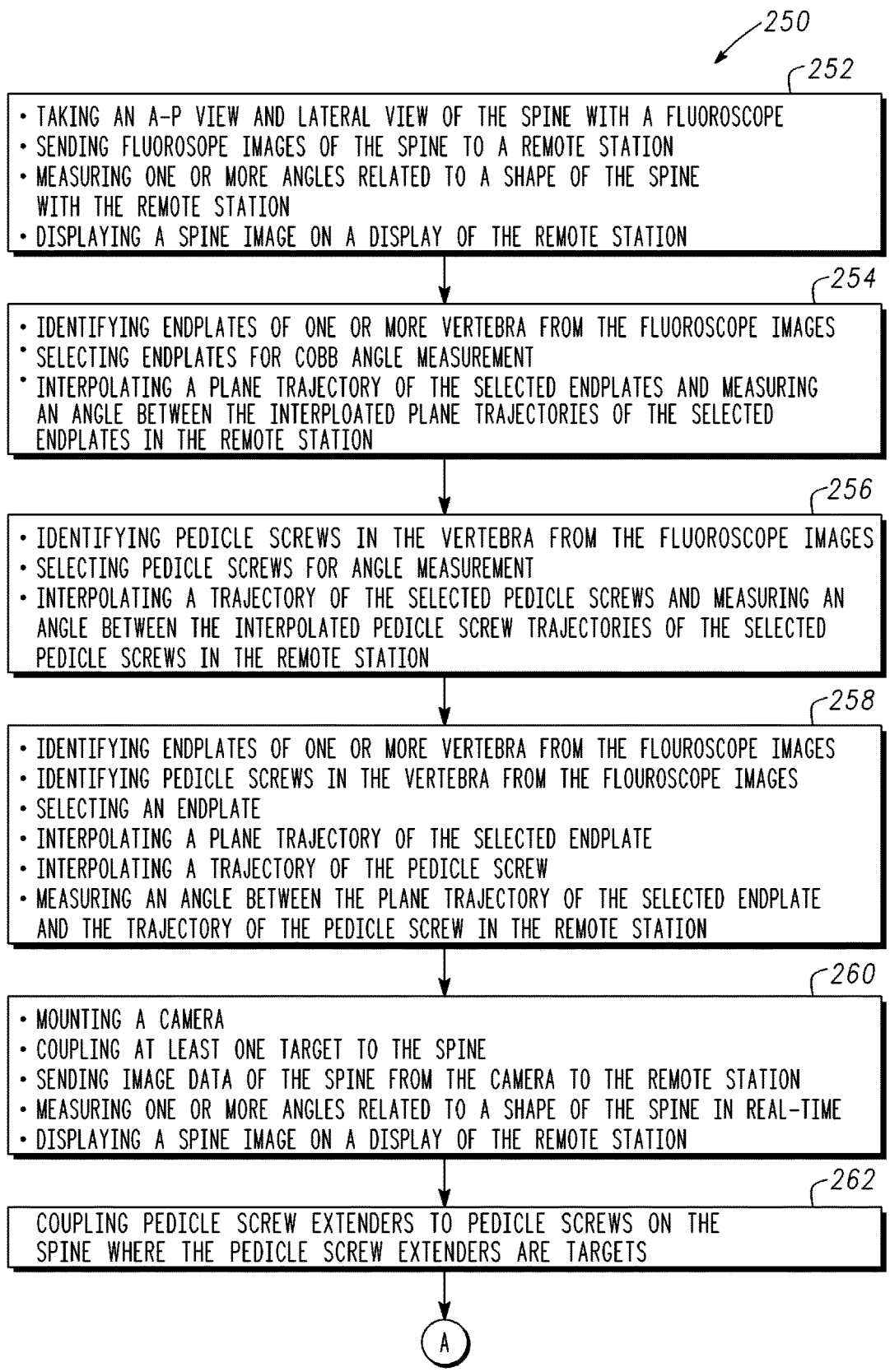
FIG. 17A is a block diagram of a method of spine measurement in accordance with an example embodiment.

FIG. 17 is a block diagram 250 of a method of spine measurement in accordance with an example embodiment. The method of spine measurement can use spine measurement system 10 as disclosed in FIG. 1 and FIG. 5. The method can be practiced with more or less steps and is not limited to the order of steps shown. The method is not limited to the spine example but can be used for hip, knee, shoulder, ankle, elbow, spine, hand, wrist, foot, bone, and musculoskeletal system. Referring briefly to FIG. 1, a model of the spine is created from measurements generated in a remote station application using computer vision on remote station 20. A spine image is displayed on display 22 of remote station 20. The spine image is created from quantitative measurements made by the remote station from fluoroscope images of the spine. Referring back to FIG. 17, in a step 252, a fluoroscope is used to take lateral images and anteroposterior images of the spine. The fluoroscope images are sent to a remote station. The remote station measures one or more angles from the fluoroscope images. The remote station can also measure vertebra axial rotation. A spine image is displayed on a display of the remote station. The spine image comprises the angle measurements and axial rotation made from the fluoroscope images. In one embodiment, the fluoroscope images depict the spine with deformities (pre-correction).

In a step 254, endplates of one or more vertebra are identified from the fluoroscope images. The remote station application uses computer vision to locate the endplates of each vertebra. In general, computer vision software attempts to mimic how humans identify objects. Facial recognition software is one form of computer vision software. Facial recognition software can often identify a face even if the face has been altered to obscure features. Examples of altering looks are growing facial hair, coloring hair, changing skin tone, or significantly changing a hairstyle. Similarly, obscuring features can include wearing a scarf, hat, or glasses to block a portion of the face. A human would try to recognize features that are unique to the individual even with alteration or obfuscation. Computer vision in the remote station application can be used to identify features, objects, or landmarks related to the musculoskeletal system or musculoskeletal surgery. In the example, patient musculoskeletal systems can vary significantly but each will have a similar number of vertebrae and each vertebra will have different shape that can be recognized as the features or landmarks can be viewed in light of the differences or variations. The computer vision software is programmed to recognize each component of the spine even with variations seen across the population. The remote station application using computer vision will identify bone landmarks or other unique features to identify a specific vertebra or a specific feature on a vertebra. As mentioned previously, the vertebrae in the fluoroscope images have been identified. A verification process can also be performed whereby the surgeon verifies that the depiction of the spine on the display of the remote station corresponds to what is seen on the operating table. The endplates of each vertebra have also been identified by the remote station application. Endplates are identified for angle measurement either pre-operatively as part of a pre-operative plan or during the operation by selecting endplates for measurement. The Cobb angle can be measured in sagittal or coronal planes for the selected endplates. The plane trajectory of the selected endplates is interpolated. In general, the plane trajectory of the selected endplates should intersect. The angle between the interpolated plane trajectories of selected endplates are measured. The measured angle is the Cobb angle which is used by the surgeon as a relative measure of the deformity of the spine. The remote station can be configured to measure all the relevant endplate to endplate angles and store them in a table. The selected endplate angle or Cobb angle can be retrieved from the table.

In a step 256, pedicle screws in the vertebra from the fluoroscope images are identified. The remote station application using computer vision is configured to locate pedicle screws in the spine. Pedicle screws are selected for angle measurement. Pedicle screws are identified for angle measurement either pre-operatively as part of a pre-operative plan or during the operation by selecting pedicle screws for measuring. A trajectory of the selected pedicle screws is interpolated. In one embodiment, the remote station is configured to interpolate the pedicle screw trajectories of the selected pedicle screws. The remote station is further configured to measure an angle between the interpolated pedicle screw trajectories of the selected pedicle screws. Alternatively, the remote station can measure all the relevant pedicle screw to pedicle screw angles and store them in a table. The selected pedicle screw to pedicle screw angle can be retrieved from the table.

In a step 258, endplates of one or more vertebra are identified from the fluoroscope images as disclosed hereinabove. Similarly, pedicle screws are identified from the fluoroscope images as disclosed hereinabove. The remote station application using computer vision is configured to locate the endplates of the vertebra and the pedicle screws. An endplate is selected and a pedicle screw is selected. A trajectory of the selected endplate is interpolated. The remote station is configured to interpolate the plane trajectory of the endplate. The trajectory of the pedicle screw is interpolated. The remote station is configured to interpolate the pedicle screw trajectory. An angle is measured between the plane trajectory of the selected endplate and the trajectory of the pedicle screw. Alternatively, the remote station can measure all relevant pedicle screw to endplate angles and store them in a table. The selected pedicle screw and the selected endplate can be retrieved from the table.

In a step 260 a camera is mounted. The spine is in a field of view of the camera. In one embodiment, the camera is mounted to the spine. Alternatively, the camera can be mounted to a surface that is stable and is not subject to movement. One or more targets are coupled to the spine. The targets are in the field of view of the camera. The camera is configured to send image data to the remote station. The remote station using computer vision is configured to measure positions of each vertebra from the position of the targets. In general, position change in a target can be interpolated back to a change in position of the vertebra to which it couples. Thus, the shape of the spine is known through the position of the targets. How each vertebra is positioned to one another can be represented by one or more metrics, angles, or axial rotation. The measured positions of the vertebrae in real-time can be related or integrated with the spine image created from the fluoroscope images of the spine deformity. As mentioned previously, these measured metrics are used to generate the spine image displayed on the display of the remote station in real-time. A spine or spine rod image is displayed on a display of the remote station.

In a step 262 a pedicle screw extenders are coupled to pedicle screws on the spine. The pedicle screw extenders are configured to be targets for the remote station application. The remote station application using computer vision can recognize pedicle screw extenders as targets. The pedicle screw extenders are coupled to the spine to allow the surgeon to see the spine shape while manipulating the spine. The pedicle screw extenders can have distinctive features that support recognition of by the remote station application in a surgical environment.

In a step 264 the spine is manipulated. A surgeon manipulates the spine to determine if the pre-operative plan can be implemented, the limits that the spine can be shaped, and determine if any unknown issues exist. The manipulation is a subjective analysis of the spine and can include shaping the spine to an acceptable outcome. The remote station application measures the spine shape in real-time during the spine manipulation. Real-time metrics are displayed on the display of the remote station corresponding to the spine shape and other attributes of the spine. In one embodiment, a sagittal Cobb angle, a coronal Cobb angle, and an axial rotation is displayed on the display of the remote station. During the spine manipulation the surgeon can store or freeze a spine shape in-situ. The in-situ spine shape will include the metrics generated in real-time that characterize the spine shape. Typically, the surgeon stores the in-situ spine shape if it produces a desired outcome. The in-situ spine shape and metrics can be displayed and compared to the pre-operative plan spine shape and metrics thereby allowing the surgeon to see differences after the subjective analysis of the spine.

In a step 266, the pre-operative defined rod shape is reviewed. The surgeon has both quantitative measurement data and subjective data related to the spine. The surgeon can then determine if the pre-operative defined rod shape results in a correct spine outcome. The rod shape can be modified to meet the spine outcome based on the real-time metrics. The new rod shape can be formed and coupled to the pedicle screws. The shape of the spine can then be measured to determine if the new rod shape achieves the outcome desired by the surgeon.

Figure 18:
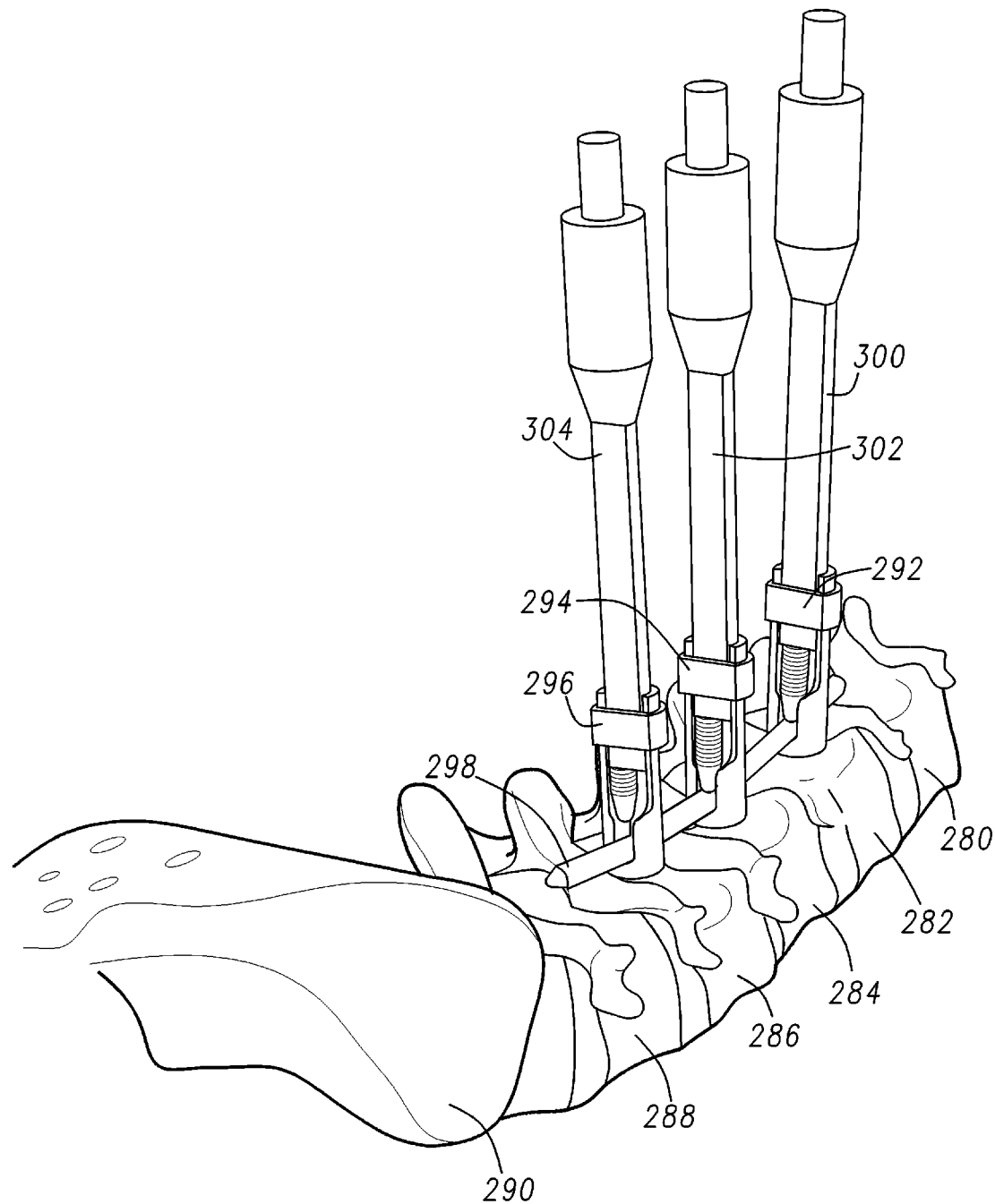
FIG. 18 is an illustration of a rod coupled to a lower lumbar region in accordance with an example embodiment.

Referring briefly to FIG. 18, an example of a rod 298 coupled to the spine to change the spine contour as disclosed hereinabove is provided. In the example, a lumbar region of the spine is illustrated. The lumbar region is in view of the camera of the spine measurement system. The lumbar region comprises L1 vertebra 280, the L2 vertebra 282, L3 vertebra 284, L4 vertebra 286, L5 vertebra 288, and Sacrum 290. A pedicle screw 292 couples to L2 vertebra 282. A pedicle screw 294 couples to L3 vertebra 284. A pedicle screw 296 couples to L4 vertebra 286. A rod 298 is shaped to achieve the desired outcome for the spine surgery. As disclosed above, the rod shape can be the pre-operative plan rod shape or a modified rod shape based on quantitative measurement data from the spine measurement system and the subjective assessment of the surgeon. Rod 298 is held in place by pedicle screw extenders 300, 302, and 304. Pedicle screw extenders 300, 302, and 304 are respectively coupled to pedicle screws 292, 294, and 296. In general, a head of a pedicle screw is designed to receive a rod. A pedicle screw extender screws into a corresponding head of a pedicle screw and clamps down on the rod. The spine is forced to take the shape of the rod. The rod can forcibly cause vertebra rotation.

Pedicle screw extenders 300, 302, and 304 are in the field of view of the camera. Information related to pedicle screw extenders 300, 302, and 304 is stored in the remote station. For example, the dimensions and shape of a pedicle screw extender is known. The remote station application using computer vision can recognize pedicle screw extenders 300, 302, and 304. Pedicle screw extenders 300, 302, and 304 can have two-dimensional or three-dimensional images on an exterior surface to support recognition. Moreover, the remote station application can determine a relative position of pedicle screw extenders 300, 302, and 304 in 3D space.

The remote station also has information related to pedicle screws 292, 294, and 296. The information includes the dimension data of each pedicle screw and data related to each pedicle screw installation such as the point of entry on the vertebra and the trajectory into the vertebra. Thus, the remote station can recognize a pedicle screw extender position and interpolate back to the location and trajectory of a corresponding pedicle screw to determine a position of a vertebra to which the pedicle screw extender couples. The remote station can do this in real-time for each pedicle screw extender in the field of view. The information can be used with the initial spine shape measurements using fluoroscope images to provide a spine image and quantitative measurement relating to the spine shape with rod 298 in place.

FIG. 19 is a block diagram 320 of a method of pedicle screw placement in accordance with an example embodiment. The method can use spine measurement system 10 of FIG. 1 to drill a path in a vertebra to place a pedicle screw. Spine measurement system 10 supports locating a point of entry in the vertebra and the angle of drilling at the point of entry. Moreover, the method can be practiced with more or less steps and is not limited to the order of steps shown. The method is not limited to the spine example but can be used for hip, knee, shoulder, ankle, elbow, spine, hand, wrist, foot, bone, and musculoskeletal system.

In a step 322, the camera is directed at the spine. More specifically, the targeted vertebra is in a field of view of the camera including the region where a pedicle screw is being placed. The camera can focus on the targeted vertebra to view the bone features in detail. The targeted vertebra is identified by the remote station application using computer vision and can be shown on the display of the remote station. The surgeon can verify that the targeted vertebra on the display of the remote station corresponds to the vertebra in which the pedicle screw is being placed. In one embodiment, the remote station application for pedicle screw placement uses computer vision to identify features or landmarks that provide a reference for locating specific regions on the targeted vertebra.

In a step 324, information is retrieved from the remote station detailing the location for pedicle screw placement in relation to the landmarks on the targeted vertebra. The remote station application using computer vision can identify each vertebra of the spine. The computer vision finds features or landmarks specific to each vertebra. The features or landmarks used by computer vision are selected to be a unique combination for the targeted vertebra yet the features and landmarks can be used to identify the same vertebra over the large physical variations that occur in nature. The entry point location for the targeted vertebra is stored in memory of the remote station. The information describing the entry point location of the targeted vertebra relates to the identified features and landmarks by the remote station application. Similarly, the trajectory in which to align the drill for each vertebra at the point of entry is stored in memory of the remote station and can be related to the identified features and landmarks. In one embodiment, the point of entry can be displayed on the display of the remote station by a circle, crosshair, or other identifier to locate the spot where drilling should occur.

Figure 20:
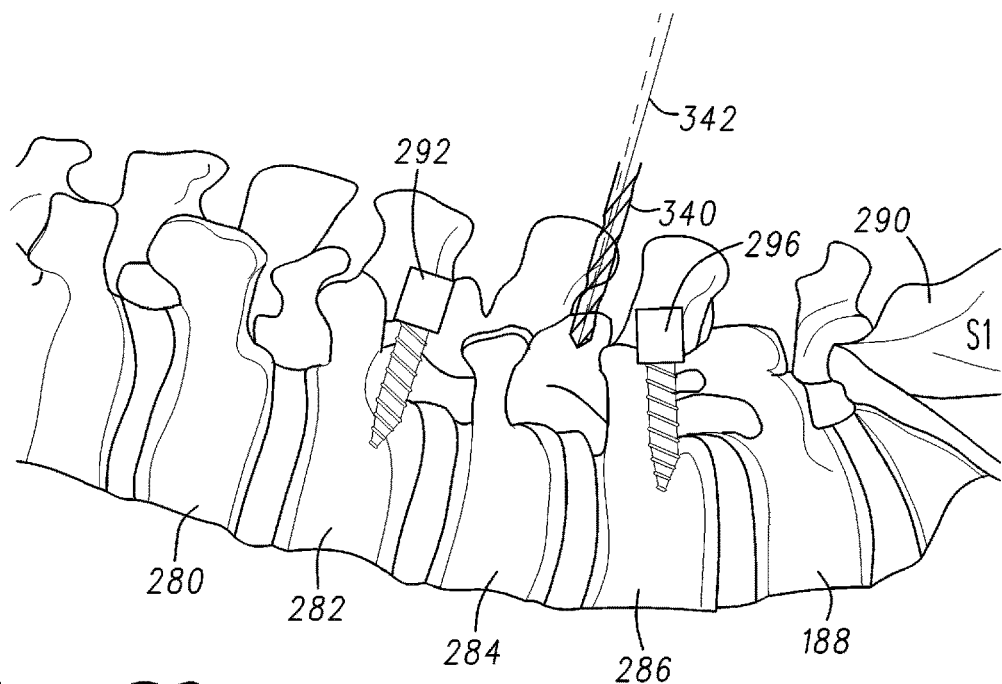
FIG. 20 is a lateral view of the lower lumbar region illustrating a drill trajectory in accordance with an example embodiment.

Referring briefly to FIG. 20, a lateral view of the lower lumbar region is illustrated. The lumbar region comprises L1 vertebra 280, the L2 vertebra 282, L3 vertebra 284, L4 vertebra 286, L5 vertebra 288, and sacrum 290. A pedicle screw 292 couples to L2 vertebra 282. A pedicle screw 296 couples to L4 vertebra 286. L3 vertebra 284 is being drilled for pedicle screw placement. Spine measurement system 10 of FIG. 1 can be used to place pedicle screws. A drill 340 is shown approaching L3 vertebra 284. Drill 340 has a trajectory 342 from the lateral view that has been identified as an optimal path for pedicle screw placement for L3 vertebra 284. In general, the remote station application using computer vision monitors the position of drill 340 in real-time. The remote station application directs drill 340 to trajectory 342 using visual, audio, and haptic queues.

Figure 21:
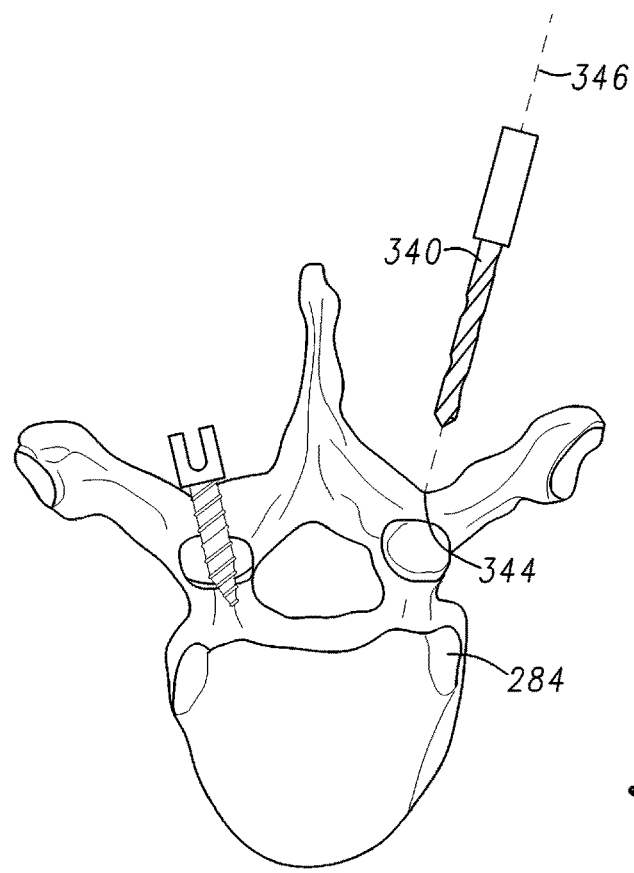
FIG. 21 is a transverse view of the L3 vertebra illustrating a drill trajectory in accordance with an example embodiment.

Referring briefly to FIG. 21, a transverse view of L3 vertebra 284 is illustrated. Spine measurement system 10 of FIG. 1 can be used for pedicle screw placement. L3 vertebra 284 is being drilled for pedicle screw placement. A point of entry 344 is identified by the remote station for optimal placement of a pedicle screw. Drill 340 is shown approaching L3 vertebra 284 and will contact point of entry 344. Drill 340 has a trajectory 346 from the transverse view that has been identified as an optimal path for pedicle screw placement for L3 vertebra 284. FIG. 20 and FIG. 21 illustrates that the trajectory can be complex. The remote station application using computer vision can monitor the position of drill 340 in 3D space and direct the trajectory for optimal placement as viewed in both the transverse and lateral planes as disclosed in FIG. 20 and FIG. 21.

In a step 326 the tool is guided to a point of entry of the targeted vertebra. In one embodiment, the remote station application uses computer vision to locate and identify the position of the tool in relation to the targeted vertebra. The tool can also include position sensing technology such as accelerometers, gyroscopes, global positioning system, infra-red, optical, or acoustic to support placement of the tool. In the example, an opening will be drilled to locate a pedicle screw in the targeted vertebra. The drill tip can be identified by the remote station application using computer vision and directed to the point of entry on the targeted vertebra. The display of the remote station can also be used to support locating the tool to the point of entry. Visual aids can be used in the targeting process to locate the tool to the point of entry. Similarly, the tool is guided to have a correct trajectory. The tool needs to be placed in the proper orientation at the point of entry on the targeted vertebra before drilling a path. As mentioned previously, the remote station retrieves the stored information related to the tool trajectory for placing a pedicle screw in the targeted vertebra. In one embodiment, the remote station application using computer vision recognizes the position and trajectory of the tool in relation to the identified landmarks and features of the targeted vertebra. The sensing technology in the tool can also support aligning the tool in the correct trajectory. Visual aids on the display of the remote station can be used in aligning the tool to the correct trajectory. Once the tool is placed at point of entry at the correct trajectory an opening is formed in the targeted vertebra corresponding to where the pedicle screw is placed. In the example, the targeted vertebra is drilled to a predetermined depth. Alternatively, a wire could be placed through the bone to a predetermined depth.

In a step 328 the tool is monitored. The tool is in the field of view of the camera. The remote station application using computer vision recognizes and can track the position of the tool in 3D space as it relates to the spine. The remote station application tracks the tool in real-time within the field of view of the camera. The remote station can indicate the point of entry on the targeted vertebra. The remote station application can further identify that the tool couples to the point of entry on the targeted vertebra.

In a step 330, information related to a correct trajectory of the tool is stored on the remote station. The information is retrieved and used by the remote station application in comparing an alignment of the tool to the correct trajectory in support of achieving a correct tool alignment at the point of entry on the target vertebra. The trajectory of the tool can be indicated in real-time. The trajectory can be indicated on the tool or the display of the remote station. The remote station using computer vision recognizes the tool and the trajectory of the tool. Moreover, the remote station supports aligning the tool to the correct trajectory.

In a step 332, feedback can be provided to support aligning the tool at the point of entry of the targeted vertebra. Similarly, feedback can be provided to support placing the tool at the correct trajectory. The feedback can be visual, audible, or haptic. For example a simple green light or red light can be used in locating the tool to the point of entry on the targeted vertebra. Information related to the direction to move the tool can be provided on the display of the remote station until the green light is received.

Figure 22:
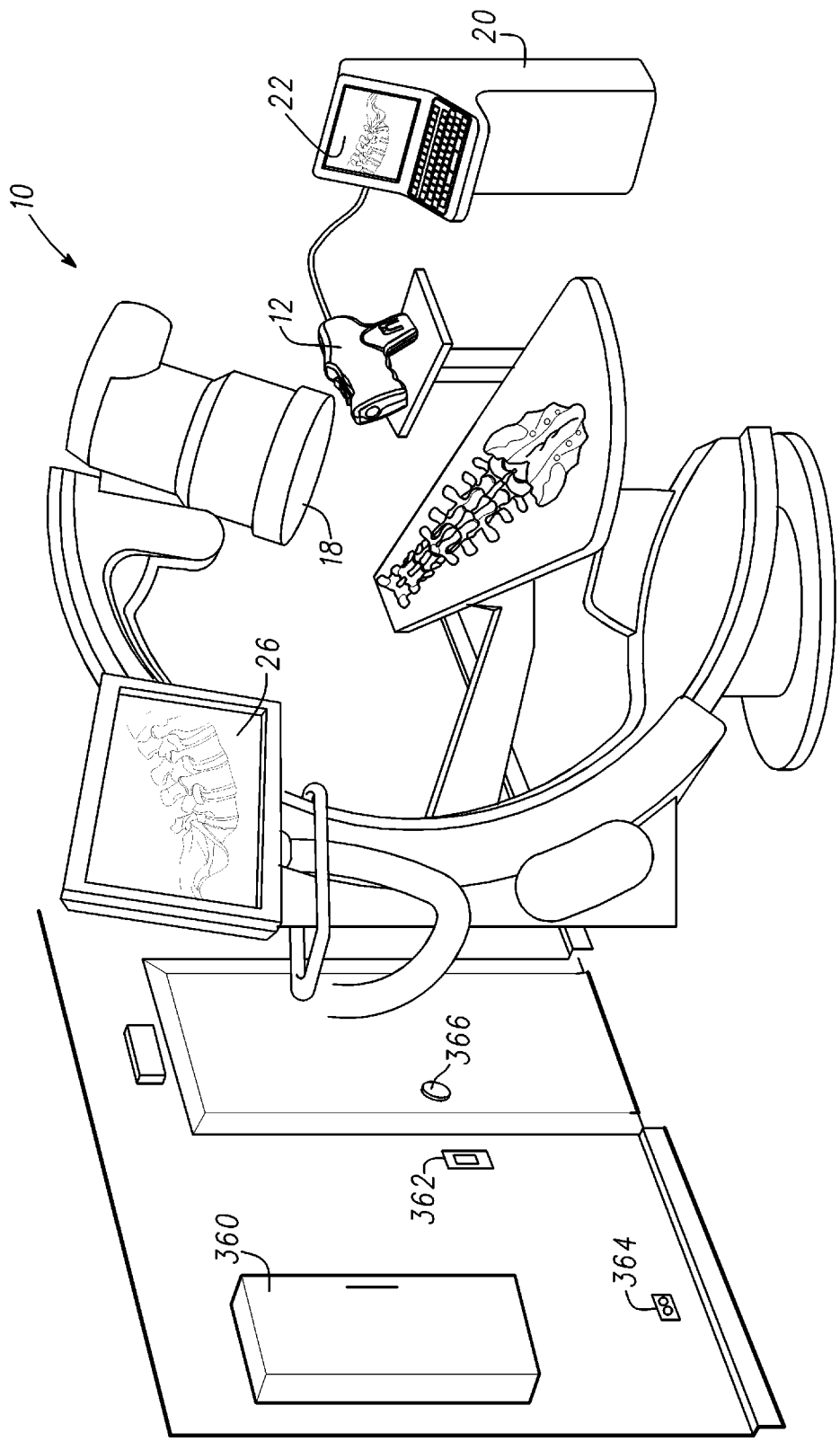
FIG. 22 is an illustration of the spine measurement system configured to support pedicle screw placement in accordance with an example embodiment.

FIG. 22 is an illustration of spine measurement system 10 configured to support pedicle screw placement in accordance with an example embodiment. In general, each vertebra of the spine is different. Similarly, an optimal pedicle screw placement is different for each vertebra of the spine. Spine measurement system 10 supports placing a tool at a point of entry of a targeted vertebra and placing the tool at the correct trajectory to drill a path for pedicle screw placement. Optical measurement probe 12 includes a camera that is configured to have a spine in a field of view. Optical measurement probe 12 can be mounted to a stable object that allows a minimally impeded view of the spine and more specifically a targeted vertebra for pedicle screw placement. The position of optical measurement probe 12 can be referenced prior to starting a procedure. The camera of optical measurement probe 12 can send image data related to static objects to remote station 20. The remote station application using computer vision can locate and identify a position of three or more static objects. For example, on a wall in the field of view of the camera there are static objects such as a cabinet 360, a light switch, 362, an outlet 364, or a door knob 366. The static objects in the field of view of the camera cannot move during the surgery. An origin of the coordinate system is configured to be referenced to at least three static objects in the field of view of the camera. In one embodiment, the origin of the coordinate system of spine measurement system 10 for pedicle screw installation is configured to be located in the camera of optical measurement probe 12. The position of the static objects will have different position when referenced to the origin if the camera is moved from its position and orientation. A visual, audible, or haptic warning is provided when movement of the camera is detected. The warning is provided to indicate that movement has occurred but also to determine if it was the camera or something else had moved. The spine measurement system 10 can also turn off any tool that can be affected by the movement. For example, the tool could be positioned incorrectly by system 10 when movement is detected. Turning the tool off prevents an irreversible error from occurring until the problem is resolved. In one embodiment, the remote station application can compensate by adding an offset that accounts for a camera movement so all measurements remained linked to the original coordinate system. Conversely, movement can occur that requires the coordinate system to be reset and the process started over to locate the tool.

Remote station 20 is configured to receive image data from the camera. In one embodiment, the camera in optical measurement probe 12 is coupled by cable to remote station 20. Alternatively, the camera is coupled wirelessly to remote station 20. The spine is exposed such that the landmarks and features of the vertebra can be viewed by the camera. Remote station 20 is configured to use computer vision to catalog vertebrae in the field of view of the camera. Remote station 20 can be configured to receive confirmation from a user that the catalogued vertebrae in the field of view are correctly identified. The remote station application uses information stored in the remote station related to features or landmarks of each vertebra to recognize from the image data what vertebra are in the field of view. In one embodiment, the remote station includes a lookup table configured to provide reference landmarks or features.

The remote station identifies the targeted vertebra for pedicle screw installation and can identify it on display 22 of remote station 20. The surgeon can verify that the vertebra identified on display 22 is the targeted vertebra for pedicle screw installation. In one embodiment, the tool can be configured to penetrate bone of the targeted vertebra. For example, a drill is commonly used to form a path in the bone that can be tapped to receive the pedicle screw. Remote station 20 using computer vision is configured to locate a point of entry of the targeted vertebra. Remote station 20 has stored information relating to a point of entry for pedicle screw placement for each vertebra. The stored information can be on a lookup table having locations of points of entry for each vertebra. The location of the point of entry can be related to the features and landmarks used to identify a vertebra. The remote station application identifies features and landmarks on the targeted vertebra and locates the point of entry using the information stored in the remote station 20. Furthermore, remote station 20 has stored information related to a trajectory to penetrate the targeted vertebra. In one embodiment, the remote station includes a lookup table related to the trajectory of the tool for the targeted vertebra. Remote station 20 is configured to direct the trajectory of the tool in the targeted vertebra. The camera sends image data of the surgeon directing the tool to the point of entry in real-time. The remote station application using computer vision locates a position of the tool in real-time and identifies when the tool has a correct trajectory for the targeted vertebra and is coupled to the point of entry.

In one embodiment, the tool is a drill. The remote station application can recognize a position of the drill and drill tip using computer vision. The drill can include electronic circuitry to communicate with the remote station. Furthermore, the drill can include position sensors to provide trajectory or location information. The position sensors in the drill can be used to support the remote station application in directing the drill to the point of entry and the correct trajectory for the targeted vertebra. The tool can be configured to provide feedback related to aligning the tool to the point of entry of the targeted vertebra and to the trajectory of the tool at the point of entry. The feedback to the user can be visual, audible, or haptic. The feedback simplifies positioning the tool at the point of entry and at the correct trajectory. Remote station 20 can also provide feedback to the surgeon. The camera and remote station are configured to monitor the tool position and trajectory in real-time. The display 22 of remote station 20 can also provide visual, audible, or haptic feedback to the surgeon to support positioning the tool to the point of entry and positioning the tool for correct trajectory. The feedback can provide feedback related to correct and incorrect placement.

Figure 23:
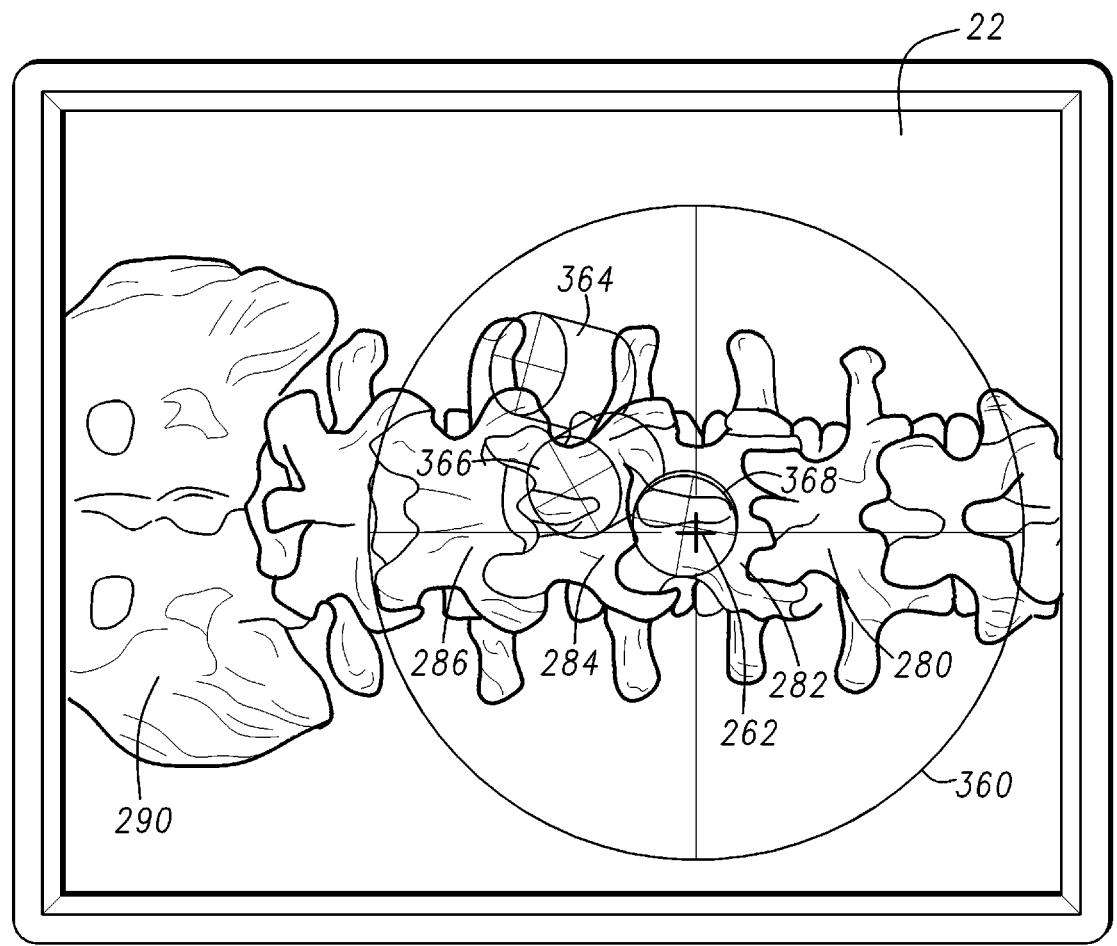
FIG. 23 is an illustration of feedback to support directing the tool to the point of entry on the targeted vertebra in accordance with an example embodiment.

FIG. 23 is an illustration of remote station 20 tracking a position of the tool in accordance with an example embodiment. The tool position and trajectory is displayed on display 22 in real-time. The remote station application uses computer vision to identify and track the position of the tool in 3D space using image data received from the camera monitoring the spine. In the example, a posterior view of the lumbar region is displayed on display 22. The lumbar region comprises L1 vertebra 280, the L2 vertebra 282, L3 vertebra 284, L4 vertebra 286, L5 vertebra 288, and sacrum 290. In one embodiment, the tool is a drill. The drill is used to drill a path in the targeted vertebra to install a pedicle screw. The point of entry is a location in the targeted vertebra to install a pedicle screw. In one embodiment, display 22 includes a circle 360 that encompasses at least a portion of the targeted vertebra. A cross-hair 362 in circle 360 identifies the location of point of entry for the drill. The point of entry is located by the remote station application identifying features and landmarks of the targeted vertebra and retrieving stored information relating the point of entry to the identified features or landmarks in the field of view of the camera.

The drill can be represented by a cylinder on display 22 of the remote station 20. The center of the drill can be represented by a cross-hair on the cylinder. As mentioned, the remote system application receives image data and tracks a position of the drill as it is moved by the surgeon. Multiple cylinders are shown to indicate movement of the drill to the point of entry. Movement of the drill is indicated by cylinder 364, cylinder 366, and cylinder 368. Note that the indicated movement of cylinders 364, 366, and 368 has the drill moving towards the point of entry. The drill not only has to align to the point of entry but the drill also has a trajectory alignment. In one embodiment, the trajectory alignment can be represented by a circle formed around cross-hair 362. The circle is approximately the same diameter or larger than cylinders 364, 366, and 368.

Cylinder 364 represents the drill being the furthest from the point of entry. The drill trajectory is also misaligned from the correct trajectory. The trajectory is indicated by the three dimensional representation of cylinder 364. Note that a cylinder wall of cylinder 364 is visible on display 22. In one embodiment, an image of a cylinder on display 22 appearing as a circle without a cylinder wall visible will have the correct trajectory. The drill is moving closer to the point of entry, which is represented by cylinder 366 in display 22. Cylinder 366 is closer to the point and has less cylinder wall exposed than cylinder 364. The reduction in the exposed cylinder wall indicates that the trajectory of the drill is moving towards the correct trajectory. Cylinder 368 represents the drill almost at the point of entry. The cross-hair at the point of entry almost aligns with the cross-hair on cylinder 368. Similarly, the cylinder wall of cylinder 368 almost cannot be seen. In other words, cylinder 368 is almost at the correct trajectory which is represented by cylinder 368 viewed as a circle on display 22 of remote station 20. The use of visual, audible, or haptic feedback such as beeping or vibrating could be used to further enhance aligning the tool. For example, a rapid audible beeping can indicate that the device is not close to the point of entry. The audible beeping could slow down or quit when the point of entry is aligned to the device. Similarly, the drill could be made to vibrate when the trajectory alignment is incorrect. The vibration could be reduced as the drill nears the correct trajectory. A green light indicator could flash when the correct trajectory is reached and the vibration stops. These are just examples as other types of feedback can be provided that supports alignment to the point of entry and alignment to the correct trajectory.

Figure 24:
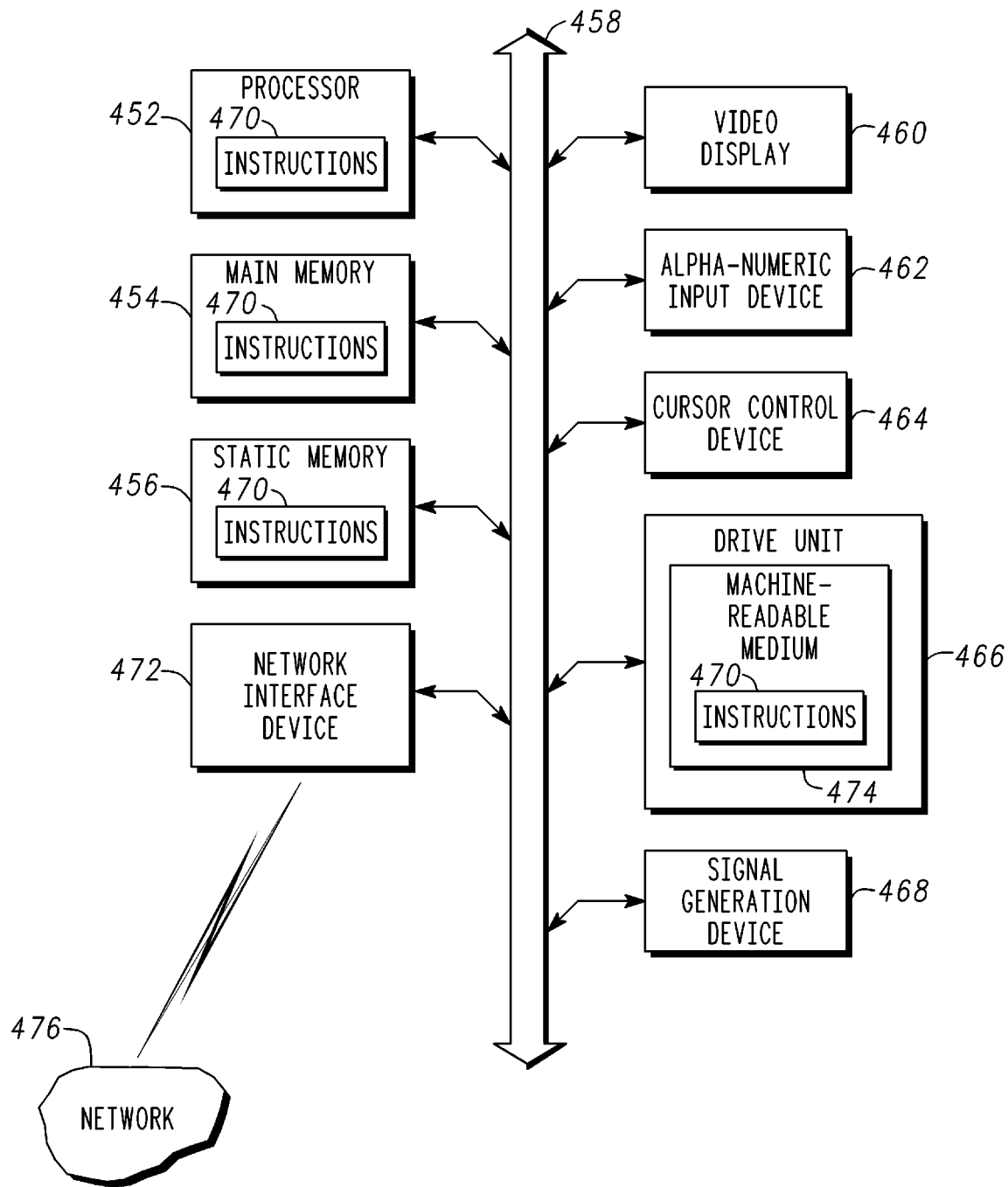
FIG. 24 depicts an exemplary diagrammatic representation of a machine in the form of a spine measurement system in accordance with an example embodiment.

FIG. 24 depicts an exemplary diagrammatic representation of a machine in the form of a spine measurement system 450 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 450 may include a processor 452 (e.g., a central processing unit (CPU), a graphics processing unit (GPU, or both), a main memory 454 and a static memory 456, which communicate with each other via a bus 458. System 450 may further include a video display unit 460 (e.g., a liquid crystal display (LCD), a flat panel, a solid state display, or a cathode ray tube (CRT)). System 450 may include an input device 462 (e.g., a keyboard), a cursor control device 464 (e.g., a mouse), a disk drive unit 466, a signal generation device 468 (e.g., a speaker or remote control) and a network interface device 472.

The disk drive unit 466 can be other types of memory such as flash memory and may include a machine-readable medium 474 on which is stored one or more sets of instructions (e.g., software 470) embodying any one or more of the methodologies or functions described herein, including those methods illustrated above. Instructions 470 may also reside, completely or at least partially, within the main memory 454, the static memory 456, and/or within the processor 452 during execution thereof by the system 450. Main memory 454 and the processor 452 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 470, or that which receives and executes instructions 470 from a propagated signal so that a device connected to a network environment 476 can send or receive voice, video or data, and to communicate over the network 476 using the instructions 470. The instructions 470 may further be transmitted or received over a network 476 via the network interface device 472.

While the machine-readable medium 466 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 25:
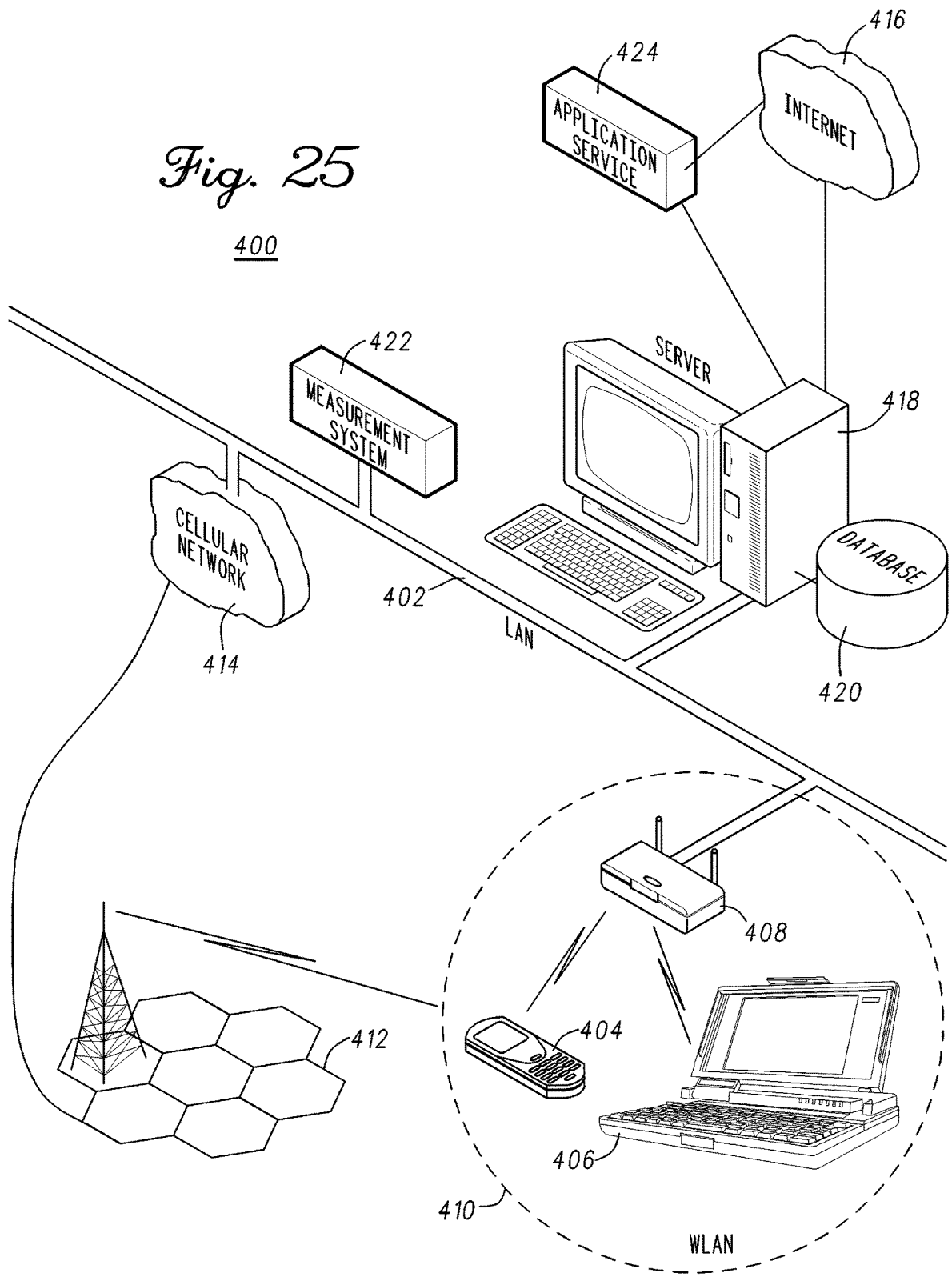
FIG. 25 is an illustration of a communication network for measurement and reporting in accordance with an example embodiment.

FIG. 25 is an illustration of a communication network 400 for measurement and reporting in accordance with an exemplary embodiment. Briefly, the communication network 400 expands broad data connectivity to other devices or services. As illustrated, the measurement and reporting system 422 can be communicatively coupled to the communications network 402 and any associated systems or services.

As one example, measurement system 422 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 400 can further be tied to an Electronic Medical Records (EMR) system to implement health information technology practices. In other embodiments, the communication network 400 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 400 can provide wired or wireless connectivity over a Local Area Network (LAN) 402, a Wireless Local Area Network (WLAN) 410, a Cellular Network 414, and/or other radio frequency (RF) system. The LAN 402 and WLAN 410 can be communicatively coupled to the Internet 416, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 400 can utilize common computing and communications technologies to support circuit-switched and/or packet-switched communications. Each of the standards for Internet 416 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 414 can support voice and data services over a number of access technologies such as GSM-GPRS, EDGE, CDMA, UMTS, WiMAX, 2G, 3G, WAP, software defined radio (SDR), and other known technologies. The cellular network 414 can be coupled to base receiver 412 under a frequency-reuse plan for communicating with mobile devices 404.

The base receiver 412, in turn, can connect the mobile device 404 to the Internet 416 over a packet switched link. The internet 416 can support application services and service layers for distributing data from spine measurement system 422 to the mobile device 404. Mobile device 404 can also connect to other communication devices through the Internet 416 using a wireless communication channel.

The mobile device 404 can also connect to the Internet 416 over the WLAN 410. Wireless Local Access Networks (WLANs) provide wireless access within a local geographical area. WLANs are typically composed of a cluster of Access Points (APs) 408 also known as base stations. The spine measurement system 422 can communicate with other WLAN stations such as laptop 406 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 400, the spine measurement system 422 can establish connections with a remote server 418 on the network and with other mobile devices for exchanging data. The remote server 418 can have access to a database 420 that is stored locally or remotely and which can contain application specific data. The remote server 418 can also host application services directly, or over the internet 416.

Figure 26:
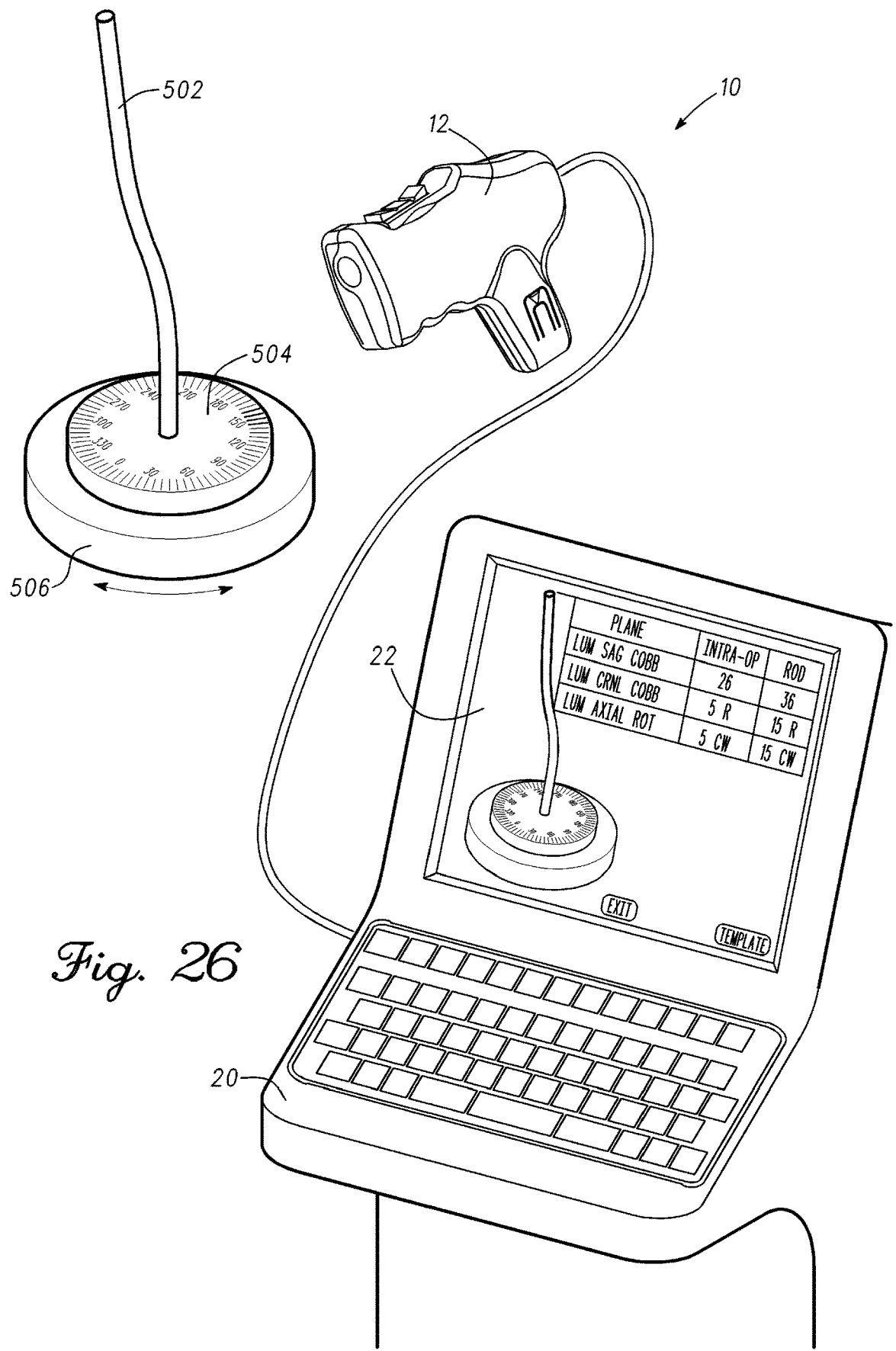
FIG. 26 is an illustration of the spine measurement system in accordance with an example embodiment.

FIG. 26 is an illustration of spine measurement system 10 in accordance with an example embodiment. In general, a surgeon bends a rod to alter a shape of the spine. The surgeon typically has a pre-operative plan and target metrics to determine if the rod shape achieves a desired spine outcome. The bending of rod 502 is subjective, and is based on the observations of the surgeon prior to and during surgery. Rod 502 can have a complex shape. Prior to bending rod 502, pedicle screws are anchored to vertebra of the spine. Rod 502 is coupled to the pedicle screws in the spine to forcibly change a position of the vertebra thereby changing the spine contour.

Spine measurement system 10 can be used to measure a contour, profile, or shape of rod 502 that is non-linear in shape. An obvious benefit of measuring rod 502 is that metrics related to the spine outcome can be calculated from the measurement of rod 502. Alternatively, measurements of rod 502 can be used in conjunction with a spine model generated from quantitative measurements in spine measurement 10 to show how the spine shape is altered on display 22 and similarly calculate metrics related to the spine shape. For example, the metrics generated from the measurement of rod 502 can be Cobb angles and axial rotation as determined by the bends in rod 502 and the locations of the known locations of the pedicle screws in the vertebra. The metrics can be used to determine if rod 502 needs to be modified to achieve the spine outcome. Alternatively, remote station 20 can simulate how changing rod 502 position affects calculated metrics. Remote station 20 can be used to determine placement of rod 502 to best achieve the desired outcome or to suggest modifications to rod 502 if the outcome is not achieved.

The rod measurement system comprises encoded collar 504, a camera, and a remote station 20. Encoded collar 504 includes markings that relate a region of collar 504 to a region of rod 502. In one embodiment, encoded collar 504 corresponds to an angular orientation of rod 502. In the example, encoded collar 504 is fitted on rod 502 such rotating rod 502 also rotates collar 504. Encoded collar 504 can be an interference fit or can attach to the rod in a manner where encoded collar 504 does not shift or change position in relation to the rod. In the example, encoded collar is a degree wheel having markings that indicate a position of the wheel. A full rotation of rod 502 corresponds to 360 degrees on encoded collar 504. A portion of rod 502 from a 2D image taken by the camera is related to the degree markings indicated on encoded collar 504. Thus, each 2D image taken by the camera provides a contour of rod 502 and a rod position that is indicated on encoded collar 504 by the identifying markings (e.g. degrees of the degree wheel). The degree wheel is an example of markings that can be used to identify a rod position. In general, the identifying markings can be of any form that can be identified from an image. For example, bar code can be used to identify portions of encoded collar 504. Bar code can be read from a 2D image in an automated process and used to identify the position or angular orientation of rod 502. In the example, the camera is in optical measurement probe 12 as part of a spine measurement system. The camera couples to remote station 20 and is configured to provide images of encoded collar 504 and rod 502. In one embodiment, remote station 20 is a processor based system that is configured to run software. Remote station 20 includes image processing software and is configured to process the images and generate quantitative measurement data related to the rod shape in 3D. Remote station 20 is configured to recognize rod 502, encoded collar 504, and the plurality of markings on encoded collar 504. In the example, the dimensions of encoded collar 504 are provided to the remote station. The known dimensions of encoded collar 504 are used as a scale reference for the remote station to relate one image to another such that rod 502 and encoded collar 504 are substantial equal in each image. The known dimensions of encoded collar 504 are also used as a reference to measure dimensions of other objects in the image such as rod 502. In particular, remote station 20 is configured to receive images taken while rod 502 is rotated at least 360 degrees. The camera in optical measurement probe 12 is configured to take a plurality of images while rod 502 is rotated at least 180 degrees. Remote station 20 receives the images and processes the images to generate quantitative measurement data related to a shape of rod 502 in three-dimensions (e.g. 3D). The measurement comprises 2D portions of rod 502 approximating 180 degree view of rod 502 that are summed together to generate a 3D measurement of the rod contour or rod shape. In one embodiment, rod 502 is rotated 360 degrees or more.

In the example, a distal end of rod 502 couples to a platen 506. As shown, encoded collar 504 is coupled to rod 502. Alternatively, platen 506 can have markings similar to encoded collar 504 thereby eliminating the need for encoded collar 504. Platen 506 includes a spindle and a bearing that supports rotation. In one embodiment, platen 506 can rotated by hand. Optical measurement probe 12 will capture one or more full rotations of rod 502 and collar 504. In another embodiment, platen 506 can be rotated by a motor coupled to platen 506. Using a motorized platen 506, rod 502 can be rotated at a constant speed and not subject to variations that could occur when spinning by hand.

The camera in optical measurement probe 12 takes a number of images while rod 502 is spinning. In general, the camera in optical measurement probe 12 can provide high resolution images that supports reading the markings on collar 504 on each image. As an example, the rod 502 can be spun at one revolution per second. Optical measurement probe 12 can take greater than 30 images per second allowing each image to correspond to 12 degrees of rod 502. The images are provided to remote station 20. In general, the number of images and the speed at which rod 502 is spun can vary but needs to be sufficient to generate the three dimensional profile of rod 502 from a plurality of images. Remote station 20 can provide measurements of rod 502 or related metrics from the measurement of rod 502. In one embodiment, metrics related to how rod 502 will affect the curvature of the spine are calculated by remote station 20 and displayed on display 22. For example, sagittal Cobb angle, coronal Cobb angle, and axial rotation can be provided corresponding to measured rod 502 to allow the surgeon to determine if rod 502 meets the goals of the surgery.

Figure 27:
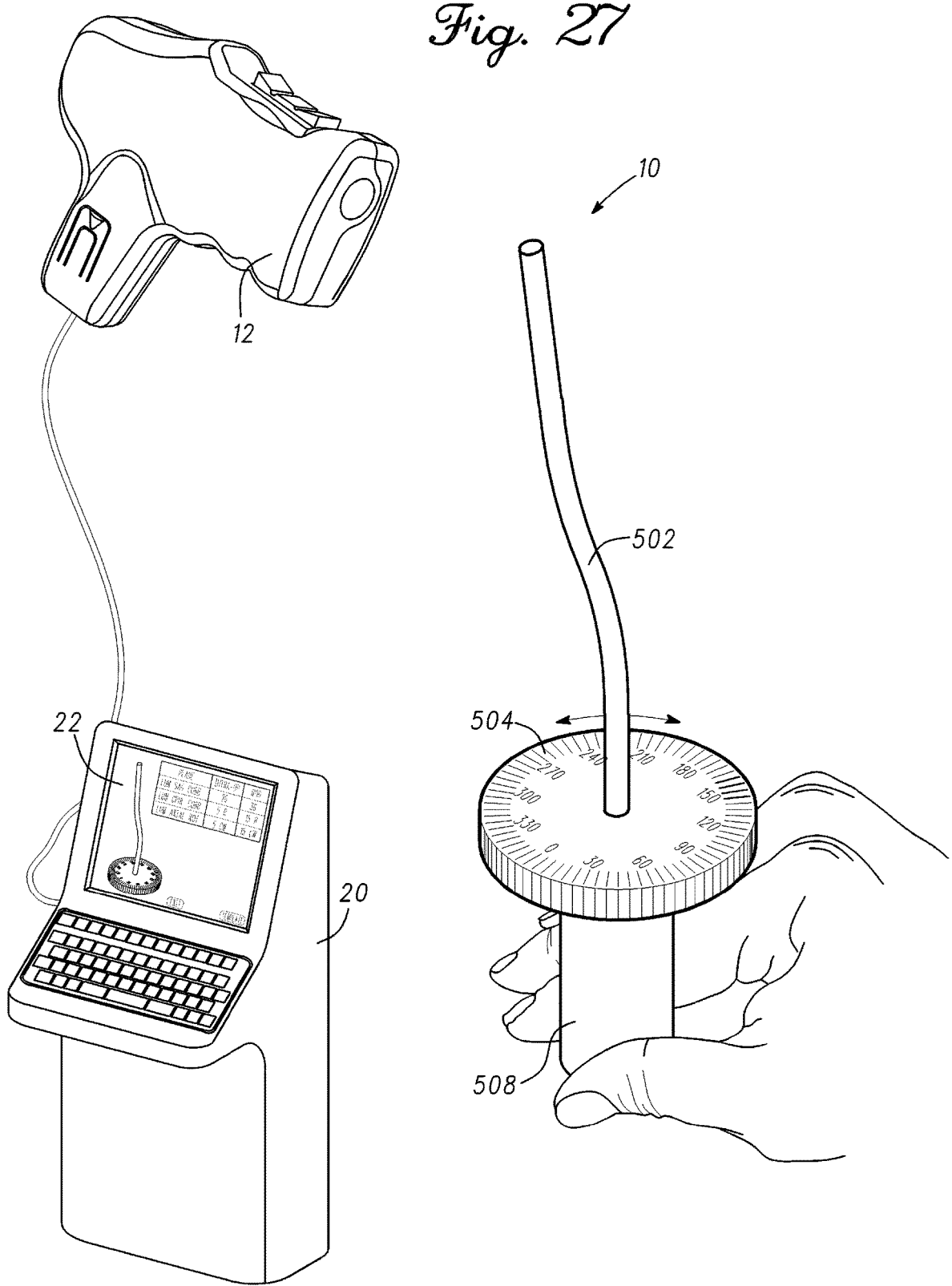
FIG. 27 is an illustration of the spine measurement system in accordance with an example embodiment.

FIG. 27 is an illustration of spine measurement system 10 in accordance with an example embodiment. Optical measurement probe 12 includes a camera configured to provide images to remote station 20. Encoded collar 504 couples to a distal end of rod 502. Encoded collar 504 includes a knob 508 that is a finger hold. Rod 502 and encoded collar 504 are in a field of view of the camera of optical measurement probe 12. Knob 508 can be held in the thumb and forefinger and rotated thereby rotating rod 502. Optical measurement probe 12 is configured to capture a predetermined number of images over a single complete rotation of rod 502. The identifying markings on encoded collar 504 facing the camera in optical measurement probe 12 indicate the angular orientation of rod 502. In general, the number of images and the speed at which rod 502 can be spun will vary depending on the user but needs to be sufficient to generate the three dimensional profile of rod 502 from a plurality of images. Typically, more than ten 2D images per 360 degrees of rotation are needed to generate a 3D measurement of rod 502. In the example, thirty 2D images per 360 degrees of rotation are summed to generate a 3D measurement of rod 502. The images are provided to remote station 20. Remote station 20 can provide measurements of rod 502 or related metrics. As shown on display 22, a sagittal Cobb angle, coronal Cobb angle, and axial rotation is provided from the measurement of rod 502 on remote station 20. The surgeon can determine if the provided measurements corresponding to the shape of rod 502 meet the goals and objectives of the surgery. The surgeon can modify rod 502 to change the spine shape to meet the desired outcome and rod 502 can be re-measured to provide metrics indicating the change a change in outcome.

FIG. 28 is side view image 510 and top view image 512 of rod 514 and encoded collar 516 in accordance with an example embodiment. In the example, a distal end of rod 514 is coupled within an opening in encoded collar 516. A finger hold 518 extends from a main body of encoded collar 516. Similar, to the manual method of rotation described hereinabove, finger hold 518 can be held by thumb and fore finger (or other variation) to rotate rod 514 and encoded collar 516. In one embodiment, the camera is held or mounted so the field of view captures the entire length of rod 514 and encoded collar 516. For example, optical measurement probe 12 is held such that the lens of the camera is perpendicular to a surface 564 of encoded collar 516. The camera should be able to capture the identifying markings on the side, top surface 516, or both of encoded collar 516.

The dimensions of encoded collar 516 are known. For example, the height and diameter of the main body of encoded collar 516 is known and provided to remote station 20. Similarly, the height and diameter of finger hold 518 is known. Dimensions of rod 514 can calculated by comparing and scaling to the known dimensions of encoded collar 516 on an image. In one embodiment, encoded collar 516 has identifying markings on around a periphery of the main body of encoded collar 516. In the example, bar codes are used to identify sections of encoded collar 516 and a corresponding portion of rod 514. The periphery of the main body should be visible to the camera as it is spun. A top surface of encoded collar 516 can also included identifying markings that correspond to portions of rod 514. As mentioned the markings on encoded collar 516 are unique in each section and can be recognized by the remote station from images it receives.

Image 510 and image 512 relate to a single image provided by the camera of optical measurement probe 12. It should be noted that approximately 360 degrees of 2D images of rod 514 are provided by the camera of optical measurement probe 12. Each of the 2D images is identified by a unique mark or identifier found on a side or a surface of encoded collar 516 that represents an arc of rod 514. Each image received by the remote station is processed similar to image 510 and 512. The surgeon may not be able to keep rod 514 and encoded collar 516 a constant distance from the camera in optical measurement probe 12. In general, the remote station can detect objects in an image. The remote station also has the ability to scale and rotate image. In one embodiment, the remote station scales the images to each other such that the encoded collar 516 are the same size in each image. The remote station can also rotate each image so they are viewed from the same point of reference. The shape of encoded collar 516 can support the translation process. Encoded collar 516 can have sloped edges and other distinguishing features that can be compared and assessed from image to image by the remote station. The dimensions of the distinguishing features will also be known which will support manipulation of each image to make the encoded collar 516 the same in each image and whereby the dimensions of rod 514 are substantially equivalent and the profile can measured. The images can then be summed together to produce a 3D measurement of rod.

The remote station will project a measurement grid on image 510 to measure a contour of rod 514. The measurement grid comprises a central vertical axis 562 and a plurality of horizontal spaced lines that are perpendicular to central vertical axis 562. The horizontal spaced lines comprise lines 520, 522, 524, 526, 528, 530, 532, 534, 536, 538, and 540. Central vertical axis 562 is perpendicular to a top surface 564 of encoded collar 516. The plurality of spaced lines intersect rod 514 at different points. The points of intersection are points 542, 544, 546, 548, 550, 552, 554, 556, 558, and 560. The number of number of horizontal lines and the intersections points can be more or less than shown. As mentioned previously, the dimensions of encoded collar are known and provided to the remote station. The dimensions of rod 514 can be determined by referencing the known dimensions of encoded collar 516 to the image rod 514. For example, horizontal lines 520, 522, 524, 526, 528, 530, 532, 534, 536, 538, and 540 the spacing between the horizontal lines can represent a distance of 1 centimeter. The horizontal line spacing representing 1 centimeter on image 510 can be scaled from known dimensions of encoded collar 516 on image 510 and using those dimensions to scale the line spacing. Thus, as shown, the height of rod 514 in the example is approximately 10 centimeters. Similarly, the distance of points 542, 544, 546, 548, 550, 552, 554, 556, 558, and 560 from central vertical axis 562 can be scaled and measured by the remote station from the known dimensions of encoded collar 516. Curve fitting can be used between points to generate a shape that approximates rod 514 if needed. As mentioned, encoded collar 516 is rotated which also rotates rod 514. Points 542, 544, 546, 548, 550, 552, 554, 556, 558, and 560 are measured by the remote station throughout a 360 degree rotation of rod 514 from the images provided. The remote station will also log or note key features from the images. For example, the remote station can log and identify where a maximum occurs for each point. The location or position of the point maximum is identified by an angle or the identified arc from encoded collar 516. In general, a table is generated indicating a displacement from central vertical axis 562 of points 542, 544, 546, 548, 550, 552, 554, 556, 558, and 560 on each 2D image and the corresponding position or angular orientation of rod 514 from the identified marking on encoded collar 516 as measured by the remote station. The identified marking on the encoded collar 516 corresponds to an angle. Thus, we can translate to polar notation since we have the radius of the points from the central vertical axis 562 and the angle represented by the marking on encoded collar 516 for the 2D image.

In one embodiment, the table is stored in polar notation that provides a radius from central vertical axis 562 at an angle for each point to define a profile of rod 514. Image 512 represents a top view looking down on rod 514 and encoded collar 516. The circles represent angular change and the orthogonal lines represents the radius from the central vertical axis 562. The table generated by the remote station can be translated to different coordinate systems if required. In one embodiment, the polar coordinates in the table can be translated to Cartesian coordinates. A 3D model of rod 514 can be constructed from the data points in the table. The remote station can use a spline algorithm to interpolate the shape of rod 514 from the table of measured data points. The spline is fitted to the point constellation provided from the table of data points generated from the 2D images. Metrics can be generated from the shape of rod 514 in conjunction with other data stored in the remote station. In one embodiment, the remote station will have the positions of each pedicle screw in the spine and positions of the endplates of each vertebra relative to each pedicle screw. A Cobb angle can be calculated using the information stored in the remote station. The 3D shape of the rod is known from the spline interpolation of the measured data points from the 2D images. The pedicle screws are the coupling points between the rod and the vertebra. The locations of the pedicle screw are known and can be located on the rod. The position of the vertebrae is known on the rod from the pedicle screws. The endplate to pedicle screw relationship is also known by the remote station. Thus, the Cobb angle can be calculated from the position of the most proximal and distal endplates of the region of interest.

Figure 29:
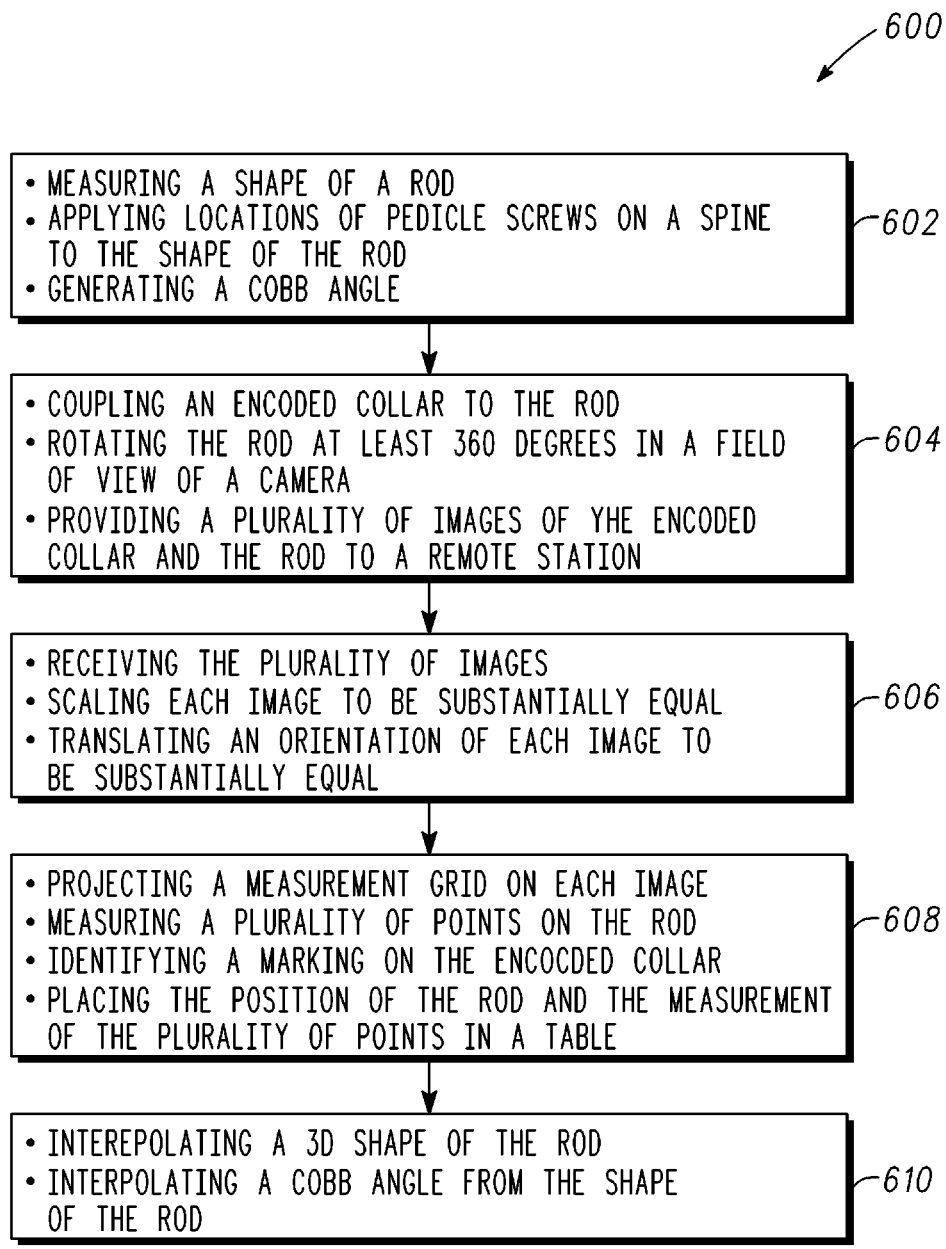
FIG. 29 is a block diagram of a method of measuring a shape of a rod for a spine in accordance with an example embodiment.

FIG. 29 is a block diagram 600 of a method of measuring a shape of a rod for a spine in accordance with an example embodiment. A method of measuring a shape of the rod using a spine measurement system is disclosed. The rod is typically bent by the surgeon. The measured rod shape can be converted to one or metrics that allows a surgeon to determine if the measured rod shape will meet a desired outcome for the patient prior to installation. The rod can be adjusted if the spine outcome is not met by the measured rod shape. The method can be practiced with more or less steps and is not limited to the order of steps shown. The method is not limited to the spine example but can be used for hip, knee, shoulder, ankle, elbow, spine, hand, wrist, foot, bone, and musculoskeletal system. The components listed in the method can be referred to and are disclosed in FIG. 5. In a block 602, a shape of the rod is measured. In one embodiment, the process of measuring the rod is automated where the user requires no measurement tools or takes any measurements. Locations of the pedicle screws in a spine are known. The pedicle screw locations can be stored during a pedicle screw installation process that can be performed using the spine measurement system as disclosed hereinabove. The locations of the pedicle screw are applied to the shape of the rod. The vertebra are positioned to the rod by locating the predetermined points where the pedicle screws couple to the rod. The shape of the spine is determined by the shape of the rod and where the pedicle screws couple to the rod. In one embodiment, the location of the pedicle screw and end plates of the vertebra are known and stored in a remote station. The remote station is also configured to measure a shape of the rod. A Cobb angle can be generated that corresponds to the shape of the rod. In one embodiment, the remote station uses quantitative measurements corresponding to the shape of the rod and pedicle screw locations to calculate the Cobb angle. The surgeon will use the Cobb angle or other metrics to determine if the rod shape will meet the goals of the surgery.

In a block 604, an encoded collar is coupled to the rod. The encoded collar includes markings that correspond to a position of the rod. The rod is rotated at least 360 degrees. The rod is rotated in a field of view of a camera. The camera captures a plurality of images of the rod and encoded collar. In general, the camera can capture a plurality of images as the rod rotates 360 degrees. The 2D images are used to measure a 3D shape of the rod. A marking is identified on the encoded collar in each image relating a position or the rod to a rod profile at the position. The plurality of images of the encoded collar and the rod are provided to a remote station for processing each image.

In a block 606, the plurality of images are received by the remote station. In one embodiment, the remote station is configured to recognize the rod, the encoded collar, and a plurality of markings on the encoded collar. As mentioned previously, a marking corresponds to a position of the rod in each image. Each image is scaled by the remote station. In one embodiment, the remote station has the dimensions of the encoded collar. The remote station is configured to scale images. The remote station scales each image such that the encoded collar is substantially equal in each image. An orientation of each image is translated and rotated to have a substantially equal orientation. The remote station is configured to translate and rotate an orientation of an image.

In a block 608, a measurement grid is projected on each image. In one embodiment, the remote station projects the measurement grid on each image. A plurality of points are measured on the rod. In one embodiment, the measurement grid intersects the rod at multiple points on each image. The intersection of the measurement grid and the rod are the plurality of points on each image. The remote station measures the plurality of points in relation to the measurement grid. For example each point of the plurality of points can be measured from a central axis. A marking is identified on the encoded collar for each image. The position of the rod for each image is identified by the marking on the encoded collar. The measured positions of the plurality of points corresponds to the position of the encoded collar. The position of the rod and the measurement of the plurality of points is placed in a table. The remote station is configured to create the table and store the measurement of the plurality of points and the position of the rod in the table for each image.

In a block 610, a 3D shape of the rod is interpolated. The remote station is configured to use a spline algorithm to interpolate the 3D shape of the rod. A Cobb angle is interpolated from the shape of the rod. The remote station is configured to interpolate the Cobb angle from the 3D shape of the rod and locations of pedicle screws in the spine. In one embodiment, the remote station will have locations of the endplates of each vertebra in relation to the pedicle screws. Thus, the Cobb angle can be calculated as disclosed hereinabove by interpolating the plane of a proximal vertebra endplate and the distal vertebra endplate of the region of interest and measuring the Cobb angle between intersecting planes.

Figure 30:
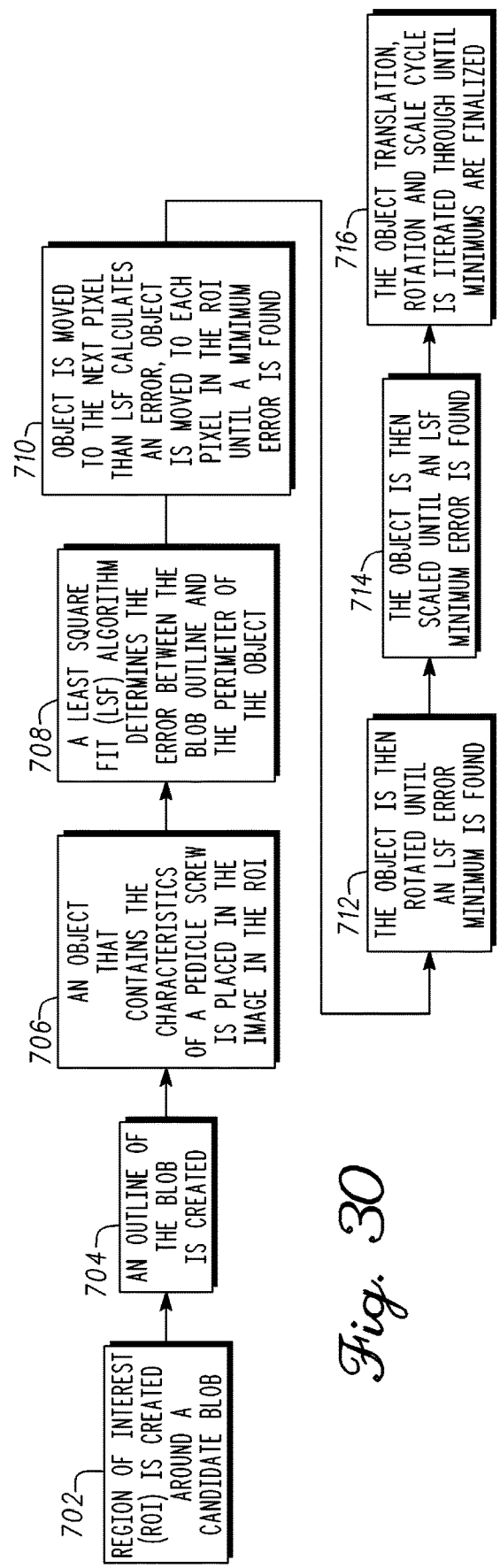
FIG. 30 is a block diagram illustrating using computer vision to identify or recognize an object in accordance with an example embodiment.

FIG. 30 is block diagram 700 illustrating using computer vision to identify or recognize an object in accordance with an example embodiment. In general, computer vision can be to recognize an object. In one embodiment, a computer receiving an image can recognize one or more objects using computer vision software. Similarly, the computer vision software can be run in real-time to identify, recognize, and track objects relative to each other using a camera providing a live feed. There are many different computer vision algorithms that can be used to recognize objects or be optimized for a medical application. For example, some of the computer vision appearance-based algorithms are edge matching, divide and conquer strategy, grayscale matching, gradient matching, histograms of receptive field responses, and large model bases. Similarly, feature based computer vision algorithms can comprise interpretation trees, hypothesize and test, pose consistency, pose clustering, invariance, geometric hashing, scale-invariant feature transform (SIFT), and speeded up robust features (SURF). The appearance-based methods use templates or exemplars of the objects to perform recognition. The feature-based method finds matches between object features and image features. The algorithm used can comprise one or more aspects of the different algorithms listed above.

A method of recognizing an object using the spine measurement system 10 of FIG. 1, FIG. 5, or FIG. 22 is disclosed. The method can be practiced with more or less steps and is not limited to the order of steps shown. The method is not limited to the spine example but can be used for hip, knee, shoulder, ankle, elbow, spine, hand, wrist, foot, bone, and musculoskeletal system. The components listed in the method can be referred to herein below and are disclosed in FIG. 1, FIG. 5 or FIG. 22. In general, a fluoroscope 18 is one source for providing an image of the spine for object recognition such as vertebra endplates or pedicle screws for measurement of angles related to spine shape. Optical measurement probe 12 is another source for providing an image or images. Images are provided to remote station 20 where computer vision software can be used to recognize objects of interest related to the spine. In one embodiment, remote station 20 is a computer that can be local to the operating room or be located remotely. Furthermore, remote station 20 can recognize, analyze, and generate quantitative measurements in real-time related to spine shape for use by the surgeon or operating team in the operating room.

In a step 702 a region of interest (ROI) is created around a candidate blob. In one embodiment, one or more digital images are provided to the computer (e.g. remote station 20) executing computer vision software. A blob is a portion of a digital image where differences in properties can be used for detection and where other properties can be similar. Examples of differing properties are brightness or color in an image. In general, blob detection can be used to detect the region of interest where specific objects are being recognized. In the example, the identified blobs have a high probability of being the objects being identified on the digital image. The computer will have information and data related to the objects to be recognized. Once the region of interest is identified further processing can performed. In one embodiment, object recognition is performed. The object can then be tracked after being recognized by the computer.

Figure 31:
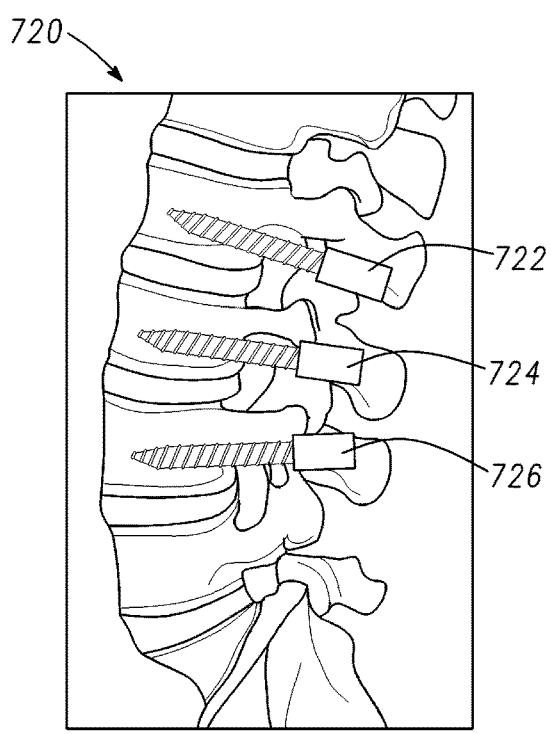
FIG. 31 is a lateral fluoroscope image of a portion of a spine showing pedicle screws in vertebrae in accordance with an example embodiment.
Figure 32:
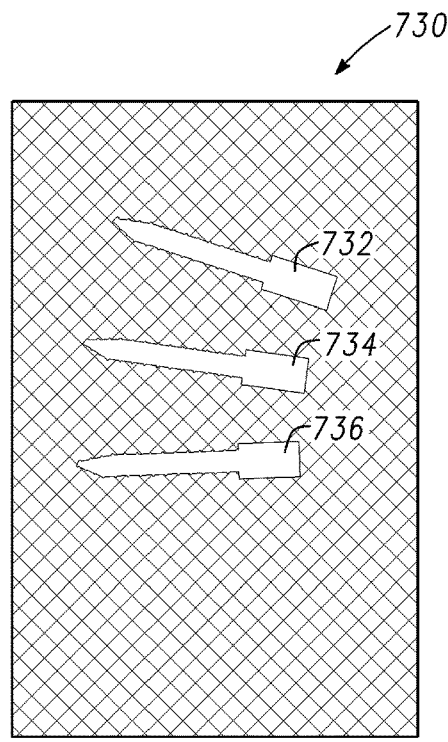
FIG. 32 is a binary image of FIG. 31 showing pedicle screws in accordance with an example embodiment.

An example, of recognizing one or more pedicle screws will be used to illustrate a computer vision process for spine measurement system 10. Referring briefly to FIG. 31, a fluoroscope image 720 of a lateral view of a spine is shown. A digital image of fluoroscope image 720 is provided to the computer. Pedicle screws 722, 724, and 726 can be seen within image 720. In one embodiment, end plates of each vertebra will also be recognized from fluoroscope image 720. Referring briefly to FIG. 32, a binary image 730 of the fluoroscope image is created by the computer. The regions of interest are shown in white on binary image 730. For example, a threshold is set where pixels having a brightness above a threshold are converted to white on binary image 730. Conversely, pixels have a brightness below the threshold are converted to black on binary image 730. Converting to binary image 730 yields multiple objects comprising the white portions of the image. As mentioned previously, we are trying to recognize pedicle screws in the fluoroscope image 720. Binary image 730 yields three large white regions 732, 734, and 736 with several smaller white regions. The computer includes information related to different types of pedicle screws and characteristics of each type. The smaller white regions can be eliminated as not being candidates for pedicle screws.

Figure 33:
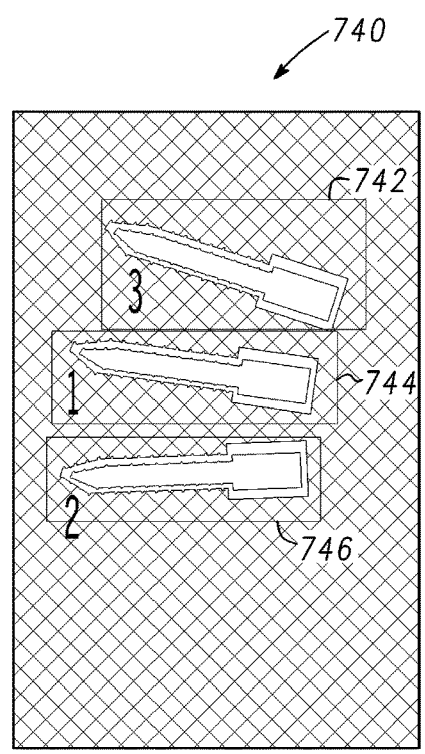
FIG. 33 is an image showing regions of interest in accordance with an example embodiment.

In a step 704, an outline of the blobs are created. The computer identifies regions of interest that could possibly be pedicle screws. Referring briefly to FIG. 33, regions of interest are shown with boxes 742, 744, and 746 surrounding each blob. An outline of each blob within boxes 742, 744, and 746 is highlighted or enhanced to show the shape of each blob. In one embodiment, an effective shape descriptor can be used for pattern recognition. One type of contour-based shape descriptor are regular moment invariants of which one set is known as a Hu moment invariant algorithm. The Hu moment invariant algorithm is applied to the blobs to describe each object despite the location, size, or rotation. Alternatively, a Zernike Moment can be used. For example a blob descriptor can have a particular weighted average moment of the image pixels' intensities that represent or characterize a blob.

In a step 706, an object that contains the characteristics of a pedicle screw is placed is within the regions of interest. The object is represented similarly to the blob whereby the object and the blobs can be compared. In the example, the object is the pedicle screw. In one embodiment, the object and blobs are represented by pixels. In a step 708, a least square fit (LSF) algorithm determines the error between the blob outline and the perimeter of the object (example—pedicle screw). In a step 710, the object is moved to the next pixel then the LSF algorithm calculates the error. The process continues where the object is moved pixel by pixel in the ROI until a minimum error is found. In a step 712, the object is then rotated until a least squares fit error minimum is found. In a step 714, the object is then scaled until a least squares fit error minimum is found. In a step 716, the object translation, rotation, and scale cycle is iterated through until all minimums are finalized for each region of interest. At this point the object is fitted to the blob. The process disclosed above can be used by the spine measurement system 10 in assessing fluoroscope images, an image provided by optical measurement probe 12, or images provided in real-time by optical measurement probe 12.

Figure 34:
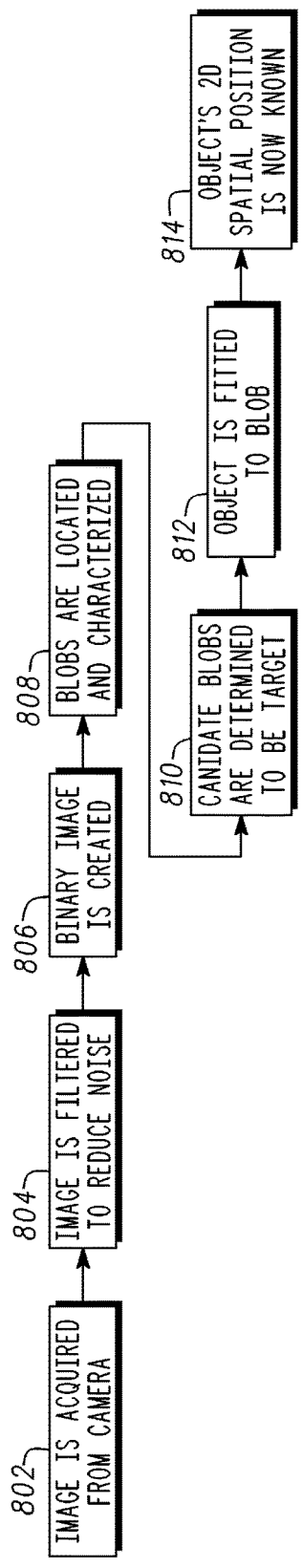
FIG. 34 is a block diagram illustrating the use of computer vision for pedicle screw or vertebra identification from a fluoroscope image or an image provided by an optical measurement probe in accordance with an example embodiment.

FIG. 34 is block diagram 800 illustrating the use of computer vision for pedicle screw or vertebra identification from a fluoroscope image or an image provided by an optical measurement probe in accordance with an example embodiment. A method of recognizing an object using the spine measurement system 10 of FIG. 1, FIG. 5, or FIG. 22 is disclosed. The method can be practiced with more or less steps and is not limited to the order of steps shown. The method is not limited to the spine example but can be used for hip, knee, shoulder, ankle, elbow, spine, hand, wrist, foot, bone, and musculoskeletal system. The components listed in the method can be referred to herein below and are disclosed in FIG. 1, FIG. 5 or FIG. 22. In general, a fluoroscope 18 is one source for providing an image of the spine for object recognition such as vertebra endplates or pedicle screws for measurement of angles related to spine shape. Optical measurement probe 12 is another source for providing an image or images. Images are provided to remote station 20 where computer vision software is run to recognize pedicle screws, vertebra, vertebra landmarks or features, and spine landmarks or features. Block diagram 800 can use the computer vision steps disclosed in FIG. 30.

In a step 802, an image is acquired from the camera (e.g. optical measurement probe 12). In the example, an image is taken of monitor 26 of fluoroscope 18 by optical measurement probe 12. The image of a fluoroscope image is received by remote station 20 from optical measurement probe 12. In a step 804, the image is filtered to reduce noise. This reduces noise introduced by system 10 such as the imaging sensor of the camera. In a step 806, a binary image is created. The binary image highlights regions of interest related to the objects to be recognized on the image. For example, pedicle screws, vertebra landmarks, or vertebra endplates can be targets for the computer vision recognition. In a step 808, blobs are located and characterized. In the example, blobs corresponding to pedicle screws, vertebra, or vertebra landmarks can be located. In a step 810, candidate blobs are determined to be targets. In general, the candidate blobs are selected as having a high degree of probability of being the object to be recognized. A Hu algorithm can be executed on the candidate blobs to put them in a mathematical form where they can be compared. In a step 812, the object being recognized is fitted to each blob. The object has a mathematical model or form where the candidate blobs and the object can be compared. It should be noted that the computer has the dimensions and shape of the object as well as other object descriptors. The fitting process can require translation, rotation, or scaling of the object. The fitting process places the object to the blob having a minimum error. In a step 814, the object's 2D spatial position is now known. In general, the amount of translation, rotation, and scaling of the object defines the spatial position. The positions relative to other recognized objects is also known. Thus, specific objects within the image have been identified and their position, rotation, and scaling are also known on the image relative to one another.

In the pedicle screw example the computer vision program knows that there is a threaded region and a head region of the screw. The program further knows that only the threaded region is screwed into bone of the vertebra. The head region is outside the vertebra. The program can focus on the threaded region of the blob and fitting the threaded region of the object to the blob in this part of the region. As mentioned previously, the program knows the dimensions of the pedicle screw and more specifically the threaded region of the pedicle screw. The computer vision program can then recognize the vertebra and details of the vertebra (such as end plates) since the vertebra has a dimensional and spatial position relative to an installed pedicle screw. For example, the computer vision program can recognize endplates of the vertebra in relation to the threaded region of the pedicle screw using information generated in recognizing the pedicle screw and knowing where the endplates should be in relation to the pedicle screw.

Figure 35:
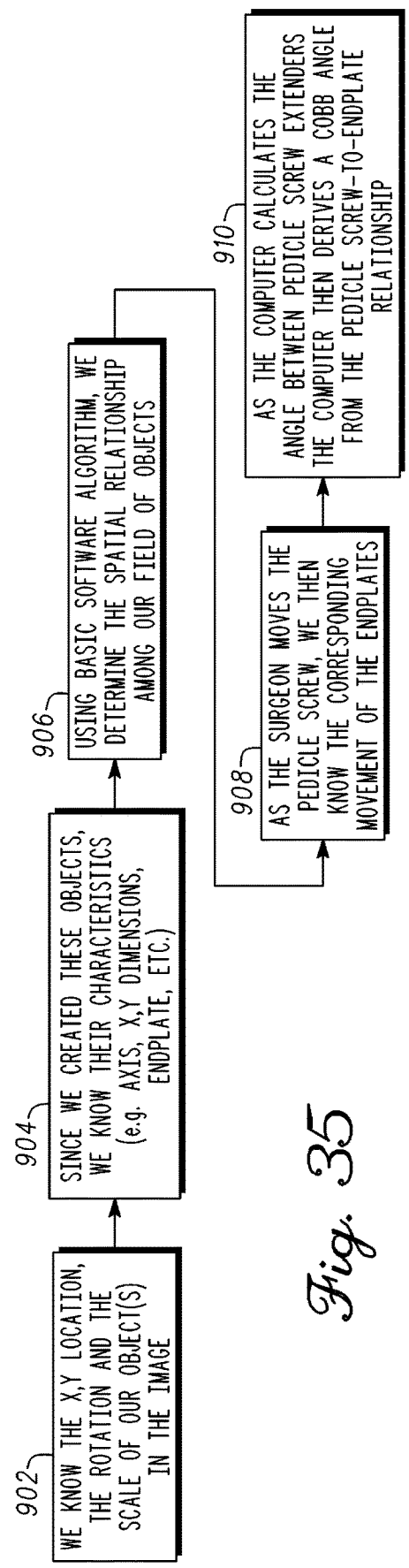
FIG. 35 is a block diagram illustrating a Cobb angle measurement in accordance with an example embodiment.

FIG. 35 is block diagram 900 illustrating Cobb angle measurement in accordance with an example embodiment. FIG. 34 discloses recognizing pedicle screws and vertebra endplates using computer vision software. Included in the recognition process is a fitting process that translates, rotates, and scales the object to the blob in the image whereby the position of the object is known. The components listed in FIG. 1, FIG. 5 or FIG. 22 can be used in the process. Similarly, steps in FIG. 30 and FIG. 34 can be used in block diagram 900. In a step 902 and disclosed in FIG. 34, the X,Y location, the rotation, and the scale of the objects recognized in the image provided by optical measurement probe 12 to remote station 20 is known. In one embodiment, the spine is manipulated in real-time by a surgeon. Optical measurement probe 12 provides images of pedicle screw extenders coupled to vertebra of the spine. Computer vision software is then used to measure the Cobb angle as disclosed herein below.

In a step 904, remote station 20 has stored in memory the characteristics of each recognized object. In general, the objects have known characteristics and features that are used in the computer vision program executed by the computer. Characteristics such as an axis of the object or X,Y dimensions of the object are known. Similarly, a feature such as endplates of vertebra or landmarks on vertebra are known. Also, spacing or angles between characteristics are known such as pedicle screw to endplate angles. In the example, pedicle screws are placed in vertebra of the spine. Pedicle screw extenders are coupled to the pedicle screws. The pedicle screw extenders are in the field of view optical measurement probe 12 of the spine measurement system. Remote station 20 running computer vision receives image data from optical measurement probe 12. The computer vision software recognizes each pedicle screw extender. As a surgeon manipulates the spine to change spine shape, the pedicle screw extenders will move. In a step 906, a software algorithm is used to determine the spatial relationship among the field of objects recognized by the computer vision software. In a step 908, the surgeon manipulates the spine thereby moving the pedicle screw extenders. As disclosed the pedicle screw extender couples to a pedicle screw. The characteristics of the pedicle screw extender are known. The computer vision software can use the characteristics of the pedicle screws extenders to locate the heads of the pedicle screws to which they couple and the threaded region of the pedicle screws in each vertebra. Remote station 20 can relate the threaded region of the pedicle screw to a vertebra and a vertebra features such as the endplates of the vertebra. Thus, the movement of the pedicle screw extenders can be related to movement of the endplates using computer vision. In a step 910, as the system calculates the angle between pedicle screw extenders the computer then calculates Cobb angle from the pedicle screw to endplate relationship. The pedicle screw to endplate angles are known and can be used with the pedicle screw extender angles to calculate the Cobb angle.

FIG. 36 is block diagram 1000 illustrating a tracking of targets such as pedicle screw extenders in accordance with an example embodiment. FIG. 35 disclosed a process of recognizing pedicle screws, vertebra, vertebra endplates, and landmarks using computer vision software. Included in the recognition process is a fitting process that translates, rotates, and scales the object to the blob in the image whereby the position of the objects are known relative to one another. The components listed in FIG. 1, FIG. 5 or FIG. 22 can be used in the process. Similarly, steps in FIG. 30 and FIG. 34 can be used in block diagram 1000.

Pedicle screw extenders are coupled to pedicle screws. Each pedicle screw is screwed into a vertebra. As mentioned previously, the pedicle screw extenders are targets that can be recognized by the computer vision software executed on the computer. The pedicle screw extenders can have 2D or 3D markings to support the measurement of position and rotation of each target. In a step 1002, an image is acquired from a camera. In one embodiment, the pedicle screw extenders are in a field of view of optical measurement probe 12. Optical measurement probe 12 is coupled to remote station 20 for processing image data using computer vision software. In a step 1004, the image is filtered to reduce noise. In one embodiment, the noise is generated by the image sensor of the camera. In a step 1006, a binary image is created. As disclosed above, a threshold is determined that supports recognition of an object (e.g. pedicle screw extender). The pixels are converted to either black or white. In a step 1008, "blobs" are located and characterized within region of interests (ROI). In one embodiment, the blobs are white in the binary image. In a step 1010, candidate blobs are determined to be targets. In general, blobs that do not have the characteristics of a pedicle screw extender are eliminated. In a step 1012, region of interests are created. Each region of interest is located around a blob that has a high probability of being the object. In the example, each region of interest comprises a blob corresponding to a pedicle screw extender. In a step 1014, the object is fitted to the blob. In this process the pedicle screw extender is fitted to blob. The fitting process can include a least square fit algorithm that determines the error between the blob outline and the perimeter of the pedicle screw extender. The pedicle screw extender is moved pixel by pixel with a least square fit being calculated with each movement until a minimum error is found. Similarly, the pedicle screw extender is scaled, translated, and rotated until least square fit minimums are finalized. In a step 1016, the 3D pose is derived. In general, a 3D pose estimation determines the transformation of the pedicle screw extender (or target) in 2D and yields the pedicle screw extender in 3D. The pose estimation can comprise SolvePnP, SOlvePnPRANSAC, or other type of pose estimator. The 3D pose estimation or algorithm can estimate the 3D rotation and translation of the pedicle screw extender from a 2D image using a 3D model of the pedicle screw extender. The dimensions and features of the pedicle screw extender are known. Also used in the pose algorithm are the related points between the 2D image and the 3D model. The 3D pose will place each pedicle screw extenders in relation to each other in 3D space. The angle between pedicle screw extenders can be measured by the computer. The location of each pedicle screw can be calculated from a corresponding pedicle screw extender as the position, rotation, and dimensions of the pedicle screw extender are known. The system includes pedicle screw data, pedicle screw installation data, and angle data from previous measurements which can also be used in the calculations. Similarly, the position of the vertebra or vertebra endplates can be calculated from the location of the pedicle screw. Thus, knowing the position of each pedicle screw extender in 3D space determines the position of each corresponding vertebra in relation to one another. A Cobb angle and other angles/rotation can be calculated that provide a measure of the spine shape in real-time using the computer vision software. LLR measured absolute positions with respect to the camera coordinate system.

FIG. 37 is block diagram 1100 illustrating a pose derived 3D location in space from a 2D image in accordance with an example embodiment. The components listed in FIG. 1, FIG. 5 or FIG. 22 can be used in the process. The steps in FIG. 30 and FIG. 34 can be used in block diagram 1100. One or more targets are in the field of view of optical measurement probe 12. A camera in optical measurement probe 12 provides images to a computer executing computer vision software. In one embodiment, the targets have images on them. For example, the images can be a plurality of circles where each circle has a different diameter. The dimensions of each circle are provided to the computer.

In a step 1102, a 3D object will display a distorted 2D image if the object is rotated away from the front plane of the camera. The rotation of the object can be calculated based on the distortion of the images on the target. In the example, rotation away from the front plane of the camera would make the circles appear as ellipses. The shape of the ellipses would correspond to the amount of rotation away from the front plane of the camera. In a step 1104, a 3D object's image will change scale proportionally with the distance from the camera. In general, increasing a target distance from the camera will proportionally reduce the size of the images on the target as seen by the camera. Conversely, decreasing a target distance from the camera will proportionally increase the size of the images on the target as seen by the camera. The relational distance of the targets can be determined using the known scaling. In a step 1106, a 3D object rotated around the target to camera axis will be obvious. The position of the object is noted in relation to the target or targets. In a step 1108, the pose algorithm will "move" the camera's perspective (virtually) until the image is an exact fit to a trained image. In one embodiment, the pose algorithm will "move" the camera's perspective spherically until the ellipses seen on the target become circles. The pose algorithm then knows the position of the target. Similarly, from the size of the circles we can determine the distances. In a step 1110, the movements of the camera perspective creates X, Y, Z dimension and X, Y, Z rotation output yielding 6 degrees of freedom data.

Figure 38:
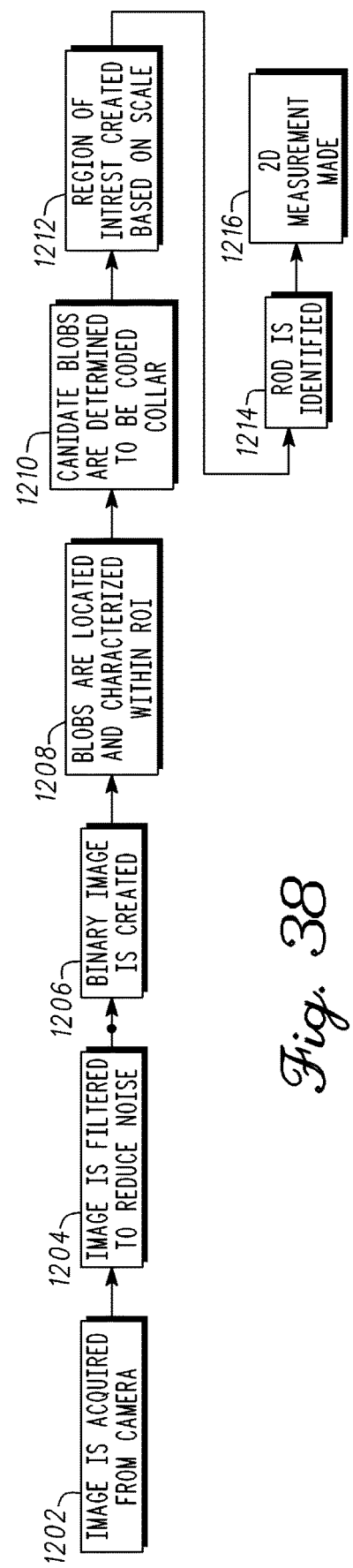
FIG. 38 is block diagram illustrating a rod measurement in accordance with an example embodiment.

FIG. 38 is block diagram 1200 illustrating a rod measurement in accordance with an example embodiment. The components listed in FIG. 1, FIG. 5 or FIG. 22 can be used in the process. The steps in FIG. 30 and FIG. 34 can be used in block diagram 1100. A rod for the spine is placed in a field of view of optical measurement probe 12. An encoded collar is placed on the rod. The dimensions of the encoded collar is provided to the computer for reference. The encoded collar has markings that can be read by a computer and corresponds to an angular orientation of the rod. A camera in optical measurement probe 12 provides images to a computer executing computer vision software. The rod is rotated at least 180 degrees. In one embodiment, the rod and encoded collar is rotated one or more revolutions in the field of view of optical measurement probe 12. The rod can be rotated by hand or by a machine. The camera will take a plurality of images during a single revolution of the rod. For example, 20-360 images can be taken during a single rotation.

In a step 1202, an image is acquired from the camera. The image is provided to a computer executing computer vision software. In one embodiment, the camera is coupled to the computer to provide a plurality of pictures during the rotation. In a step 1204, the image is filtered to reduce noise. In one embodiment, noise from the imaging sensor is removed. In a step 1206, a binary image is created. The binary image will include the encoded collar. In a step 1208, "blobs" are located and characterized within regions of interest. In a step 1210, candidate blobs are determined to be an encoded collar. In a step 1212, a region of interest is created based on scale. In a step 1214, the rod is identified. In a step 1216, a 2D measurement is made. The process is repeated for each image taken by the camera. Further detail on measuring the rod can be found in FIG. 29.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing a patient's Quality Of Life or the life and usability of an implanted orthopedic device.

Figure 39:
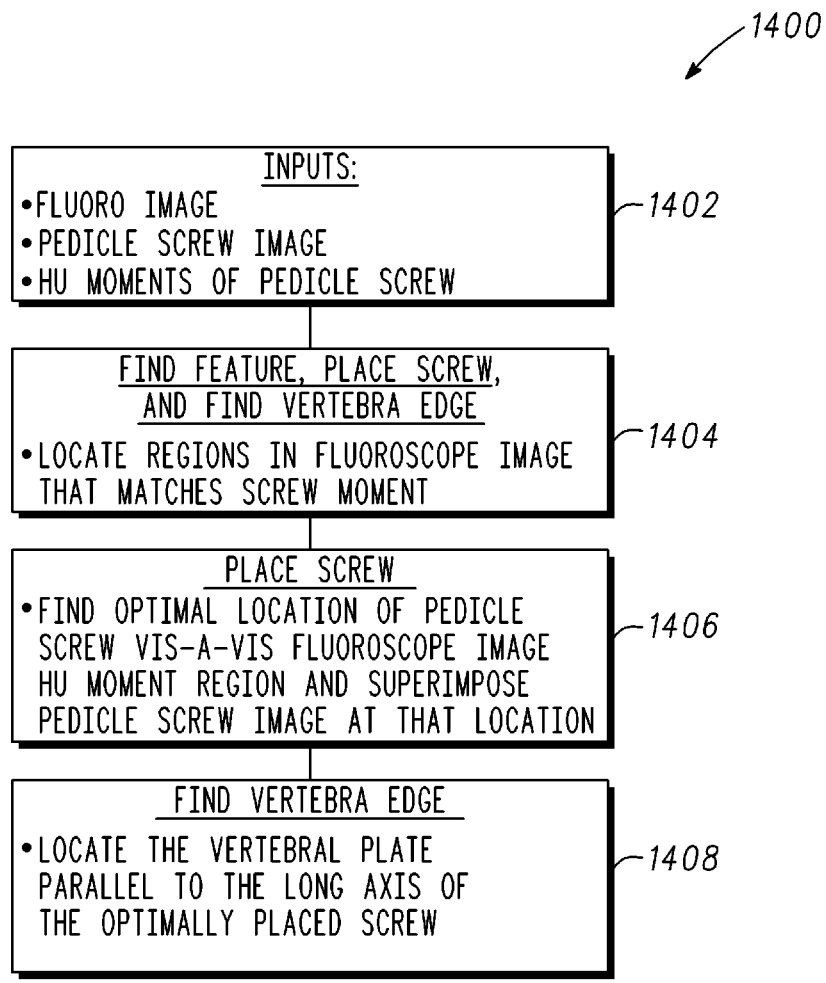
FIG. 39 is block diagram of an automated orthopedic process using one or more fluoroscope images to locate musculoskeletal structures or orthopedic devices and the position of each structure or device relative to one another to generate quantitative measurement data in accordance with an example embodiment.

FIG. 39 is block diagram 1400 of an automated orthopedic process using one or more fluoroscope images to locate musculoskeletal structures or orthopedic devices and the position of each structure or device relative to one another to generate quantitative measurement data in accordance with an example embodiment. The order of the blocks is not fixed and can be placed in any sequence. In general, the automated orthopedic process uses computer vision to identify musculoskeletal structures or orthopedic device from one or more fluoroscope images. In the one embodiment, a weighted average moment is applied to the image to describe an object. The image moment can correspond to pixel intensity or the change in intensity of the pixel intensity. The image moment is used to identify objects in the image. The system supports identification of musculoskeletal structures or orthopedic devices even though the shapes and sizes of a musculoskeletal can vary throughout the population. In one embodiment, data related to the orthopedic devices is provided to the computer and computer vision software to support identifying the object in an image. Examples of an orthopedic device are prosthetic components, screws, or other devices that are temporarily or permanently coupled to the musculoskeletal system.

A system used in orthopedic surgery is shown in FIG. 1 and described herein above. For example, the system can be used to identify a musculoskeletal structure or an orthopedic device from a fluoroscope image. The system can produce quantitative measurement data that can be during surgery. In one embodiment, the measurement data can relate to alignment or position of structures or devices in the musculoskeletal system. In the example disclosed herein, vertebrae of the spine can be identified, the position of each vertebra in relation to other vertebra can be measured, and a measurement such as spine curvature can be measured. Furthermore, orthopedic devices such as pedicle screws can be identified in the fluoroscope image along with each vertebra. The positional relationship between a pedicle screw and a vertebra can be identified and the positional relationship can be used in other applications as the position relative to one another is permanent. Thus, knowing a location of the pedicle screw also determines the location of the vertebra to which it couples.

The automated orthopedic process 1400 can use the components of measurement system 10 of FIG. 1 to identify musculoskeletal structures and/or orthopedic devices. Orthopedic process 1400 can be used for any musculoskeletal structure or orthopedic device to be identified within a fluoroscope image. An example is provided in process 1400 where the musculoskeletal structures are vertebra and the devices are pedicle screws that are screwed into vertebra. In a block 1402, inputs are provided to the measurement system. In general, the measurement system includes a computer. The computer includes software, memory, and a display to support orthopedic process 1400. The computer can receive and process data, run programs, perform calculations, and apply a computer vision program that acquires, processes, and analyzes images related to the musculoskeletal system for use in a medical or surgical environment in real-time. The input to the system comprises one or more images of the musculoskeletal structures and/or devices. In the example, the image is a fluoroscope image. Examples of other image types are MRI, CT, Ultrasound, and X-Ray to name a few types of images that can be provided to measurement system 10. The fluoroscope image can be directly ported to the computer from the fluoroscope or a camera in the orthopedic measurement system can be used to take an image of the fluoroscope image that is provided to the computer. In either case, one or more fluoroscope images are provided to the computer. In the example the fluoroscope image is an image of vertebrae of the spine. The fluoroscope image can further include pedicle screws that have been placed into the vertebrae. Image moments are provided to the measurement system. In the example, the image moments can describe pedicle screws. In one embodiment, Hu moments are used to describe the pedicle screws. The Hu moments can be used in conjunction with other image moments. The advantage of using Hu moments is that they can be invariant under translation, scale, and rotation. Alternatively other image moments could be used. The computer will also have data and information on the type of pedicle screw being used. The data and information includes the dimensions and shape of a pedicle screw being used as well as other descriptive metrics that can be used in process 1400.

In a block 1404, features are found in the fluoroscope image. The block 1404 receives inputs from block 1402. In general, the image moments are used to locate regions in the fluoroscope image having similar characteristics. In the example, the computer and computer vision software identifies regions where the Hu moments of the pedicle screws correspond to what is seen in the fluoroscope image. Part of what is done is by the computer vision software is fitting by translation, rotation, and scaling to fit the pedicle screw image. In a block 1406, the musculoskeletal structure or device is superimposed in the regions found in block 1404 corresponding to the image moments. In the example, optimal locations of pedicle screws are identified vis-à-vis fluoroscope image Hu moment regions. The pedicle screw image can then be superimposed by the computer and computer vision software at the identified locations. Thus, the pedicle screws have been identified in the image and that can be corroborated by a user of the system from looking at the superimposed musculoskeletal structures or orthopedic devices. In the orthopedic device (pedicle screw) is fastened to a musculoskeletal structure (vertebra). The musculoskeletal structure is located in the next step. In a block 1408, a feature of the musculoskeletal system is identified. In the example, a vertebra edge is found. The vertebra edge in the fluoroscope image corresponds to a vertebra end plate. The vertebral plate is located by the computer and computer vision software on the fluoroscope image. A vertebra is bounded by two endplates. In one embodiment, the vertebral plate is parallel to the long axis of the optimally placed pedicle screw. The relationship between a vertebra and pedicle screw(s) is now known by the computer and computer vision software. In one embodiment, a user can view and approve that the computer vision software has identified the components of interests.

Figure 40:
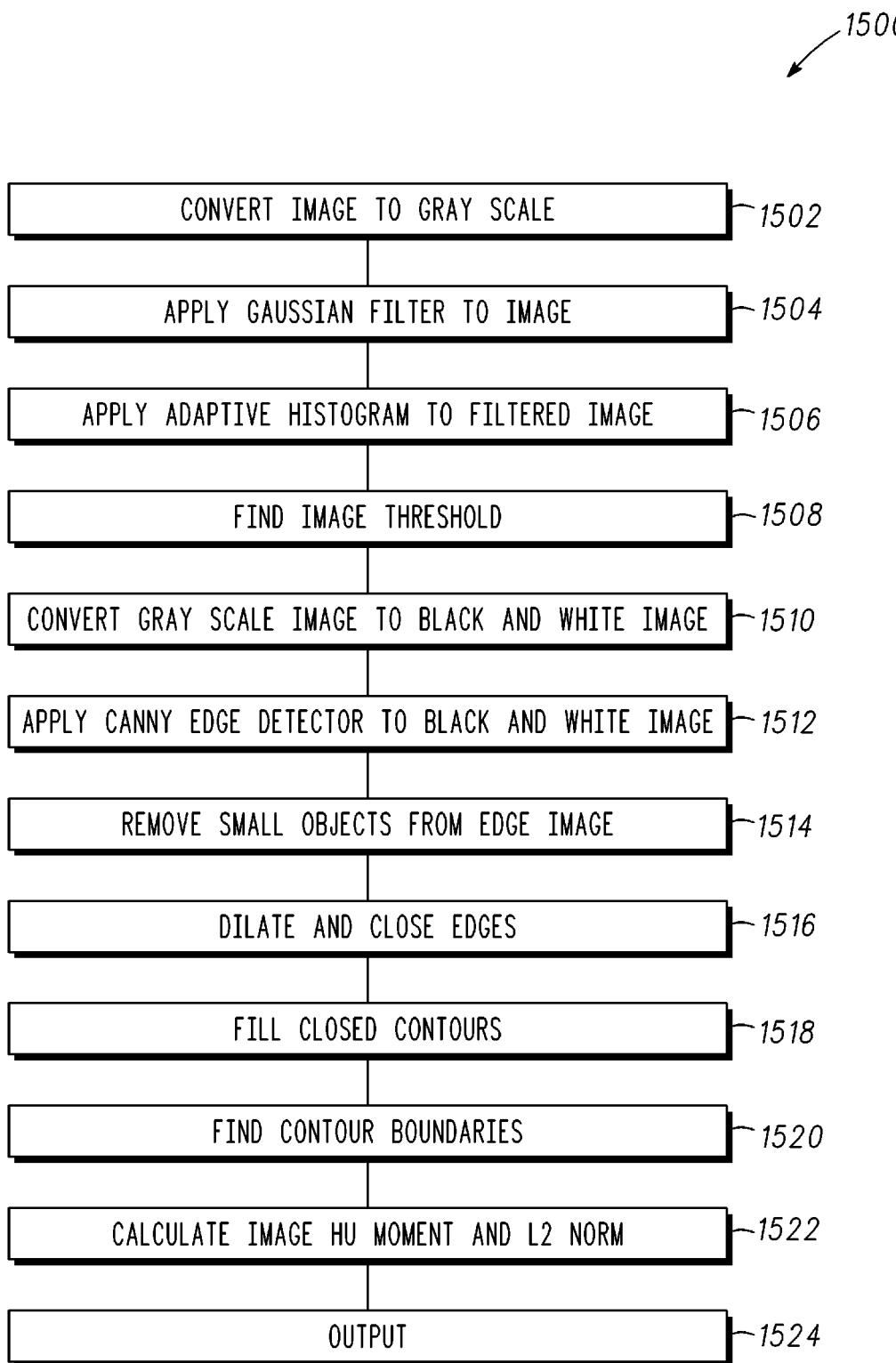
FIG. 40 is a block diagram illustrating steps involved with a computer and computer vision software to identify musculoskeletal structures or devices in one or more images provided to the computer in accordance with an example embodiment.

FIG. 40 is a block diagram 1500 illustrating steps involved with a computer and computer vision software to identify musculoskeletal structures or devices in one or more images provided to the computer in accordance with an example embodiment. Block diagram 1500 provides more detail corresponding to the block diagram 1404 of FIG. 39. In general, block diagram 1500 illustrates steps to find a musculoskeletal structure or an orthopedic device in an image. For example, system 10 of FIG. 1 includes computer vision software that can find a feature in an image captured by system 10. The order of the blocks are not fixed and can be performed in any sequence. In the example, one or more fluoroscope images are provided to the computer. In block

1502, an image received by the computer is converted to grayscale. In one embodiment, the image is a digital image. In the example, the image received is a digital fluoroscope image. In general, grayscale is a range of shades of gray. Within the grayscale the lightest possible shade is white while the darkest shade is black. The converted image can include wide variations corresponding to different grayscale shades. In block 1504, a filter is applied to the grayscale image generated in block 1502. Morphological image processing comprises non-linear operations related to the shape of features in the image. Morphological operations can comprise erosion, dilution, Gaussian filtering, and Laplacian filtering. In one embodiment, a Gaussian filter is applied to the grayscale image. Alternatively, other filter types could be used on the grayscale image. A Gaussian filter removes high frequency components or noise from an image and corresponds to a low pass filter. Furthermore, the Gaussian filter can soften hard edges of the image. The impulse response of a Gaussian filter is a Gaussian function. In one embodiment, an image algorithm to enhance a grayscale image comprises subtracting a blurred version of an original grayscale image from another, less blurred version of the original grayscale image. The blurred images are formed by convolution. For example, two blurred grayscale images can be created by convolving the original grayscale image with Gaussian kernels comprising different standard deviations. Gaussian kernals can also be used to quantify the image so features, size, rotation, etc. of a musculoskeletal structure or device can be detected.

Figure 47:
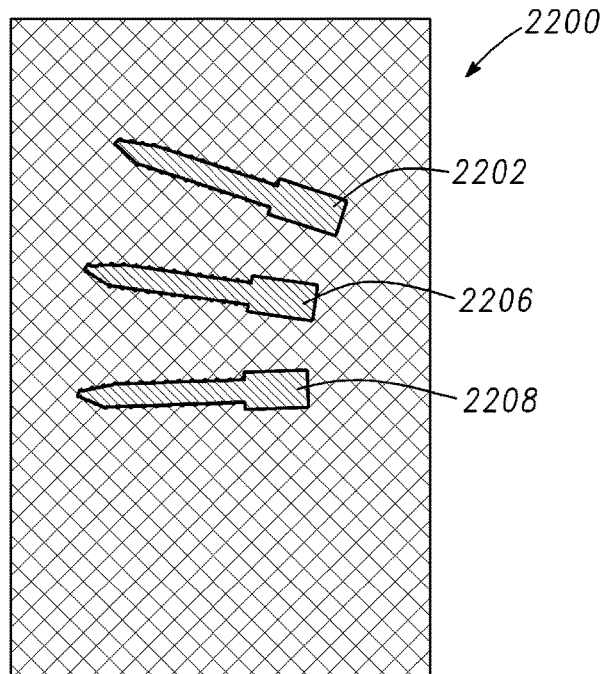
FIG. 47 is an illustration of three pedicle screws where an edge detection algorithm was applied to the image.

In block 1506, equalization is applied to the filtered grayscale image of 1504. Equalization can be used to improve the contrast in images. In one embodiment, an adaptive histogram is applied to the filtered image of the musculoskeletal structures or the orthopedic devices. Alternatively, other equalization could be used. In block 2104, equalization is applied to the grayscale image of block 2102. The equalization is applied to improve contrast on the grayscale image to support identification of the musculoskeletal structures or orthopedic devices. A histogram is created of the entire image's intensity value, then a scaling factor is applied to each bin so that the distribution across the intensity range matches a pre-determined profile. The bin scaling factor is then applied to each corresponding pixel intensity in the image thereby normalizing the image contrast. For example, some images might have high peaks clustered around a value of 90-120, the algorithm will increase 0-89 and 121-255 and reduce 90-120. In block 1508, an image threshold is found or identified after equalization was applied in block 1506. The image threshold corresponds to a point where pixels having a brightness above the threshold are converted to white and all pixels below the threshold are converted to black. The image threshold is used to support identification or locating a musculoskeletal structure or orthopedic device in an image. Image thresholding can be binary, gray scale, adaptive histogram, or other type. In the example, the threshold is selected to support locating pedicle screws in the image. In block 1510, the grayscale image is converted to a black and white image after selecting the threshold in block 1508. The black and white image can also be called a binary image. In one embodiment, the musculoskeletal structure or orthopedic device in the binary image is in white. In the example, the pedicle screws images are white in the binary image. In block 1512, an edge detector algorithm is applied to the black and white image created in block 1510. In one embodiment, a Canny edge detection algorithm is used on the black and white image. Alternatively, Sobel, Roberts, Prewitt, Laplacian, or other edge detection algorithms can be used. The edge detection algorithm characterizes boundaries that support identification of the musculoskeletal structure or device. In general, the edges correspond to areas of high contrast. In the example, the pedicle screw will have screw threads for cutting into bone and holding the screw in place. The screw threads are a high contrast region where the pixel intensity can vary significantly over a small range of the image. The Canny edge detection algorithm has low error rate in detecting edges. Moreover, the Canny edge detection algorithm does not detect non-edges, identifies edges that are localized, and has one response for a single edge. Referring briefly to FIG. 47, an edge detection algorithm is applied to a black and white image to yield a Canny edge image 2200. The Canny edge image 2200 contains the binary image of the pedicle screws. Pedicle screws 2202, 2206, and 2208 are shown displaying the edges identified by the edge detection algorithm.

Further processing is performed by the computer and computer vision software to support finding features of the musculoskeletal structure or orthopedic device. In block 1514, small objects are removed from the edge detected black and white image of block 1512. After the edge detection algorithm has been run on the binary image there may be small objects identified in the image that cannot possibly be the musculoskeletal structures or orthopedic devices. As mentioned, the objects being identified are pedicle screws. In one embodiment, objects are removed from the image that do not have the size or shape of a pedicle screw. In block 1516, the objects are dilated and the edges are closed after the small objects have been removed in block 1514. In general, applying a dilation process or algorithm to the identified objects in the image will "grow" the feature. For example, after running an edge detector algorithm and applying dilation, the edges of the object(s) can thicken. Dilation can also close the gaps between edges that are close to one another. To illustrate further, a region of a predetermined size can be centered on a pixel. The dilation algorithm would make the pixel white if a white pixel is found anywhere within the region thereby "growing" or "filling" the feature. In the pedicle screw example, the outline or edge of the screws in the image can be made contiguous by the dilation algorithm. In block 1518, a fill closed contours process or algorithm is used to fill in continuously closed features after applying dilation in block 1516. In general, "blobs" are formed corresponding to the musculoskeletal structure or orthopedic devices found in the image. In the example, a "blob" corresponds to a pedicle screw that is found in the image. The fill closed contours process can eliminate any nested closed contours to make a single entity. In block 1520, the contour boundaries are found after the closed contours are filled in block 1518. This process or algorithm creates a single entity outline from what could have been multiple entities nested within each other. In block 1522, loop processing is performed on boundaries in the image. In general, the musculoskeletal structure or orthopedic device in the image is identified as a single entity, a "blob" is created on the single entity, and a transform is applied and matches the result with the template values. The computer and computer vision program when looping on boundaries can include filling regions closed by boundaries, compute image moments for regions, compute L2 norm of image moment of the region, compute image moment of musculoskeletal structure or device, save in memory the boundary information, and save in memory the image moment for the region. In the example, each of the identified pedicle screws comprise a single entity, a "blob"

is created of each pedicle screw, a Hu transform is applied to each pedicle screw wherein the result of the Hu transform matches the template values of the pedicle screw. In block 1524, an output is provided by the computer and computer vision software. The output can comprise the X and Y location of the centroid of the identified musculoskeletal structure or device and the rotation and scale of the musculoskeletal structure or device. The computer and computer vision software then places a UI object on top of the captured image. The output can further include an image converted to a binary image, a boundary list, boundary labels, image moments for all regions, the number of found musculoskeletal structures or devices, and image moments for found musculoskeletal structures or devices. The user can then agree or disagree that the identified musculoskeletal structures or orthopedic devices have been correctly identified.

Figure 41:
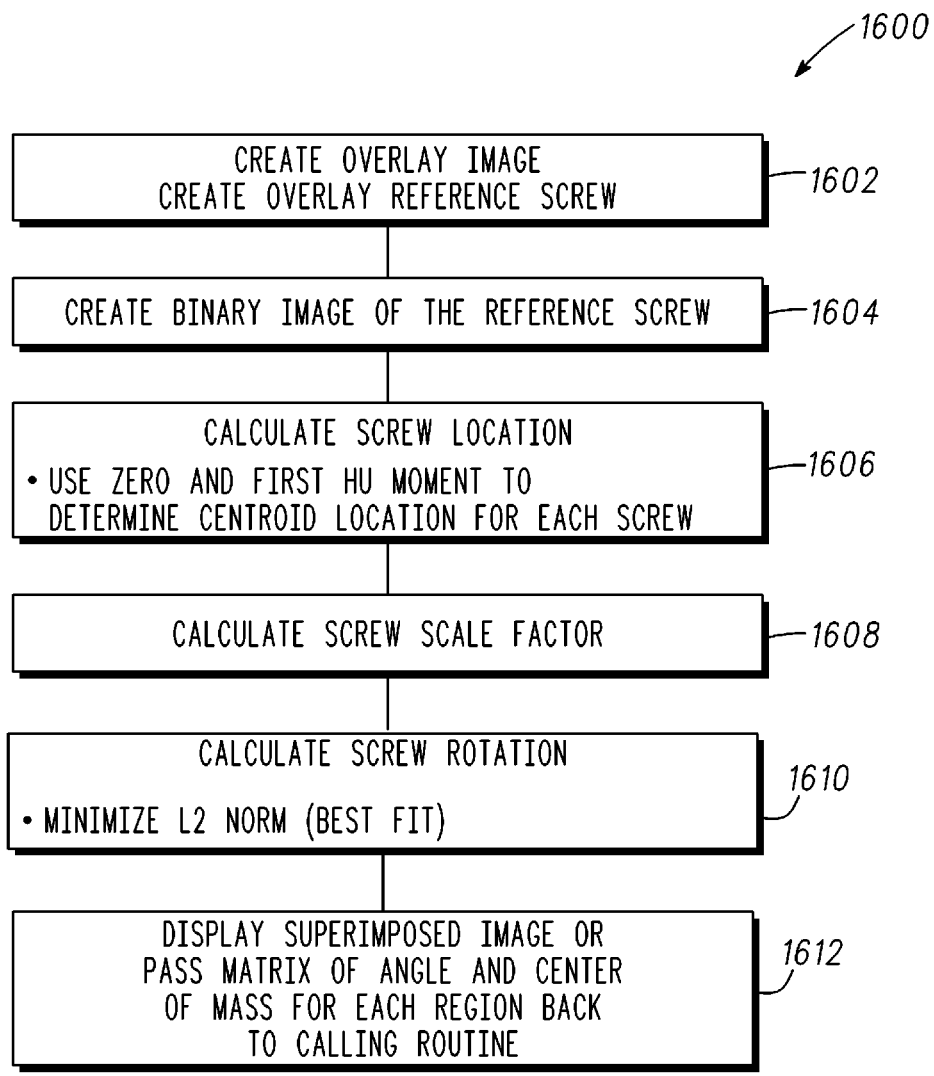
FIG. 41 is a block diagram illustrating steps involved with a computer and computer vision software to place and identify musculoskeletal structures or orthopedic devices in one or more images provided to the computer in accordance with an example embodiment.

FIG. 41 is a block diagram 1600 illustrating steps involved with a computer and computer vision software to place and identify musculoskeletal structures or orthopedic devices in one or more images provided to the computer in accordance with an example embodiment. Block diagram 1600 provides more detail corresponding to the block 1406 of FIG. 39. In general, block diagram 1600 illustrates steps to place a musculoskeletal structure or an orthopedic device that has been identified overlying an image. For example, system 10 of FIG. 1 includes computer vision software that can place the musculoskeletal structure or orthopedic device overlying the image. In an operating room environment overlaying the found object allows a user of the system to determine if the one or more "found" objects have been correctly identified. The user could then respond that the found objects are correct or identify errors that can then cause the system to correct the found objects. The order of the blocks are not fixed and can be performed in any sequence. In the example, one or more fluoroscope images are provided to the computer. In block 1602, an overlay image is created. The overlay image is a reference musculoskeletal structure or a reference orthopedic device. In the example, the object that the system has identified in the image are pedicle screws that are attached to vertebra of the spine. An overlay image of a reference pedicle screw is created in block 1602. In block 1604, a binary image of the reference musculoskeletal or reference orthopedic device image from block 1602 is created by the computer vision software. In the example, the binary image is a pedicle screw which is an orthopedic device. In block 1606, the location of the musculoskeletal structure or orthopedic device is calculated. In the example, the location of the pedicle screws are calculated. The location of the pedicle screws can be found using an image moment. In one embodiment, the zero and first Hu moment is used to determine the centroid location for each for each pedicle screw. Thus, the centroid of each pedicle screw corresponds to the location. In block 1608, the scale factor for each musculoskeletal structure or device that has been identified in an image is calculated after block 1606. The scale factor is calculated by using the Hu Moments to determine the area of the pedicle screw blob. In the example, the scale factor is calculated for the pedicle screws. The scale factor can be calculated relative to the centroid of each pedicle screw. This found scale factor is then applied to the placed reference pedicle screw. In block 1610, the rotation of the musculoskeletal structure or orthopedic device can be calculated after block 1608. In general, the image of the musculoskeletal structure or orthopedic device is rotated for best fit. In the example, the calculation provides the rotation of the pedicle screw image for best fit. In one embodiment, the rotation of each pedicle screw is calculated using a L2 Norm to achieve a best fit. In block 1612, a superimposed image is displayed overlying the original image after block 1610. The image of the identified feature has been located, scaled, and rotated. Placing the image overlying the original image provided to the system should place the identified objects overlying the musculoskeletal structures or orthopedic devices on the original image. In the example, the original image is a fluoroscope image. The overlay image includes the identified musculoskeletal structures or orthopedic devices. In the example, the identified pedicles screws by the computer vision software are overlayed on the image. The overlay image is placed overlying the fluoroscope image on a display and the computer vision identified pedicle screws should align with the pedicle screws in the fluoroscope image. In one embodiment, the user can indicate that the computer and computer vision software has correctly identified the features of interest. Alternatively, the user can indicate that the features of interest are incorrect and that the fluoroscope image needs to be reassessed.

Figure 42A:
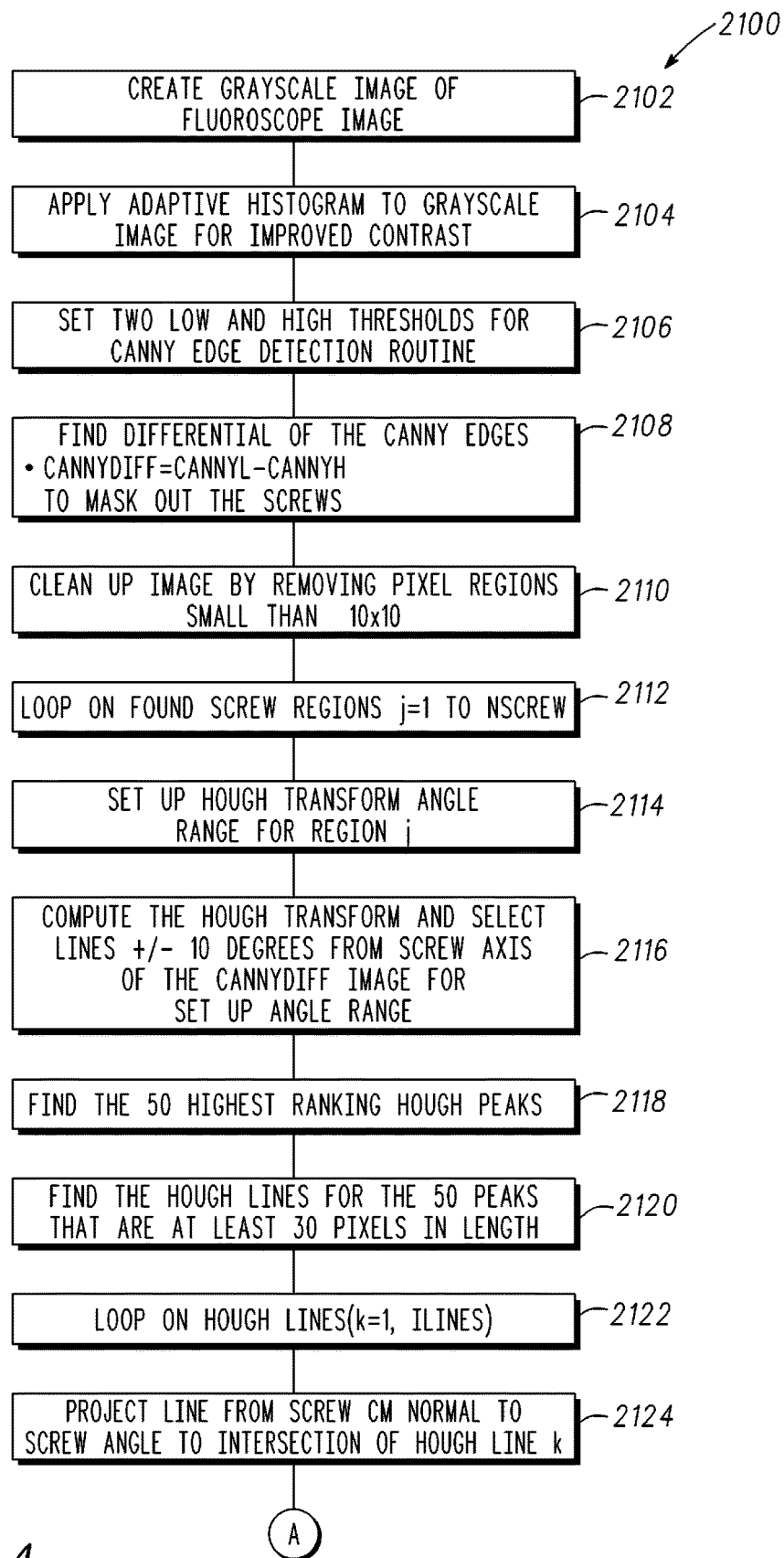
FIG. 42A is a block diagram illustrating steps involved with a computer and computer vision software to place and identify musculoskeletal structures or orthopedic devices in one or more images provided to the computer in accordance with an example embodiment.

FIG. 42A is a block diagram 2100 illustrating steps involved with a computer and computer vision software to place and identify musculoskeletal structures or orthopedic devices in one or more images provided to the computer in accordance with an example embodiment. In the example, musculoskeletal structures are identified by the computer and computer vision software from one or more images. As disclosed herein above, pedicle screws are placed in vertebra of the spine. The pedicle screw is screwed into a vertebra at a predetermined angle and positioned between the endplates of the vertebra thereby determining a relationship between pedicle screw and the vertebra. Typically, the head of the pedicle screw will couple to a surface of the vertebra. A fluoroscope image is used by the computer and computer vision software to locate the pedicle screws as disclosed herein above. In block diagram 2100, a process for identifying vertebra is disclosed. More specifically, the endplates of the vertebra in the fluoroscope image are identified. The endplates can be used to define each vertebra as they form a boundary between vertebrae. The endplates will look like a line or edge on the fluoroscope image. Thus, the pedicle screws and the corresponding vertebra in which they are installed are identified within the fluoroscope image. Moreover, the position of each pedicle screw is known in relation to a corresponding vertebra. This relationship can be measured from the fluoroscope image and the measurements can be used to calculate relative positions of vertebra and pedicle screws to one another. For example, a Cobb angle, dimensional position, spine curvature, listhesis can be calculated as disclosed herein above and measurement data related to position, rotation, translation, and angle related to musculoskeletal structures or orthopedic devices. Also, the positional relationship between the pedicle screws and the vertebra can be used to track spine position as it manipulated or modified during surgery as disclosed herein above. In other words, knowing the position of the pedicle screw also determines the position of the corresponding vertebra to which it couples.

Block diagram 2100 provides more detail corresponding to the block 1408 of FIG. 39. In one embodiment, block diagram 2100 illustrates steps to identify endplates of vertebra on the fluoroscope image. The system 10 of FIG. 1 can be used to identify musculoskeletal structures and orthopedic devices such as endplates of vertebra. The order of the blocks of block diagram 2100 are not fixed and can be performed in any sequence. In the example, one or more fluoroscope images are provided to the computer. In block 2102, a grayscale image of the fluoroscope image is created. In block 2104, equalization is applied to the grayscale image of block 2102. The equalization is applied to improve contrast on the grayscale image to support identification of the musculoskeletal structures or orthopedic devices. In one embodiment, an adaptive histogram is applied to the grayscale image of the spine. The adaptive histogram applies several histograms, where each histogram is applied to a different region of the image. The adaptive histogram will redistribute light and dark areas to improve the contrast of the image in a region. In block 2106, an edge detection routine is applied to the grayscale image that was equalized. The edge detection routine identifies points in a grayscale image where discontinuities exist. For example, an edge detection routine can identify where brightness changes significantly. The change in brightness typically indicates an edge in the image. In one embodiment, Canny edge detection is used on the grayscale image. The edge detection is further enhanced by setting low and high thresholds for the Canny edge detection routine that further highlights changes in brightness. In block 2108, a differential of an edge detection is employed to mask out a feature. In the example a differential of the Canny edges are found. Cannydiff (CannyL—CannyH) is used to mask out the musculoskeletal structures or orthopedic devices. In the example, the pedicle screws are masked out to simplify the task of identifying the endplates. As disclosed above, the pedicle screws were previously identified by the computer vision software and removing the pedicle screws simplifies endplate detection. In block 2110, the image is cleaned up by the computer and computer vision software. The cleanup can comprise removing pixel regions below a predetermined size. In one embodiment, pixel regions smaller than 10×10 are removed from the image.

In block 2112, regions where musculoskeletal region or orthopedic devices have been found are looped on in the computer vision software to repeat a flow disclosed herein below. In the example, pedicle screws have been found previously in the fluoroscope image provided to the computer. It is known that a pedicles screw is inserted into a vertebra of the spine. Thus, focusing on a region where the pedicle screw has been located will include endplates of the vertebra. The loop as stated comprises j=1 to NScrew where NScrew is the number of identified screw regions. Referring to FIG. 47, pedicle screws 2202, 2206, and 2208 were found. Thus, NScrew would be 3 (e.g. 2202, 2206, 2208) for FIG. 47. Each pedicle screw is coupled to a different vertebra. The endplates can be found in regions around pedicle screws 2202, 2206, and 2208 in that image. In block 2114, a feature extraction algorithm is applied to the image. In the example, the feature extraction algorithm can be selected for identifying the endplate of a vertebra. The endplates on the vertebra will appear as lines on the image. In one embodiment, a Hough transform is used. Alternatively, the shaped based feature extraction can also comprise template matching, fuzzy Hough transform, blob extraction, or other extraction type. The Hough transform can be used to find features such as lines, curves, or other features that may be defined in a parametric form. In one embodiment, the Hough transform angle range is set up for region J to support identification of the endplates. In block 2116, the feature extraction algorithm is calculated. In the example, the Hough transform is computed to find the feature. The Hough transform can identify lines in the image. In one embodiment, lines are selected that are + or − 10 degrees from a pedicle screw axis of the Canny diff image for the set up angle range. In block 2118, a predetermined number of features are selected. In the example, endplates of vertebra are being identified by the computer vision software on the image. In one embodiment, the 50 highest ranking Hough peaks are found. The Hough peaks correspond to the parameters of models to be detected (e.g. vertebra endplates). The higher ranking peaks have a higher probability of being endplates or lines corresponding to endplates of a vertebra. In block 2120, the feature extraction process further eliminates identified features to reduce the pool of identified features on the image. In the example, lines corresponding to endplates identified by the Hough transform that are less than a predetermined length are eliminated. In other words, if the identified lines are less than the predetermined length it is likely that they are not endplates of a vertebra. In one embodiment, Hough lines that are at least 30 pixels in length are selected from the lines having the 50 highest ranking Hough peaks.

Figure 42B:
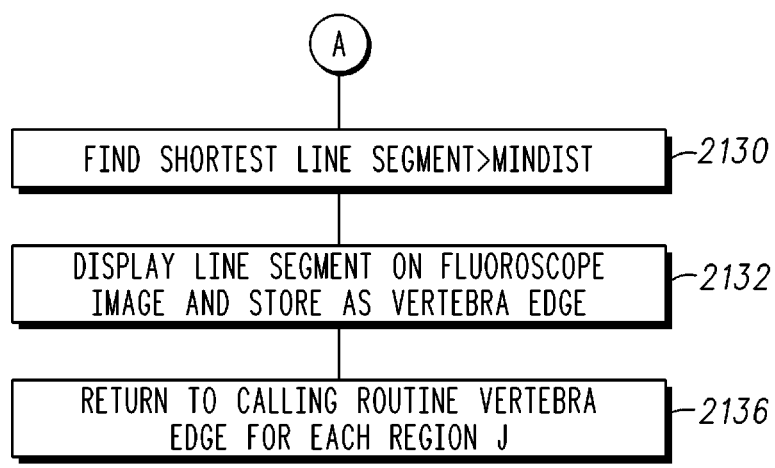
FIG. 42B is a continuation of the block diagram in FIG. 42A in accordance with an example embodiment.

In block 2122, the computer vision software loops on the each object identified by the extraction algorithm. In the example, lines corresponding to endplates are identified by the extraction software. In blocks 2118 and 2120 the number of identified lines by the Hough transform is reduced. In one embodiment, the system loops through the identified Hough lines from k=1 to ILines where ILines is the number of identified lines that are at least 30 pixels in length (block 2120). In block 2124, a line is projected from the previously identified feature center of mass. In the example, the previously identified feature is a pedicle screw. In one embodiment, the line is projected from the center of mass of the pedicle screw normal to the screw angle until it intersects Hough line k. FIG. 42B is a continuation of block diagram 2100 in accordance with an example embodiment. In block 2130, the computer vision software finds the shortest line segment greater than a predetermined value (Mindist) from identified features 1 to ILines. In block 2132, the identified shortest line segment is then overlayed or displayed on the image. The identified shortest line segment is overlayed on the image and can be stored as the identified feature. In the example, the identified shortest line segment corresponds to a vertebra endplate. The line is overlayed on the fluoroscope image. In one embodiment, the user of the system can acknowledge that the computer and computer vision software has correctly identified the vertebra endplate. The system and computer vision software can also identify the specific vertebra and label the vertebra on the image. The line corresponding to the vertebra endplate is stored in memory coupled to the computer and system. In block 2136, the routine loops back to block 2112 where another region is selected corresponding to a previously identified object. In the example, the process will loop back on each region having a pedicle screw.

Figure 43:
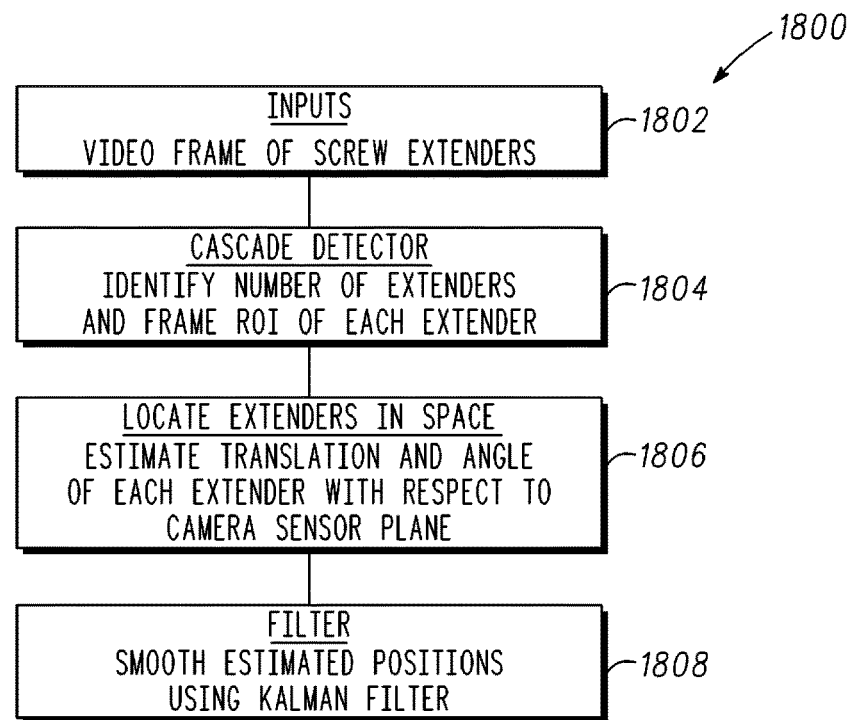
FIG. 43 is a block diagram illustrating tracking of one or more objects using computer vision software in real-time in accordance with an example embodiment.

FIG. 43 is a block diagram 1800 illustrating tracking of one or more objects using computer vision software in real-time in accordance with an example embodiment. In general, system 10 of FIG. 1 disclosed herein can be used for tracking one or more musculoskeletal structures or orthopedic devices. System 10 includes a camera that provides video to the computer. The computer includes computer vision software for identifying and tracking the one or more objects in real-time. In the example disclosed above, pedicle screws are coupled to vertebra of the spine during spine surgery. Pedicle screw extenders are coupled to the pedicle screws. As their name implies, the pedicle screw extenders extend from the spine in a manner where they are visible to a surgeon. The pedicle screw extenders are also visible to the camera providing real-time video to the computer. In general, the computer and computer vision software can identify and track the pedicle screw extenders in real-time in 3D space. The computer vision software can provide position of the pedicle screw extenders relative to one another. As the surgeon manipulates the spine the pedicle screw extenders change position relative to the vertebra to which it couples. Block diagram 1800 illustrates steps to capture the movement of the pedicle screw extenders. The computer vision software provides position data of each pedicle screw extender. In one embodiment, a pedicle screw extender is coupled to a pedicle screw such that the pedicle screw extender is rigidly attached and maintains a fixed geometric position in relation to the pedicle screw. Thus, as disclosed herein above, the position of the pedicle screw extender corresponds to the position of the pedicle screw. Similarly, the position of the pedicle screw corresponds to the position of the vertebra to which it couples. The measurement data related to the pedicle screws and vertebrae positions in 3D space have been captured as disclosed herein above from the fluoroscope image or images. The computer and computer vision software links the tracking of the pedicle screw extenders by the camera to positions of the vertebrae. The real-time measurement data can be used with the measurement data from the fluoroscope image to support and provide quantitative measurement data related to position, rotation, translation, and angle related musculoskeletal structures or orthopedic device or relational measurement data such as dimensional positioning, curvature, or listhesis from the measurement data.

In block 1802, video is provided to the computer having computer vision software. The objects being monitored are within the video frame of the camera. The objects are being monitored in real-time comprise musculoskeletal structures or orthopedic devices. In the example, the objects being monitored are pedicle screw extenders. As disclosed above, the pedicle screw extenders are coupled to pedicle screws that have been fastened to vertebra of the spine. The pedicle screw extenders can be tracked with a complete or partial view as long as each pedicle screw extender can be identified within the video frame by the computer vision software. In block 1804, an object detection algorithm is employed to track musculoskeletal structures or orthopedic devices in real-time. In one embodiment, a cascade detector is trained to detect an object. Alternatively, a Voila-Jones Detector, SVM (Scalar Vector Machine), Bag of Features (Bag of Words) or other object detector can be used. Cascade detectors perform object detection in an efficient manner. A Cascade detector has sequential stages that are designed to cull out objects. Typically, each stage of a Cascade detector becomes progressively more complex where each stage eliminates negative images while leaving positive images that have a high probability of being the object of interest. Ideally, the final stage of the Cascade detector will yield the objects of interest. In the example, the objects are pedicle screw extenders. In one embodiment, the Cascade detector identifies a number of pedicle screw extenders in a video frame and frames a Region of Interest (ROI) around each pedicle screw extender. In block 1806, the musculoskeletal structures or orthopedic devices are located in space. In general, the translation and angle of each musculoskeletal structure or orthopedic device is estimated with respect to a camera sensor plane. In the example, the pedicle screw extenders are located in space. In block 1808, one or more filters are applied to the video frame or objects. In the example, the pedicle screw extenders estimated positions are smoothed using a filter. In one embodiment, the filter is a Kalman filter or a rolling average filter. The Kalman filter is a recursive filter that can process information as it arrives. It is an estimator that infers parameters of interest from indirect, inaccurate and uncertain observations, can be used in real-time applications, and provides the estimate if the data is noisy.

Figure 44:
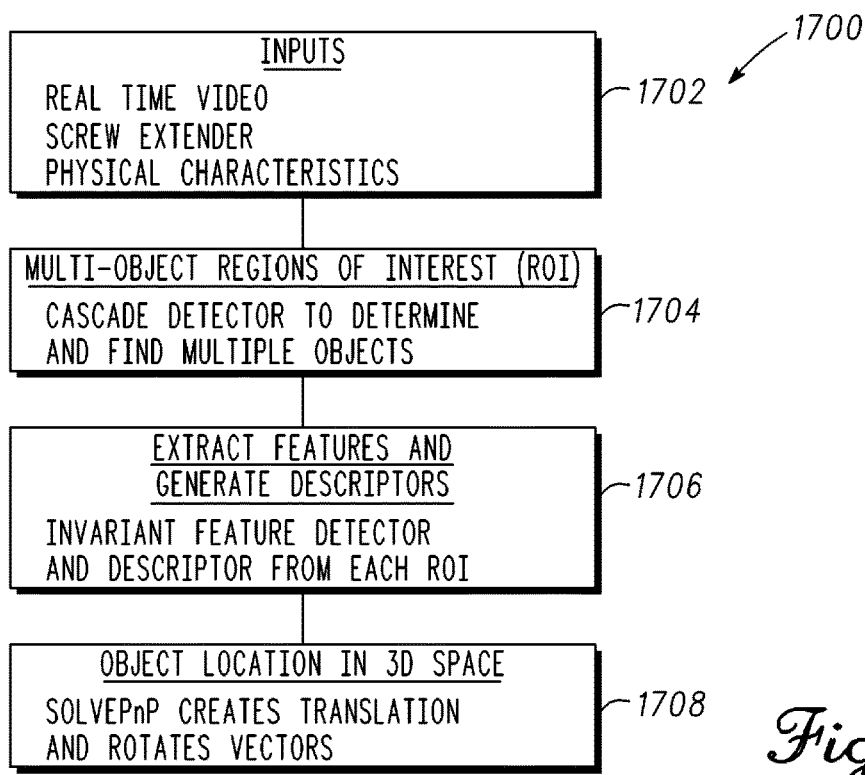
FIG. 44 is a block diagram having further detail illustrating tracking of one or more identified objects using computer vision software in real-time in accordance with an example embodiment.

FIG. 44 is a block diagram 1700 having further detail illustrating tracking of one or more identified objects using computer vision software in real-time in accordance with an example embodiment. In block 1702, a camera provides video in real-time to the computer having computer vision software. The computer will have stored in memory the physical characteristics of the musculoskeletal structures or orthopedic devices being tracked. As mentioned previously, the objects of interest will be partially or completely displayed in each video frame. The computer vision software can identify an object even if a portion of the object is obscured from view. In block 1704, a region of interest (ROI) is formed around an object. Multiple regions of interest are created in a video frame when multiple objects are identified. In the example, a region of interest is formed around each pedicle screw extender. A detector is used to identify each pedicle screw extender in each video frame. In one embodiment, the detector is a Cascade detector. Typically, the pedicle screw extenders will not move significantly from video frame to video frame. In one embodiment, once the regions of interest have been identified there may not be need to identify the objects and create regions of interest around the objects as new video data is provided. The movement of an object such as a pedicle screw extender within a region of interest can be tracked and the region of interest re-centered around the object subsequently. Thus, the identification process is not required with each video frame thereby saving on the computation time required to track objects. In block 1706, descriptors are generated and features are extracted using a feature detector. The features are a set of distinctive keypoints that can be identified in different images, viewpoints, and under noisy conditions. In one embodiment, an invariant feature detector is used. Feature extraction reduces the amount of data that has to be processed. Often much of the data is redundant or irrelevant. Feature extraction transforms the data into a set of features. The feature extraction can be used to compare identified points of interest to other points of interest in an image. Descriptors are generated from each region of interest. The descriptors are descriptions of visual features in images. Descriptors can also describe characteristics such as shape, color or other descriptive characteristic that can be used for identification. In the example, features are extracted related to a pedicle screw extender and descriptors generated on the pedicle screw extender. In block 1708, the object location is determined in 3D space. In one embodiment, a solvePnP function is used by the computer and computer vision software to determine object location. SolvePnP estimates an object pose given a set of object points, their corresponding image projections, the camera matrix, and distortion coefficients. The function typically requires a set of 2D (Dimension) and 3D (Dimension) correspondences related to the camera and an image. In general, the function provides the rotation and translation of the camera with respect to the object of interest. In the example, the objects are the pedicle screw extenders. In other words, the solve PnP function creates translation and rotation vectors related to the camera and objects.

Figure 45:
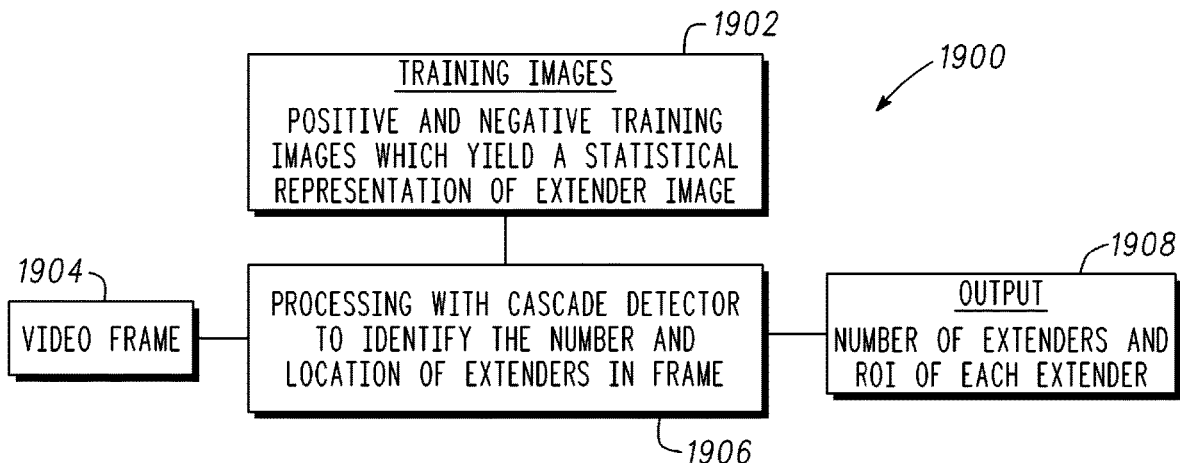
FIG. 45 is a block diagram having further detail illustrating image training using computer vision software in real-time to track one or more objects in accordance with an example embodiment.

FIG. 45 is a block diagram 1900 having further detail illustrating image training using computer vision software in real-time to track one or more objects in accordance with an example embodiment. In block 1904, a camera provides video in real-time to the computer having computer vision software. In block 1902, training images are provided to support identification of a musculoskeletal structure or orthopedic device. In general, the training images comprise positive and negative images. The positive and negative images are static images purposefully gathered prior to running the computer vision algorithm sent through a training algorithm whereby a statistical model is created. The statistical model is then used as the basis to determine if the object was found (e.g. SVM—Support Vector Machine) or in the case of a Cascade classifier used to create the filters as disclosed herein below. The computer will have stored in memory the physical characteristics of the musculoskeletal structures or orthopedic devices being tracked. A Cascade detector utilizes a sequential process to eliminate negative samples and minimize false positive samples. The detector can be trained for different orientations of an object. A trained classifier is comprised of a number of weak stages. The weak stages can be decision stumps. The stages can be trained to improve accuracy by taking a weighted average of the decisions made by the weak stages. The classifier will provide a positive or negative response when viewing a region of an image. A positive response corresponds to the likelihood the object can be found and a negative response corresponds to the likelihood no object will be found. Any positive responses will be provided to the next stage. The detector comprises sequential stages that eliminates negatives samples until only true positives remain. Ideally, each stage will have low false positives if trained correctly. In general, the image training is for a musculoskeletal structure or an orthopedic device. In the example, the image training is for a pedicle screw extender. The positive and negative training images which yield a statistical representation of a pedicle screw extender image is provided to the detector of block 1906. In one embodiment, the detector of block 1906 is a Cascade detector. In block 1904, a video frame is provided to the detector of block 1906. The detector processes the video frame to identify the number and location of pedicle screw extenders in the frame. In block 1908, an output is provided from the detector. The detector identifies a number of pedicle screw extender found in the video frame and provides a region of interest around each pedicle screw extender.

Figure 46:
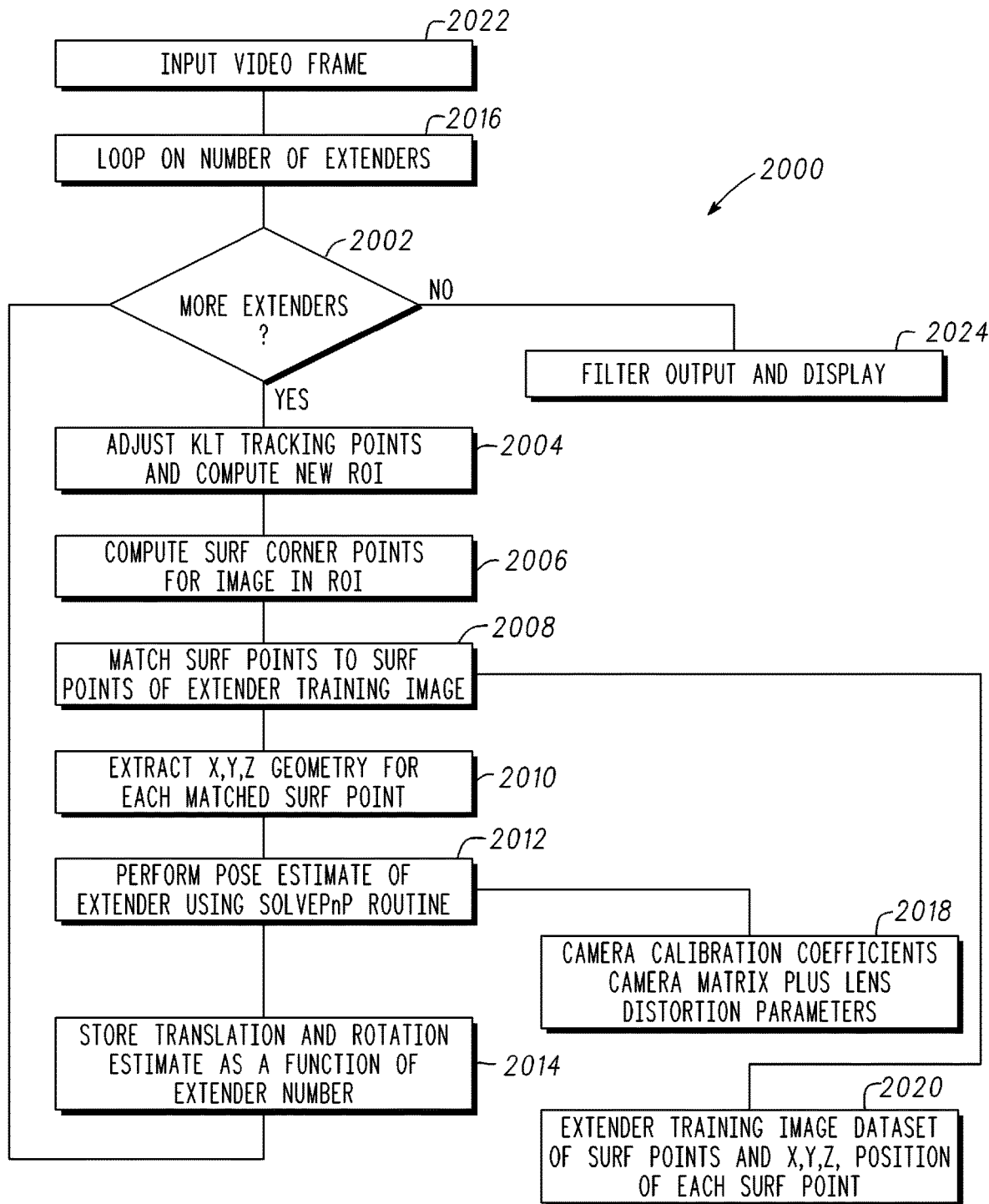
FIG. 46 is a block diagram showing steps to acquire a position of a musculoskeletal structure or orthopedic device in a video frame in real-time in accordance with an example embodiment.

FIG. 46 is a block diagram 2000 showing steps to acquire a position of a musculoskeletal structure or orthopedic device in a video frame in real-time in accordance with an example embodiment. As mentioned previously, system 10 of FIG. 1 can track the musculoskeletal structure or orthopedic device in an operating room in real-time to support surgery. System 10 includes a computer and computer vision software. The pedicle screw extender couples to a pedicle screw. The pedicle screw is screwed into a vertebra of the spine. Tracking the pedicle screw extenders provides quantitative measurement information related to the pedicle screws and vertebra. The tracking data is used in conjunction with quantitative measurement data generated from the computer processing one or more fluoroscope images using the computer vision software. In the example, the surgery is spine surgery where pedicle screw extenders are tracked in real-time to generate quantitative measurement data related to the position of each vertebra and the shape of the spine.

In block 2022, a camera provides a video frame. In block 2016, the video frame is looped on to find a number of objects in the video frame. The objects are musculoskeletal structures or orthopedic devices. In the example, the objects are pedicle screw extenders. In block 2002, a decision block continues to process the video frame if it is believed that there may be other musculoskeletal structures or orthopedic devices that have not been found in the video frame. In block 2004, the tracking points are adjusted. For example, two consecutive video frames can be reviewed using a feature tracking algorithm. The feature tracking algorithm can determine how points being tracked move from frame to frame. In one embodiment, the movement can be performed using a least squares fit. The adjustment includes computing new regions of interest (ROI) around the musculoskeletal structures or orthopedic devices. In the example, the feature tracking algorithm looks for point movement related to the pedicle screw extenders. The feature tracking algorithm can be a KLT (Kanade-Lucas-Tomasi) feature tracking algorithm that works well for real-time tracking. In block 2006, a features detector is used on an image in a ROI from block 2004. The features detector can be used for object recognition, object registration, object classification, or 3 dimensional (3D) reconstruction. In one embodiment, a speed up robust features (SURF) detector is used on an image in the ROI. Alternatively, SIFT (scale invariant feature transformation), MSURF, ORB, FAST, (Histogram of Gradients), Brisk, Harris, or other feature detectors or feature matching can be used. The SURF algorithm can be used for feature extraction and continuous recognition in video. The SURF algorithm can track objects by interest point matching and updating. The SURF detector is used to compute SURF corner points for an image in each ROI. In general, a corner is an intersection of two edges. The corner corresponds to a change in the gradient in the image. Both edges of a corner change directions in the image at the corner point whereby the change can be detected readily. Block 2020 comprises the musculoskeletal structure or orthopedic device training image data set. The training image data set can include SURF points, SURF corner points, and X, Y, Z position of each SURF point and SURF corner points. In the example, block 2020 can provide SURF points, SURF corner points, and X, Y, Z position of each SURF point and SURF corner point of the pedicle screw extender. In block 2008, the SURF points from the image in the ROI are compared to the SURF points of the musculoskeletal structure or orthopedic device training image. The comparison can also be between SURF corner points from the image in the ROI compared to the SURF corner points of the musculoskeletal structure or orthopedic device. In the example, the SURF corner points from ROI are compared to SURF corner points of the pedicle screw extender image. Block 2008 receives the training image set from block 2020. In block 2010, the X, Y, Z, geometry is extracted for each matched SURF point or corner point. Block 2018 comprises camera calibration coefficients, camera matrix, and lens distortion parameters. In block 2012, a pose estimate is performed of the musculoskeletal structure or orthopedic device. Block 2018 provides the camera calibration coefficients, camera matrix, and lens distortion parameters to block 2012. The pose estimator estimates the 3 dimensional (3D) rotation and translation of a 3D object from a 2 dimensional (2D) image. In general, the 3D pose is estimated from X, Y, Z model points and the 2D image points. In the example, the pose estimate is performed on the pedicle screw extender in the ROI. In one embodiment the pose estimate is performed using solvePnP (solve pose and position). In block 2014, the translation and rotation estimate of the musculoskeletal structure or orthopedic device is stored in memory coupled to the computer. The translation and rotation estimate is linked to musculoskeletal structure or orthopedic device in the ROI. In the example, the translation and rotation estimate is stored and linked to pedicle screw extender in the ROI. Block 2014 then loops back to decision block 2002. The program loops through blocks 2004, 2006, 2008, 2010, 2012, and 2014 until there are no more musculoskeletal structures or orthopedic devices. In the example, the loop ends when there are no more pedicle screw extenders in the image or regions of interest and the translation and rotation of each identified pedicle screw extender is defined. Upon completing the loop, the output is filtered and displayed in block 2024. Thus, the musculoskeletal structure or orthopedic device is tracked with each video frame and the position in 3D space is known in each video frame. As mentioned previously, the quantitative measurement data generated in this process can be used to generate parameters needed to assess or measure the musculoskeletal structure of interest. In the example, the pedicle screw extender 3D position can be used to calculate a Cobb angle, spine curvature, or vertebra position and rotation as the position of the pedicle screw extender directly relates to the position of the vertebra to which it couples.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. An orthopedic operating room system comprising:
   a camera configured to be focused on a region of interest of a patient;
   a computer having computer vision software, wherein the computer is coupled to the camera, wherein the computer is configured to identify one or more bone landmarks in the region of interest and to recognize a type of bone from the one or more identified landmarks, and wherein the computer is configured to calculate one or more metrics related to the one or more recognized bones from image data provided in real-time by the camera; and
   a display coupled to the computer, wherein the computer is configured to illustrate the one or more bones on the display, wherein the computer is configured to monitor movement of the one or more recognized bones and illustrate positions of the one or more bones in real-time on the display as the one or more bones are manipulated, wherein the computer stores at least one position of the one or more bones when the one or more bones are positioned to achieve a desired outcome as measured in the one or more metrics, and the desired outcome is used to calculate at least one characteristic for an implant system configured to maintain the desired outcome, and wherein the computer is configured to display, on a screen of the display, one or more preoperative images illustrating the recognized bones, a measurement grid overlayed on one or more of the preoperative images and, simultaneously with and adjacent to the one or more preoperative images, at least one of:
      one or more intraoperative images illustrating the one or more bones for comparison with the adjacent preoperative image, and
      one or more images illustrating the one or more bones after the implant system is installed for comparison with the adjacent preoperative image.

2. The orthopedic operating room system of claim 1, wherein a pre-operative plan is displayed on the screen of the display and adjacent to the one or more preoperative images, wherein the pre-operative plan includes one or more pre-operative metrics, and wherein the pre-operative metrics can be compared against the one or more metrics generated from the image data provided in real-time by the camera, wherein the one or more metrics generated from the image data provided in real-time are displayed on the screen of the display adjacent the one or more intraoperative images or adjacent the one or more images illustrating the one or more bones after the implant system is installed.

3. The orthopedic operating room system of claim 1, wherein a target couples to a bone of the one or more bones, wherein the target can be viewed by the camera in the region of interest, wherein the computer is configured to use the computer vision software to track the target, and wherein the computer vision software can identify a position of the bone from the target.

4. An orthopedic operating room system comprising:
   a camera configured to be focused on a region of interest;
   a computer, wherein the computer is configured to receive image data from the camera; and
   a display including a screen and coupled to the computer, wherein:
      one or more bones of a musculoskeletal system are illustrated on the display,
      the computer is configured to run computer vision software,
      the computer vision software is configured to recognize components of the musculoskeletal system,
      the computer vision software is configured to identify the one or more bones on the display,
      the computer is configured to calculate one or more metrics related to the one or more bones from image data provided in real-time by the camera,
      the computer is configured to display a table, on the screen, the table containing the calculated one or more metrics, the one or more metrics including a sagittal Cobb angle, a coronal Cobb angle, and an axial rotation,
      the computer is configured to display, on the screen, one or more preoperative images illustrating the one or more bones, and
      the computer is configured to display, on the screen and simultaneously with and adjacent to the one or more preoperative images, one or more intraoperative images illustrating the one or more bones for comparison with the adjacent preoperative image.

5. The orthopedic operating room system of claim 4, wherein a fluoroscope takes one or more fluoroscope images of the region of interest, wherein the camera is used to provide the one or more fluoroscope images to the computer, wherein the computer vision software is configured to identify one or more features or landmarks of each bone of the one or more bones, wherein the computer vision software recognizes each bone of the one or more bones from the one or more features or land marks of each bone, and wherein the computer is configured to display an overlay image that includes the fluoroscope image.

6. The orthopedic operating room system of claim 4, further including a target coupled to a bone of the one or more bones, wherein the camera is configured to view the target when the bone cannot be viewed by the camera, wherein the computer vision software is configured to calculate a position of the bone from the target, wherein each bone of the one or more bones has a corresponding target.

7. The orthopedic operating room system of claim 4, wherein the display is configured to illustrate:
   movement of the one or more bones in real-time to support positioning using the one or more metrics to achieve a desired outcome, and a pre-operative plan including one or more pre-operative metrics, wherein the pre-operative metrics are compared against the one or more metrics generated from the image data provided in real-time by the camera.

8. The orthopedic operating room system of claim 7, wherein the computer stores a position of the one or more bones when the one or more bones are positioned to achieve the desired outcome.

9. An orthopedic operating room system comprising:
a camera configured to be focused on a region of interest;
a computer, wherein the computer is configured to receive image data from the camera; and
a display coupled to the computer, wherein:
   vertebrae of a musculoskeletal system are illustrated on the display,
   the computer is configured to run computer vision software,
   the computer vision software is configured to recognize bone landmarks of the vertebrae, the bone landmarks including a first endplate of the vertebrae and a second endplate of the vertebrae, wherein the first endplate defines a first plane, and the second endplate defines a second plane,
   the computer vision software is configured to identify at least one vertebra of the vertebrae on the display,
   the computer is configured to calculate one or more metrics related to the vertebrae from image data provided in real-time by the camera,
   the calculated one or more metrics are displayed on the display,
   the calculated one or more metrics includes a first identified angle defined between two bones in the region of interest, the first identified angle defined by an intersection of the first plane and the second plane, and
   the computer is configured to indicate when the one or more metrics indicate achieving a desired outcome.

10. The orthopedic operating room system of claim 9, wherein each vertebra has a corresponding pedicle screw, wherein the computer vision software can determine a position of each vertebra from the corresponding pedicle screw, wherein the display is configured to illustrate positioning of the vertebrae as a spine is manipulated in real time, wherein each pedicle screw has a corresponding pedicle screw extender, wherein the computer vision software can determine a position of each vertebra from the corresponding pedicle screw extender, and wherein the calculated one or more metrics includes an angle defined between the pedicle screw extender and the first plane or the second plane, and wherein the computer vision software is configured to determine a position of the pedicle screw based on one or more determined Hu moments.

11. The orthopedic operating room system of claim 9, wherein the computer is configured to store a position of the vertebrae in the computer when the desired outcome is achieved as determined by the one or more metrics, wherein the position of the vertebrae stored in the computer is used to bend a rod, and wherein the rod is configured to be coupled to pedicle screws to shape a spine.

12. The orthopedic operating room system of claim 9, wherein the first identified angle is between a first vertebra and a second vertebra of the vertebrae, the first endplate is a distal endplate of the first vertebra, and the second endplate is a proximal endplate of the second vertebra.

13. The orthopedic operating room system of claim 12, wherein an intermediary vertebra is positioned between the first vertebra and the second vertebra.

14. The orthopedic operating system of claim 9, wherein the first identified angle is calculated in a coronal plane of the two bones, wherein the calculated one or more metrics includes a second identified angle calculated in a sagittal plane of the two bones, and wherein the calculated one or more metrics includes a measurement of axial rotation.

15. The orthopedic operating system of claim 9, wherein:
the vertebrae include a first vertebra, a second vertebra, and a third vertebra,
the region of interest includes the first vertebra, the second vertebra, and the third vertebra,
the first endplate is a distal endplate of the first vertebra, and the second endplate is a proximal endplate of the second vertebra,
the third vertebra is positioned between the first vertebra and the second vertebra,
the first identified angle is calculated in a coronal plane of the two bones,
the calculated one or more metrics includes a second identified angle calculated in a sagittal plane of the two bones, and
the computer is configured to display, on the display, a preoperative illustration of the first vertebra, the second vertebra, and the third vertebra, preoperative measurements of the first identified angle and the second identified angle, an intraoperative illustration of the first vertebra, the second vertebra, and the third vertebra, and intraoperative measurements of the first identified angle and the second identified angle.

16. The orthopedic operating room system of claim 9, wherein the computer vision software is further configured to identify a pedicle screw coupled to the at least one vertebra, and utilize an identified location of the pedicle screw to determine the first plane and the second plane.

17. The orthopedic operating room system of claim 9, wherein the system further comprises a spine rod, and the calculated one or more metrics include a Cobb angle, and wherein the spine rod is shaped or adjusted based on the calculated Cobb angle to achieve the desired outcome.

* * * * *